United States Patent
Schiffer-Mannioui

(10) Patent No.: US 10,752,684 B2
(45) Date of Patent: Aug. 25, 2020

(54) ROR1 (NTRKR1) SPECIFIC CHIMERIC ANTIGEN RECEPTORS FOR CANCER IMMUNOTHERAPY

(71) Applicant: Cellectis, Paris (FR)

(72) Inventor: Cècile Schiffer-Mannioui, Villiers-sur-Marne (FR)

(73) Assignee: CELLECTIS, Paris (FR)

( * ) Notice: Subject to any disclaimer, the term of this patent is extended or adjusted under 35 U.S.C. 154(b) by 178 days.

(21) Appl. No.: 15/329,932

(22) PCT Filed: Jul. 29, 2015

(86) PCT No.: PCT/EP2015/067444
§ 371 (c)(1),
(2) Date: Jan. 27, 2017

(87) PCT Pub. No.: WO2016/016344
PCT Pub. Date: Feb. 4, 2016

(65) Prior Publication Data
US 2017/0283497 A1    Oct. 5, 2017

(30) Foreign Application Priority Data
Jul. 29, 2014  (DK) .................................. 2014 70465

(51) Int. Cl.
| | |
|---|---|
| *C07K 16/28* | (2006.01) |
| *C07K 16/30* | (2006.01) |
| *C07K 14/705* | (2006.01) |
| *C07K 14/725* | (2006.01) |
| *C12N 5/0783* | (2010.01) |
| *A61K 48/00* | (2006.01) |
| *A61K 35/17* | (2015.01) |
| *C12N 5/10* | (2006.01) |
| *C12N 15/62* | (2006.01) |
| *A61K 39/00* | (2006.01) |
| *C07K 19/00* | (2006.01) |

(52) U.S. Cl.
CPC .......... *C07K 16/2803* (2013.01); *A61K 35/17* (2013.01); *A61K 48/00* (2013.01); *C07K 14/7051* (2013.01); *C07K 14/70517* (2013.01); *C07K 16/30* (2013.01); *C12N 5/0636* (2013.01); *C12N 5/10* (2013.01); *C12N 15/62* (2013.01); *A61K 39/00* (2013.01); *A61K 2039/505* (2013.01); *A61K 2039/5156* (2013.01); *A61K 2039/5158* (2013.01); *A61K 2039/572* (2013.01); *C07K 19/00* (2013.01); *C07K 2317/24* (2013.01); *C07K 2317/53* (2013.01); *C07K 2317/622* (2013.01); *C07K 2319/02* (2013.01); *C07K 2319/03* (2013.01); *C07K 2319/33* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 5,585,089 A | 12/1996 | Queen et al. |
| 5,766,886 A | 6/1998 | Studnicka et al. |
| 5,858,358 A | 1/1999 | June et al. |
| 5,883,223 A | 3/1999 | Gray |
| 6,010,613 A | 1/2000 | Walters et al. |
| 6,352,694 B1 | 3/2002 | June et al. |
| 6,407,213 B1 | 6/2002 | Carter et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 2003/0105000 A1 | 6/2003 | Pero et al. |

(Continued)

FOREIGN PATENT DOCUMENTS

| | | |
|---|---|---|
| EP | 0239400 | 8/1994 |
| EP | 0592106 | 11/2004 |

(Continued)

OTHER PUBLICATIONS

Mariuzza et al. (Annu. Rev. Biophys. Biophys. Chem., 16: 139-159, 1987).*

(Continued)

*Primary Examiner* — Brad Duffy
(74) *Attorney, Agent, or Firm* — Fish & Richardson P.C.

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a ROR1 monoclonal antibody, conferring specific immunity against ROR1 positive cells. The engineered immune cells endowed with such CARs are particularly suited for treating lymphomas and leukemia, and for solid tumors such as breast, colon, lung, and kidney tumors.

10 Claims, 21 Drawing Sheets
Specification includes a Sequence Listing.

(56) References Cited

U.S. PATENT DOCUMENTS

| | | | |
|---|---|---|---|
| 2005/0042664 | A1 | 2/2005 | Wu et al. |
| 2005/0048617 | A1 | 3/2005 | Wu et al. |
| 2006/0121005 | A1 | 6/2006 | Berenson et al. |
| 2007/0231333 | A1 | 10/2007 | Boghaert et al. |
| 2013/0280221 | A1* | 10/2013 | Schonfeld .......... C07K 14/5443 424/93.21 |
| 2013/0287748 | A1 | 10/2013 | June et al. |
| 2014/0234348 | A1* | 8/2014 | Scholler ............... C07K 14/465 424/184.1 |

FOREIGN PATENT DOCUMENTS

| | | |
|---|---|---|
| EP | 519596 | 2/2005 |
| JP | 2014/510108 | 4/2014 |
| WO | WO 91/09967 | 7/1991 |
| WO | WO 93/17105 | 9/1993 |
| WO | WO 2004/083379 | 9/2004 |
| WO | WO 2012/012695 A2 | 1/2012 |
| WO | WO 2012/097313 A2 | 7/2012 |
| WO | WO 2012/138927 | 10/2012 |
| WO | WO 2013/033626 | 3/2013 |
| WO | WO 2013/063419 | 5/2013 |
| WO | WO 2013/123061 | 8/2013 |
| WO | WO 2013/176915 | 11/2013 |
| WO | WO 2014/031174 A1 | 2/2014 |
| WO | WO 2014/031687 | 2/2014 |
| WO | WO 2014/039523 A1 | 3/2014 |

OTHER PUBLICATIONS

Hudecek et al., "Receptor Affinity and Extracellular Domain Modifications Affect Tumor Recognition by ROR1-Specific Chimeric Antigen Receptor T Cells," Clinical Cancer Research, Apr. 25, 2013, pp. 3153-3164, vol. 19, No. 12.
International Search Report and Written Opinion issued in PCT/EP2015/067444 dated Oct. 19, 2015.
Poirot et al., "521. Multiplex Genome Editing of TCR α/CD52 Genes as a Platform for "Off the Shelf" Adoptive T-Cell Immunotherapies.," 17the Annual Meeting of the American-Society-of-Gene-and-Cell-Therapy (ASGCT), May 1, 2014, pp. S201-S202, vol. 22 (Suppl. 1), Washington DC USA.
Poirot et al., "T-Cell Engineering for "off-The-shelf" Adoptive Immunotherapy," Blood Journal: 122, Nov. 15, 2013.
Schiffer Mannioui et al, "Treatment of B cells malignancies with anti-CD19 CAR+, TCR-, CD52-allogeneic T cells," Journal for ImmunoTherapy of Cancer, BioMed Central Ltd, London UK, Nov. 7, 2013, p. P34, vol. 1, No. Suppl 1.
Arimondo et al., "Exploring the cellular activity of camptothecin-triple-helix-fonning oligonucleotide conjugates," Mol. Cell Biol., 26(1):324-33, Jan. 2006.
Atkins et al.,"A case for "StopGo": reprogramming translation to augment codon meaning of GGN by promoting unconventional termination (Stop) after addition of glycine and then allowing continued translation (GO)," Rna., 13(6):803-10, Jun. 2007.
Baskar et al., "Unique cell surface expression of receptor tyrosine kinase ROR1 in human B-cell chronic lymphocytic leukemia," Clin. Cancer Res. Off. J. Am. Assoc. Cancer Res., 14(2):396-404, Jan. 2008.
Bicocca et al., "Crosstalk between ROR1 and the Pre-B cell receptor promotes survival of t (1; 19) acute lymphoblastic leukemia," Cancer Cell, 22(5):656-667, Nov. 2012.
Bierer et al., "Cyclosporin A and FK506: molecular mechanisms of immunosuppression and probes for transplantation biology," Curr. Opin. Immunol., 5(5):763-73, Oct. 1993.
Birkle et al., "Role of tumor-associated gangliosides in cancer progression," Biochimie., 85(3-4):455-463, Mar.-Apr. 2003.
Boch et al., "Breaking the code of DNA binding specificity of TAL-type III effectors," Science, 326(5959):1509-12, Dec. 2009.

Carsberg et al., "Metastasis-associated 5T4 oncofoetal antigen is concentrated at microvillus projections of the plasma membrane," J. Cell Sci., 108(8):2905-16, Aug. 1995.
Castro et al., "5T4 oncofetal antigen is expressed in high risk of relapse childhood pre-B acute lymphoblastic leukemia and is associated with a more invasive and chemotactic phenotype," Leukemia., 26(7):1487-98, Jul. 2012.
Choudhury et al., "Silencing of ROR1 and FMOD with siRNA results in apoptosis of CLL cells," Br. J. Haematol., 151(4):327-335, Nov. 2010.
Choulika et al., "Induction of homologous recombination in mammalian chromosomes by using the I-Seel system of *Saccharomyces cerevisiae*," Mol. Cell. Biol., 15(4):1968-73, Apr. 1995.
Christian et al., "Targeting DNA double-strand breaks with TAL effector nucleases," Genetics, 186(2):757-61, Oct. 2010.
Cong et al., "Multiplex genome engineering using CRISPR/Cas systems," Science, 339(6121):819-23, Feb. 2013.
Cooper, "L. Innovative T Cell-Targeted Therapy for Ovarian Cancer," Annual Report 2012 prepared for US Army medical research and Medical Command.
Cros et al., "Problems related to resistance to cytarabine in acute myeloid leukemia," Leukemia & Lymphoma, 45(6):1123-1132, Jun. 2004.
Daneshmanesh et al., "Ror1, a cell surface receptor tyrosine kinase is expressed in chronic lymphocytic leukemia and may serve as a putative target for therapy," Int. J. Cancer, 123(5):1190-5, Sep. 2008.
Daniotti et al., "Cloning, characterization and developmental expression of alpha2,8 sialyltransferase (GD3 synthase, ST8Sia I) gene in chick brain and retina," Int. J. Dev. Neurosci., 15(6):767-776, Oct. 1997.
Dave et al., "Restricted cell surface expression of receptor tyrosine kinase ROR1 in pediatric B-lineage acute lymphoblastic leukemia suggests targetability with therapeutic monoclonal antibodies," PLoS One., 7(12):e52655, Dec. 2012.
Deltcheva et al., "CRISPR RNA maturation by trans-encoded small RNA and host factor RNase III," Nature, 471(7340):602-7, Mar. 2011.
Donelly et al., "The cleavage activities of aphthovirus and cardiovirus 2A proteins," J. Gen. Virol., 78:13-21, Jan. 1997.
Donnelly and Elliott, "Nuclear localization and shuttling of herpes simplex virus tegument protein VP13/14," J. Virol., 75(6):2566-74, Mar. 2001.
Donnelly et al., "Analysis of the aphthovirus 2A/2B polyprotein 'Cleavage' mechanism indicates not a proteolytic reaction, but a novel translational effect: a putative ribosomal 'skip'," J. Gen. Virol., 82:1013-1025, May 2001.
Doronina et al., "Site-specific release of nascent chains from ribosomes at a sense codon," Mol. Cell Biol., 28(13):4227-39, Jul. 2008.
Dotti et al., "Redirecting T-cell specificity by introducing a tumor-specific chimeric antigen receptor," Blood., 116(7):1035-1044, Aug. 2010.
Eisenschmidt et al., "Developing a programmed restriction endonuclease for highly specific DNA cleavage." Nucleic. Acids. Res., 33(22):7039-47, Jan. 2005.
Fukuda et al., "Antisera induced by infusions of autologous Ad-CD154-leukemia B cells identify ROR1 as an oncofetal antigen and receptor for Wnt5a," Proc. Natl. Acad. Sci. U.S.A., 105(8):3047-3052, Feb. 2008.
Gardin et al., "Postremission treatment of elderly patients with acute myeloid leukemia in first complete remission after intensive induction chemotherapy: results of the multicenter randomized Acute Leukemia French Association (ALFA) 9803 trial," Blood., 109(12):5129-5135, Jun. 2007.
Garneau et al., "The CRISPR/Cas bacterial immune system cleaves bacteriophage and plasmid DNA," Nature, 468(7320):67-71, Nov. 2010.
Gasiunas et al., "Cas9-crRNA ribonucleoprotein complex mediates specific DNA cleavage for adaptive immunity in bacteria," Proc. Natl. Acad. Sci. U.S.A., 109(39):E2579-86, Sep. 2012.
GenBank Association No. AAA53133.1, "4-1BB [*Homo sapiens*]," Nov. 27, 1994, 2 pages.

(56) References Cited

OTHER PUBLICATIONS

GenBank Association No. NP001139345.1, "T-cell surface glycoprotein CD8 alpha chain isoform 1 precursor [*Homo sapiens*]," Mar. 15, 2015, 3 pages.
GenBank Association No. NP001992.1, "high affinity immunoglobulin epsilon receptor subunit alpha precursor [*Homo sapiens*]," Jan. 15, 2016, 3 pages.
GenBank Association No. NP006130.1, "T-cell-specific surface glycoprotein CD28 isoform 1 precursor [*Homo sapiens*]," Mar. 15, 2015, 3 pages.
Gentile et al., "Ror1 is a pseudokinase that is crucial for Met-driven tumorigenesis," Cancer Res., 71(8):3132-3141, Apr. 2011.
Gravotta et al., "In vivo and in vitro expression of gangliosides in chick retina Müeller cells," J. Neurochem., 52(3):768-776, Mar. 1989.
Guest et al., "The role of extracellular spacer regions in the optimal design of chimeric immune receptors: evaluation of four different scFvs and antigens," J. Immunother., 28(3):203-211, May 2005.
Haraguchi et al., "Isolation of GD3 synthase gene by expression cloning of GM3 alpha-2,8-sialyltransferase cDNA using anti-GD2 monoclonal antibody," Proc. Natl. Acad. Sco. U.S.A., 91(22):10455-10459, Oct. 1994.
Haynes et al., "Redirecting mouse CTL against colon carcinoma: superior signaling efficacy of single-chain variable domain chimeras containing TCR-zeta vs Fc epsilon RI-gamma," J. of Immunol., 166(1):182-187, Jan. 2001.
Henderson et al., "Comparison of the effects of FK-506, cyclosporin A and rapamycin on IL-2 production," Immunology, 73(3):316-21, Jul. 1991.
Hole and Stern., "A 72 kD trophoblast glycoprotein defined by a monoclonal antibody," Br. J. Cancer, 57(3):239-246, Mar. 1988.
Jena et al., "Redirecting T-cell specificity by introducing a tumor-specific chimeric antigen receptor," Blood, 116(7):1035-44, Aug. 2010.
Jinek et al., "A programmable dual-RNA—guided DNA endonuclease in adaptive bacterial immunity," Science, 337(6096):816-21, Jun. 2012.
Jun. et al., "T cells with chimeric antigen receptors have potent antitumor effects and can establish memory in patients with advanced leukemia," Sci. Transl. Med., 3(95):95ra73, Aug. 2011.
Kalish and Glazer, "Targeted genome modification via triple helix formation," Ann. N.Y. Acad. Sci., 1058(1):151-61, Nov. 2005.
Klein et al., "Gene expression profiling of B cell chronic lymphocytic leukemia reveals a homogeneous phenotype related to memory B cells," J. Exp. Med., 194:1625-1638, Dec. 2001.
Li et al., "TAL nucleases (TALNs): hybrid proteins composed of TAL effectors and FokI DNA-cleavage domain," Nucleic. Acids. Res., 39(1):359-72, Jan. 2011.
Liu et al., "Calcineurin is a common target of cyclophilin-cyclosporin A and FKBP-FK506 complexes," Cell, 66(4):807-815, Aug. 1991.
Liu et al., "Inhibition of T cell signaling by immunophilin-ligand complexes correlates with loss of calcineurin phosphatase activity," Biochemistry., 31(16):3896-901, Apr. 1992.
Lo et al., "Anti-GD3 chimeric sFv-CD28/T-cell receptor zeta designer T cells for treatment of metastatic melanoma and other neuroectodermal tumors," Clin. Cancer Res., 16(10):2769-2780, May 2010.
Mali et al., "RNA-guided human genome engineering via Cas9," Science, 339(6121):823-6, Feb. 2013.
Matsuda et al., "Expression of the receptor tyrosine kinase genes, Ror1 and Ror2, during mouse development," Mech. Dev., 105(1-2):153-156, Jul. 2001.
Moscou and Bogdanove, "A simple cipher governs DNA recognition by TAL effectors," Science, 326(5959):1501, Dec. 2009.
Nakayama et al., "Expression cloning of a human GT3 synthase. GD3 and GT3 are synthesized by a single enzyme," J. Biol. Chem., 271(7):3684-91, Feb. 1996.
Padlan, "A possible procedure for reducing the immunogenicity of antibody variable domains while preserving their ligand-binding properties," Mol. Immunol., 28(4-5):489-498, Apr.-May 1991.

Paques and Duchateau, "Meganucleases and DNA double-strand break-induced recombination: perspectives for gene therapy," Curr. Gene Ther., 7(1):49-66, Feb. 2007.
Park et al., "Treating cancer with genetically engineered T cells," Trends Biotechnol., 29(11):550-7, Nov. 2011.
Peipp et al., "Efficient eukaryotic expression of fluorescent scFv fusion proteins directed against CD antigens for FACS applications," J. Immunol. Methods, 285(2):265-80, Feb. 2004.
Perrin et al., "Asymmetrical recognition and activity of the I-SceI endonuclease on its site and on intron-exon junctions," Embo. J., 12(7):2939-47, Jul. 1993.
Pingoud and Silva, "Precision genome surgery," Nat. Biotechnol., 25(7):743-4, Jul. 2007.
Porter et al., "Chimeric antigen receptor-modified T cells in chronic lymphoid leukemia," N. Engl. J. Med., 365(8):725-733, Aug. 2011.
Porteus and Carroll, "Gene targeting using zinc finger nucleases," Nat. Biotechnol., 23(8):967-73, Aug. 2005.
Reaman et al., "Anti-GD3 monoclonal antibody analysis of childhood T-cell acute lymphoblastic leukemia: detection of a target antigen for antibody-mediated cytolysis," Cancer Res., 50(1):202-205, Jan. 1990.
Reddy et al., "Localization of the human Ror1 gene (NTRKR1) to chromosome 1p31-p32 by fluorescence in situ hybridization and somatic cell hybrid analysis," Genomics, 41(2):238-5, Apr. 1997.
Rosenwald et al., "Relation of gene expression phenotype to immunoglobulin mutation genotype in B cell chronic lymphocytic leukemia," J. Exp. Med., 194(11):1639-1647, Dec. 2001.
Rouet et al., "Introduction of double-strand breaks into the genome of mouse cells by expression of a rare-cutting endonuclease," Mol. Cell Biol., 14(12):8096-106, Dec. 1994.
Sorek et al., "CRISPR-mediated adaptive immune systems in bacteria and archaea," Annu. Rev. Biochem., Jun. 2013.
Starzynska et al., "5T4 oncofetal antigen in gastric carcinoma and its clinical significance," Eur. J. Gatrerol Heptol., 10(6):479-84, Jun. 1998.
Stoddard, "Homing endonuclease structure and function," Q. Rev. Biophys., 38(1):49-95, Feb. 2005.
Studincka et al., "Human-engineered monoclonal antibodies retain full specific binding activity by preserving non-CDR complementarity-modulating residues," Protein Eng., 7(6):805-814, Jun. 1994.
Yamaguchi et al., "NKX2-1/TITF1/TTF-1-Induced ROR1 is required to sustain EGFR survival signaling in lung adenocarcinoma," Cancer Cell, 21(3):348-361, Mar. 2012.
Yun et al., "Targeting of T lymphocytes to melanoma cells through chimeric anti-GD3 immunoglobulin T-cell receptors," Neoplasia., 2(5):449-459, Sep.-Oct. 2000.
Zhang et al., "ROR1 is expressed in human breast cancer and associated with enhanced tumor-cell growth," PLoS One, 7(3):e31127, Mar. 2012.
Zhang et al., "The onco-embryonic antigen ROR1 is expressed by a variety of human cancers," Am. J. Pathol., 181(6):1903-1910, Dec. 2012.
Almagro and Fransson, "Humanization of antibodiesHumanization of antibodies," Frontiers in Bioscience, 13: 1619-33, Jan. 2008.
Banihashenni et al., "Development of specific nanobodies (VHH) for CD19 immuno-targeting of human B-lymphocytes," Iran. J. Basic. Med. Sci., 21(5):455-464, May 2018.
Burgess et al., "Possible dissociation of the heparin-binding and mitogenic activities of heparin-binding (acidic fibroblast) growth factor-1 from its receptor-binding activities by site-directed mutagenesis of a single lysine residue" J. of Cell. Biol., 111(5 Pt 1):2129-2138, Nov. 1990.
Coleman et al., "Effects of amino acid sequence changes on antibody-antigen interactions," Res. Immunol., 145(1):33-36, Jan. 1994.
Ibraginnova and Wade, "Stability of the beta-sheet of the WW domain: A molecular dynamics simulation study," Biophys. J., 77(4):2191-2198, Oct. 1999.
Rudikoff et al., "Single amino acid substitution altering antigen-binding specificity," Proc. Natl. Acad. Sci. U.S.A., 79(6):1979-1983, Mar. 1982.

* cited by examiner

First step screening:

Second step screening:

ROR1 (NTRKR1) SPECIFIC CHIMERIC ANTIGEN RECEPTORS FOR CANCER IMMUNOTHERAPY

CROSS-REFERENCE TO RELATED APPLICATIONS

This application is a National Stage entry of International Application No. PCT/EP2015/067444, filed Jul. 29, 2015, which claims priority to Danish Patent Application No. PA201470465, filed Jul. 29, 2014. The disclosure of the prior applications are hereby incorporated in their entirety by reference.

FIELD OF THE INVENTION

The present invention relates to Chimeric Antigen Receptors (CAR) that are recombinant chimeric proteins able to redirect immune cell specificity and reactivity toward ROR1, a cell surface glycoprotein found on most myeloid cells and used to diagnose chronic lymphocytic leukemia (CLL) or solid tumors such as breast, colon, lung, and kidney tumors in patients. The CARs according to the invention are particularly useful to treat malignant cells bearing ROR1 antigen, when expressed in T-cells or NK cells. The resulting engineered immune cells display high level of specificity toward malignant cells, conferring safety and efficiency for immunotherapy.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). A schematic representation for the 3 generations of CARs is presented in FIG. 1. CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans, where T-cells could be redirected against malignant cells expressing CD19 (June et al., 2011). However, the particular combination of signaling domains, transmembrane and co-stimulatory domains used with respect to CD19 ScFv, was rather antigen-specific and cannot be expanded to any antigen markers.

Chronic lymphocytic leukemia (CLL) is one of the most commonly diagnosed leukemias managed by practicing hematologists. For many years patients with CLL have been viewed as similar, with a long natural history and only marginally effective therapies that rarely yielded complete responses. Recently, several important observations related to the biologic significance of $V_H$ mutational status and associated ZAP-70 overexpression, disrupted p53 function, and chromosomal aberrations have led to the ability to identify patients at high risk for early disease progression and inferior survival. Concurrent with these investigations, several treatments including the nucleoside analogues, monoclonal antibodies rituximab and alemtuzumab have been introduced. Combination of these therapies in clinical trials has led to high complete and overall response rates when applied as initial therapy for symptomatic CLL. Thus, the complexity of initial risk stratification of CLL and treatment has increased significantly. Furthermore, when these initial therapies do not work, approach of the CLL patient with fludarabine-refractory disease can be quite challenging (Byrd J. C et al, 2014).

One candidate antigen of immunotherapies for chronic lymphocytic leukemia (CLL) is Tyrosine-protein kinase transmembrane receptor ROR1 (also called NTRKR1; UniProtKB/TrEMBL) entries: Q01973). ROR1 (The receptor tyrosine kinase-like orphan receptor 1) is a 120-kDa glycoprotein containing an extracellular immunoglobulin (Ig)-like, Kringle, and Frizzled-like cysteine rich domain (FIG. 2). The protein encoded by this gene is a receptor tyrosine kinase that modulates neurite growth in the central nervous system. It is a type I membrane protein and belongs to the ROR subfamily of cell surface receptors (Reddy et al, 1997). Although ROR1 protein expression in patients with CLL with respect to normal leukocytes and its role in the pathobiology of CLL merits further studies. ROR1 may be an appropriate target for cancer immunotherapy (Daneshmanesh et al; 2008). ROR1 is indeed expressed on a variety of B-cell malignancies, but also on subsets of some solid tumors, including breast, colon, lung, and kidney tumors. It is believed that ROR1 functions in oncogenic signaling to promote tumor cell survival in epithelial tumors. Importantly, ROR1 is not expressed on vital organs, except adipose and pancreatic tissue, which reduces potential toxicities from killing of normal cells (Hudecek et al, 2013). ROR1 is expressed during embryogenesis but absent from normal adult tissues, apart from a subset of immature B-cell precursors, and low-level expression on adipocytes (Hudecek et al., 2010; Matsuda et al., 2001). ROR1 was first shown to be expressed in B-cell chronic lymphocytic leukemia (B-CLL) by transcriptional profiling (Klein et al., 2001; Rosenwald et al., 2001) and was subsequently identified on the surface of many cancers including mantle cell lymphoma (MCL), acute lymphoblastic leukemia (ALL) with a t(1;19) chromosome translocation, and a subset of lung, breast, colon, pancreas, renal, and ovarian cancers (Baskar et al., 2008; Bicocca et al., 2012; Daneshmanesh et al., 2008; Dave et al., 2012; Fukuda et al., 2008; Yamaguchi et al., 2012; Zhang et al., 2012a, 2012b). In both lung adenocarcinoma and t(1;19) ALL, ROR1 cooperates in oncogenic signaling and knockdown of ROR1 with siRNA exposed a critical role for this molecule in maintaining tumor cell survival (Bicocca et al., 2012; Choudhury et al., 2010; Gentile et al., 2011; Yamaguchi et al., 2012). Thus, ROR1 loss may not be readily tolerated by tumors making it an attractive candidate for CAR directed T-cell therapy that could be broadly applied.

The present inventors have thus considered that ROR1 could be a valuable target antigen for treating CLL as well as solid tumors such as breast, colon, lung, ovarian and kidney tumors, by using CAR-expressing T cells.

The laboratories of Dr. Stanley Riddell and Dr. Laurence Cooper have previously engineered and validated anti-ROR1 scCARs containing the 4A5 and the 2A2 scFvs, respectively (Cooper et al 2010; Hudecek et al., 2013). In particular, Hudecek et al discloses anti-ROR1 scCARs which contain an IgG4 hinge of diverse length and a CD28 transmembrane domain.

There is still the need for the improvement of CAR functionality by designing CAR architecture and using suitable components since these parameters play a role important and a fine tuning is necessary.

Therefore, as an alternative to the previous strategies, the present invention provides with ROR1 specific CARs, which can be expressed in immune cells to target ROR1 malignant cells with significant clinical advantage. The inventors have found that, by combining CAR architecture to the choice of suitable components, they could obtain specific ROR1 single chain CARs with high cytotoxicity towards cancerous target cells,

SUMMARY OF THE INVENTION

The inventors have generated ROR1 specific CAR having different structure and comprising different scFV derived from different ROR1 specific antibodies.

A ROR1 (NTRKR1) specific chimeric antigen receptor (CAR) according to the present invention may have one of the polypeptide structure selected from V1 to V6 as illustrated in FIG. 4, said structure comprising an extra cellular ligand binding-domain comprising VH and VL from a monoclonal anti-ROR1 antibody, a hinge, a transmembrane domain and a cytoplasmic domain including a CD3 zeta signaling domain and a co-stimulatory domain from 4-1BB.

More particularly, a ROR1 (NTRKR1) specific chimeric antigen receptor (CAR) according to the present invention may have one of the one of the polypeptide structure selected from V3, V5 and V1 as illustrated in FIG. 4, said structure comprising an extra cellular ligand binding-domain comprising VH and VL from a monoclonal anti-ROR1 antibody, a hinge, a CD8α transmembrane domain, a cytoplasmic domain including a CD3 zeta signaling domain and a co-stimulatory domain from 4-1BB. Such ROR1 (NTRKR1) specific antigen receptors have been found to have unexpected superior effects in term of cytotoxicity.

In an embodiment, a ROR1 specific CAR has a structure V1 comprises a FcγRIIIα hinge and CD8α transmembrane domain.

In a preferred embodiment, a ROR1 specific CAR has a structure V3 and comprises a CD8α hinge and a CD8α transmembrane domain.

In another preferred embodiment, a ROR1 specific CAR has a structure V5 comprises an IgG1 hinge and a CD8α transmembrane domain.

In particular, said antigen binding domains (scFvs) derived from H10 and D10 anti-ROR1 antibodies have shown remarkable anticancerous properties.

Moreover, humanized scFvs have been generated from the murine H10 and D10 anti-ROR1 antibodies.

Preferred CAR polypeptides of the invention comprise an amino acid sequence selected from SEQ ID NO. 79 to 138. Following non-specific activation in vitro (e.g. with anti CD3/CD28 coated beads and recombinant IL2), T-cells from donors have been transformed with polynucleotides expressing these CARs using viral transduction. In certain instances, the T-cells were further engineered to create non-alloreactive T-cells, more especially by disruption of a component of TCR (αβ—T-Cell receptors) to prevent Graft versus host reaction. The CAR of the present invention have been found particularly efficient in the context of allogeneic T-cells.

The resulting engineered T-cells displayed reactivity in-vitro against ROR1 positive cells to various extend, showing that the CARs of the present invention contribute to antigen dependent activation, and also proliferation, of the T-cells, making them useful for immunotherapy.

The polypeptides and polynucleotide sequences encoding the CARs of the present invention are detailed in the present specification.

The engineered immune cells of the present invention are particularly useful for therapeutic applications, such as for treating chronic lymphocytic leukemia (CLL), the Small Lymphocytic Lymphoma (SLL), the Mantle Cell Lymphoma (MCL), Acute Lymphoblastic Leukemia (ALL) with a t(1; 19) chromosome translocation. They also can be used for treating solid tumors such as breast, colon, lung, and kidney tumors.

BRIEF DESCRIPTION OF THE FIGURES

Figure 3A:
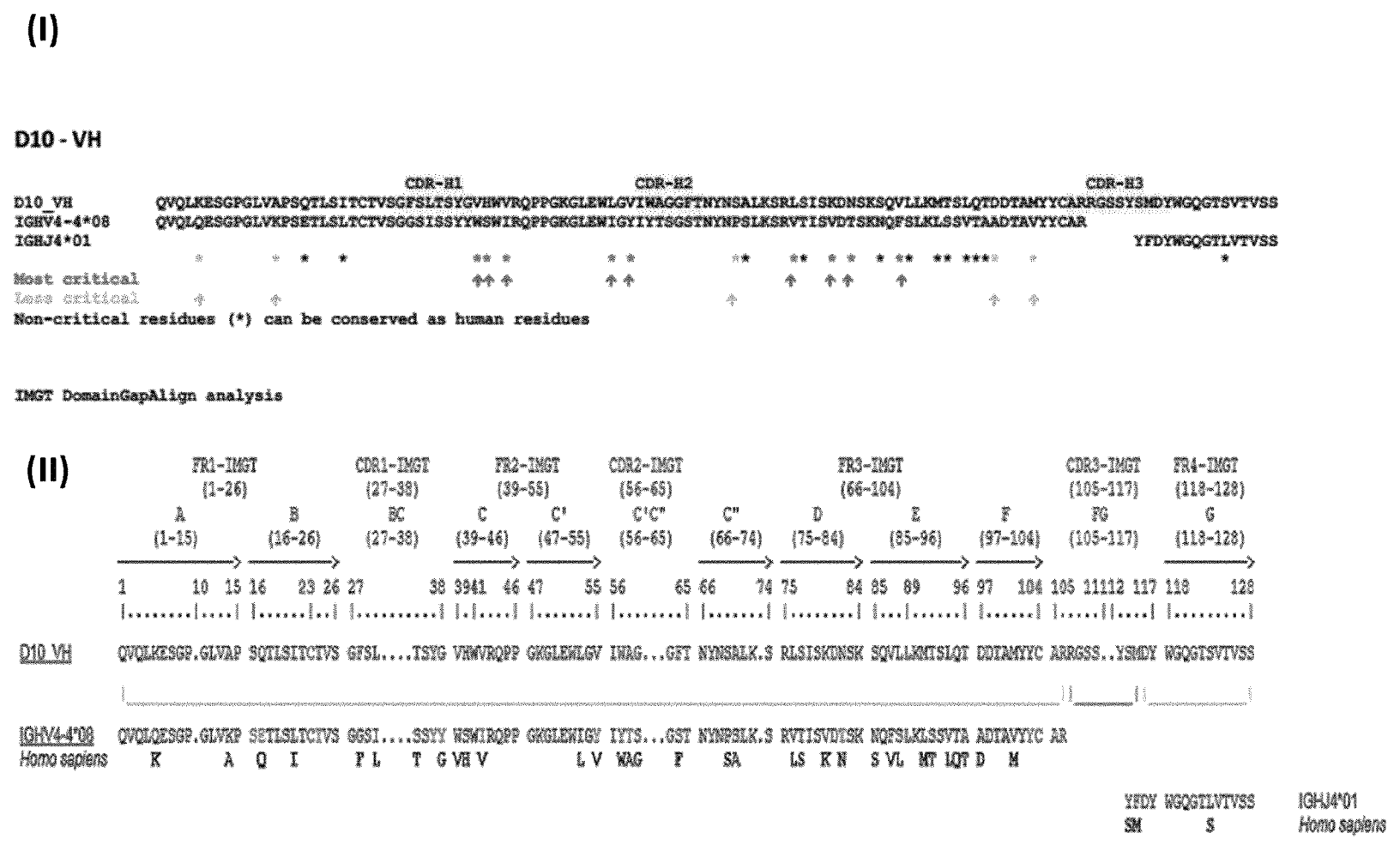
Figure 3B:
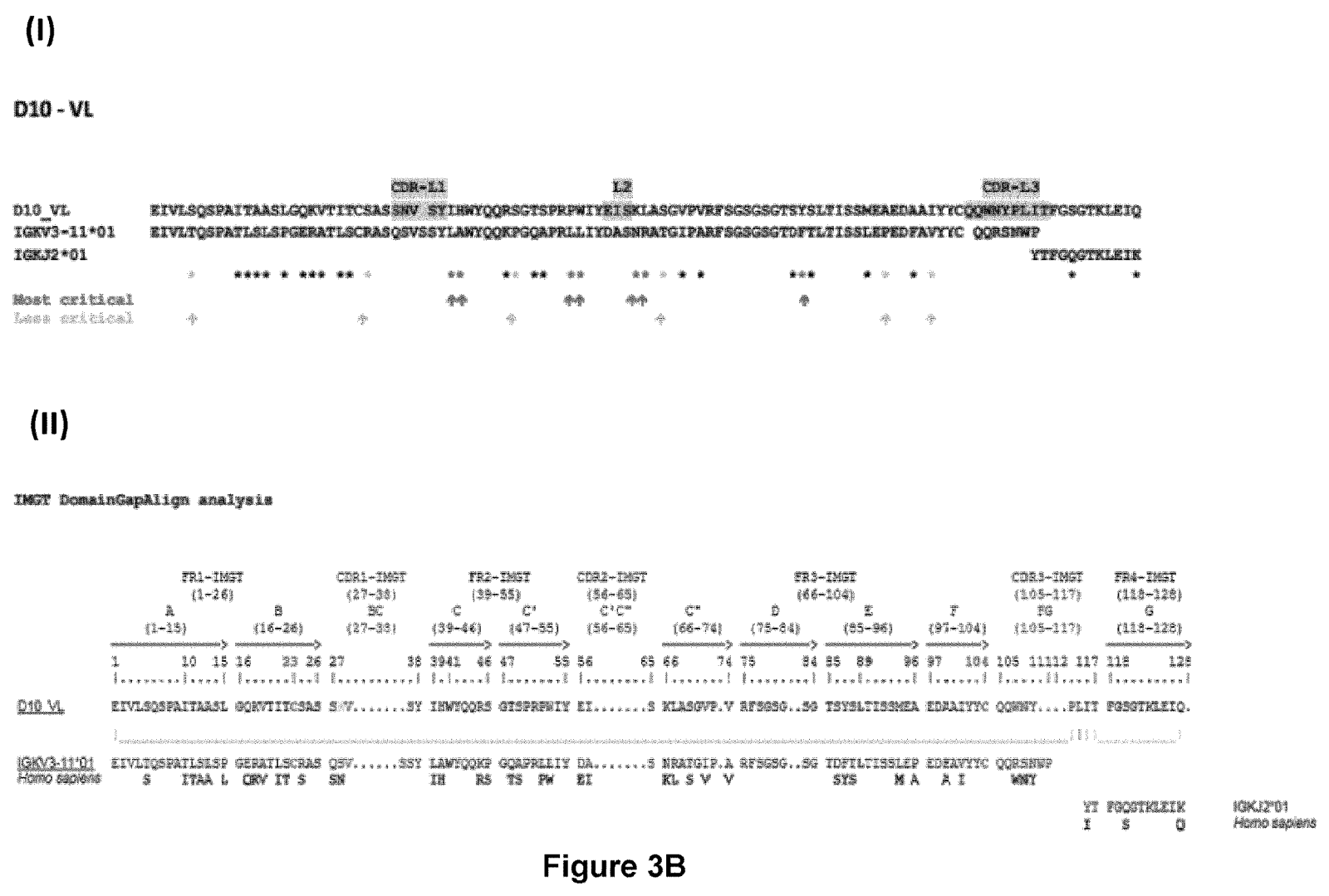
Figure 3C:
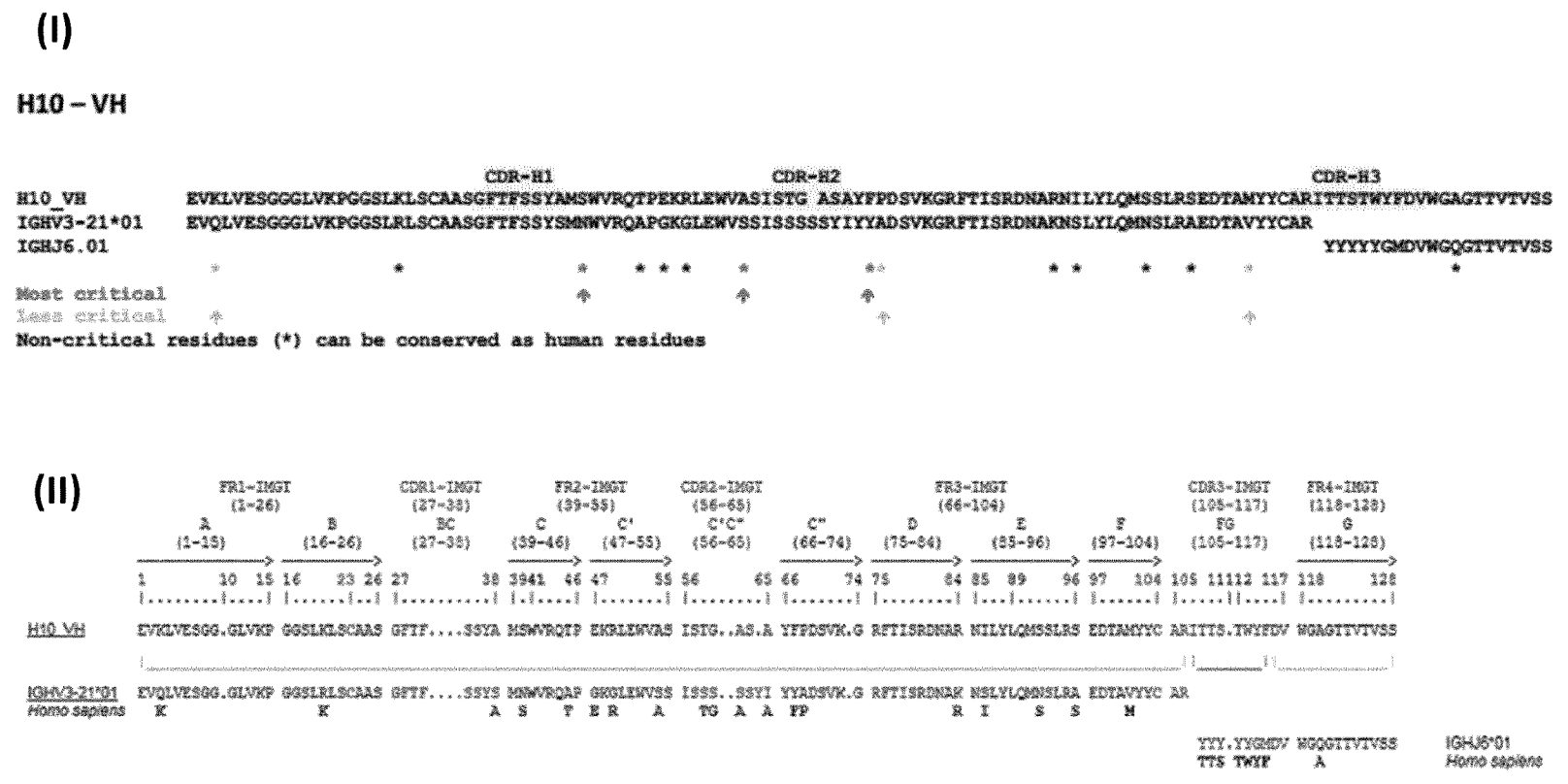
Figure 3D:
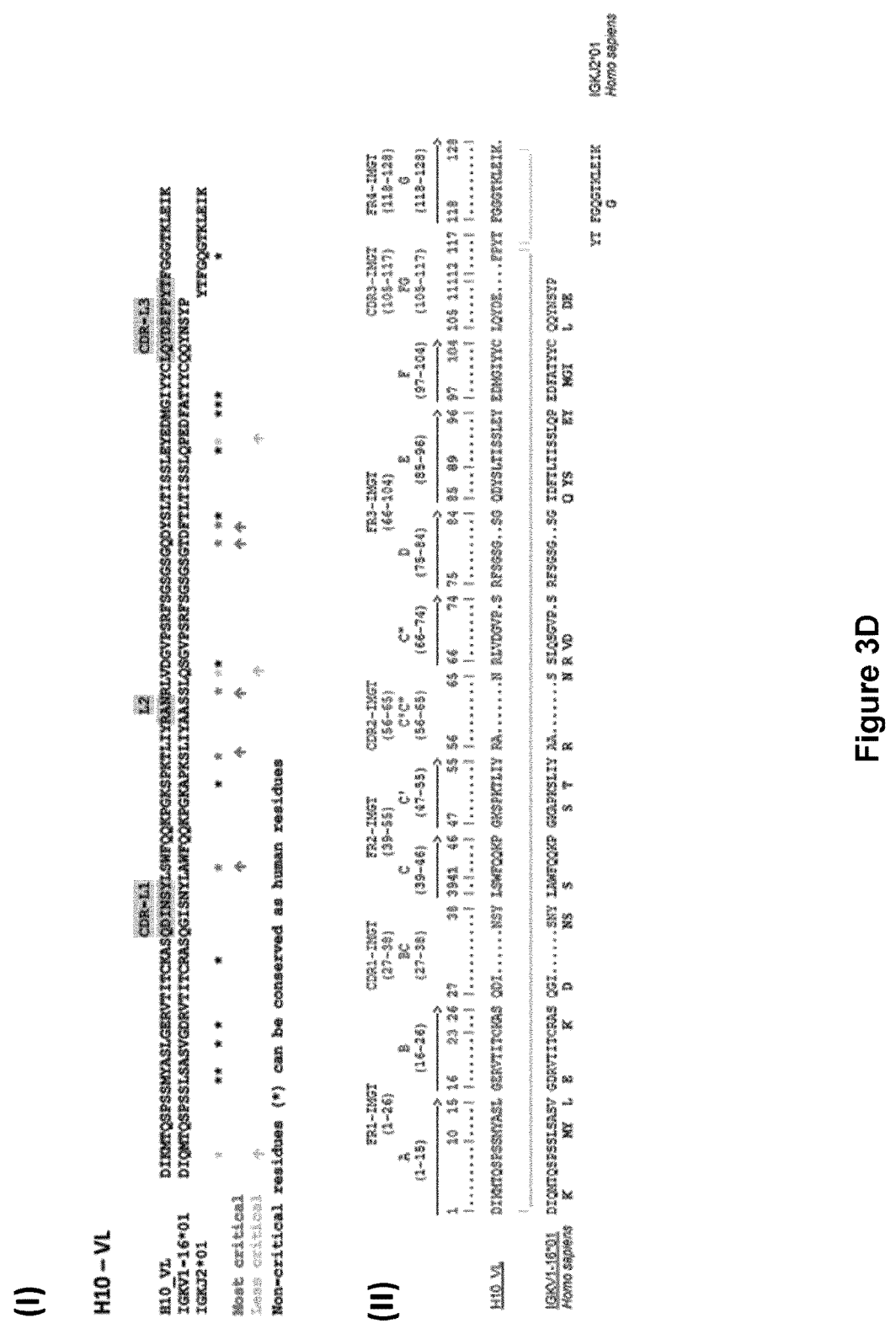

FIGS. 3A, 3B, 3C and 3D: (I) Alignment of sequences from D10 and H10 VH and VL murine sequences with germline human sequences encoded by V and J genes encoding the variable region of immunoglobulins, those sequence sharing high homology with murine sequences. For stability purpose (in particularly of CDRs), "the most critical" positions of AA are shown by arrows in the upper line correspond to AA which should be from murine origin, and the "less critical" ones in the lower line are those which can be either of human or murine origin. (II) MGT/Domain-GapAlign (Lefranc et al. Dev. Comp. Immunol., 29, 185-203 (2005)) allows to align and "IMGT-gap" the domain amino acid sequence of D10 and H10 VH and VL murine sequences. The input sequence is displayed, aligned with the closest germline V-REGION or closest C-DOMAIN of the IMGT domain directory and with gaps according to the IMGT unique numbering for V-REGION, C-DOMAIN and C-LIKE-DOMAIN.

TABLE 1

Figure 1:
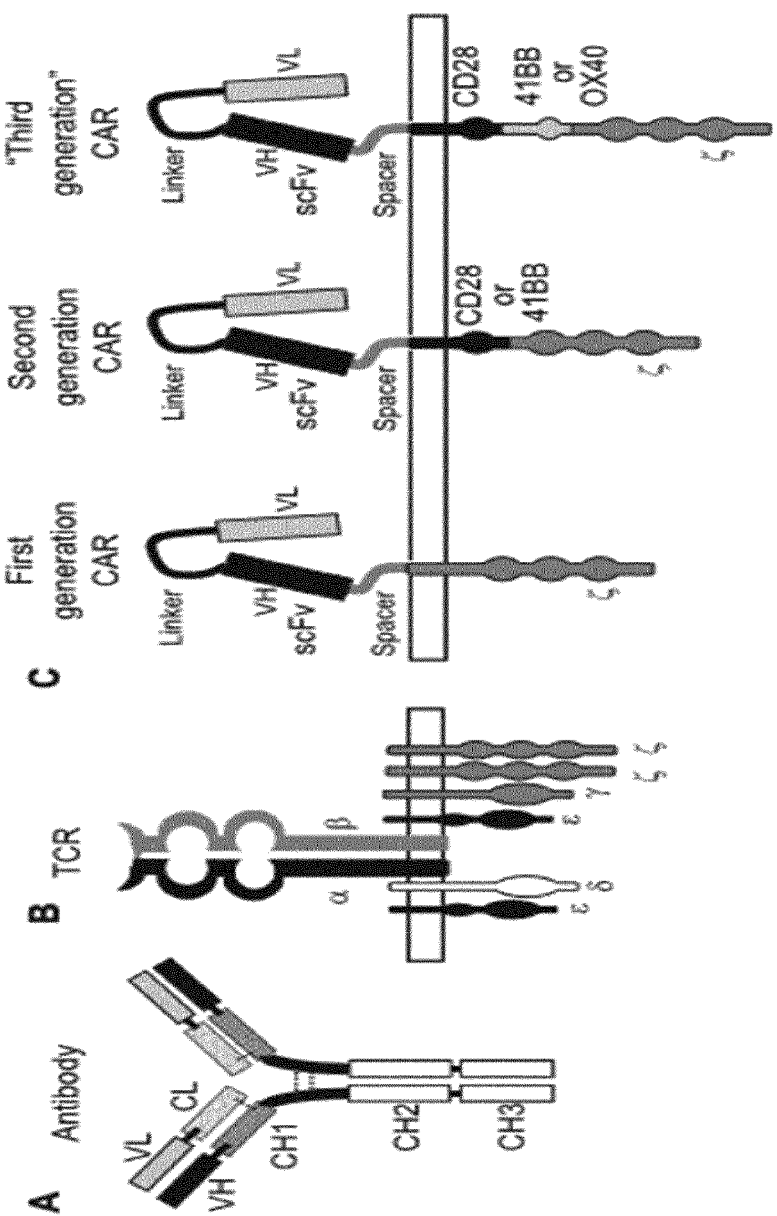
FIG. 1: Single chain chimeric antigen receptors (scCARs) are most commonly created by joining the heavy- and light-chain variable regions of a monoclonal antibody (FIG. 1A) that binds to a specific antigen to the intracellular portion of a T cell signaling molecule, such as components of the TCR-associated CD3 complex (ζ chain) (FIG. 1B). First generation of scars only contain a T cell signaling domain that transmits the activation signal (FIG. 1C left). Second generation scCARs incorporate in addition a single costimulatory molecule endodomain, such as the endodomain of CD28 or 41BB (FIG. 1C middle), that enhances T cell persistence and anti-tumor function in vivo. Third-generation scCARs incorporate at least two costimulatory molecule endodomains, such as the endodomain of CD28 and 41BB (FIG. 1C right).

Sequence of the different CAR components other than scFvs

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| Fcεc | SEQ ID NO. 3 | GLAVSTISSFFPPGYQ |
| CD8α | SEQ ID NO. 4 | TTTPAPRPPTPAPTIASQPLSLRPEACRPAAGGA VHTRGLDFACD |
| IgG1 hinge | SEQ ID NO. 5 | EPKSPDKTHTCPPCPAPPVAGPSVFLFPPKPKDT LMIARTPEVTCVVVDVSHEDPEVKFNWYVDGV EVHNAKTKPREEQYNSTYRVVSVLTVLHQDWL NGKEYKCKVSNKALPAPIEKTISKAKGQPREPQV YTLPPSRDELTKNQVSLTCLVKGFYPSDIAVEWE SNGQPENNYKTTPPVLDSDGSFFLYSKLTVDKSR WQQGNVFSCSVMHEALHNHYTQKSLSLSPGK |
| CD8α | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |
| 41BB intracellular domain | SEQ ID NO. 8 | KRGRKKLLYIFKQPFMRPVQTTQEEDGCSCRFPE EEEGGCEL |
| CD3ζ intracellular domain | SEQ ID NO. 9 | RVKFSRSADAPAYQQGQNQLYNELNLGRREEY DVLDKRRGRDPEMGGKPRRKNPQEGLYNELQK DKMAEAYSEIGMKGERRRGKGHDGLYQGLSTA TKDTYDALHMQALPPR |
| Linker | SEQ ID NO. 10 | GGGGSGGGGSGGGGS |

TABLE 2

Sequence of the scFvs from murine origin, their CDRs of the scFv and humanized scFvs from D10 and H10

| ScFv sequences | SEQ ID # | Raw amino acid sequence |
|---|---|---|
| MURINE ORIGIN | | |
| 2A2 heavy chain variable region | SEQ ID NO. 11 | QVQLQQSGAELVRPGASVTLSCKASGYTFSDYEMHWVIQTPVHGLEWI GAIDPETGGTAYNQKFKGKAILTADKSSSTAYMELRSLTSEDSAVYYCTGY YDYDSFTYWGQGTLVTVSA |
| | SEQ ID NO. 12 | CDR1 GYTFSDYE |
| | SEQ ID NO. 13 | CDR2 IDPETGGT |
| | SEQ ID NO. 14 | CDR3 TGYYDYDSFTY |

TABLE 2-continued

Sequence of the scFvs from murine origin, their CDRs of the scFv and humanized scFvs from D10 and H10

| ScFv sequences | SEQ ID # | Raw amino acid sequence |
| --- | --- | --- |
| 2A2 light chain variable region | SEQ ID NO. 15 | DIVMTQSQKIMSTTVGDRVSITCKASQNVDAAVAWYQQKPGQSPKLLI YSASNRYTGVPDRFTGSGSGTDFTLTISNMQSEDLADYFCQQYDIYPYTF GGGTKLEIK |
| | SEQ ID NO. 16 | CDR1<br>QNVDAA |
| | SEQ ID NO. 17 | CDR2<br>SAS |
| | SEQ ID NO. 18 | CDR3<br>QQYDIYPYT |
| 4A5 heavy chain variable region | SEQ ID NO. 19 | EVKLVESGGGLVKPGGSLKLSCAASGFTFSSYAMSWVRQIPEKRLEWVA SISRGGTTYYPDSVKGRFTISRDNVRNILYLQMSSLRSEDTAMYYCGRYD YDGYYAMDYWGQGTSVTVSS |
| | SEQ ID NO. 20 | CDR1<br>GFTFSSYA |
| | SEQ ID NO. 21 | CDR2<br>ISRGGTT |
| | SEQ ID NO. 22 | CDR3<br>GRYDYDGYYAMDY |
| 4A5 light chain variable region | SEQ ID NO. 23 | DIKMTQSPSSMYASLGERVTITCKASPDINSYLSWFQQKPGKSPKTLIYRA NRLVDGVPSRFSGGGSGQDYSLTINSLEYEDMGIYYCLQYDEFPYTFGGG TKLEMK |
| | SEQ ID NO. 24 | CDR1<br>PDINSY |
| | SEQ ID NO. 25 | CDR2<br>RAN |
| | SEQ ID NO. 26 | CDR3<br>LQYDEFPYT |
| D10 heavy chain variable region | SEQ ID NO. 27 | QVQLKESGPGLVAPSQTLSITCTVSGFSLTSYGVHWVRQPPGKGLEWLG VIWAGGFTNYNSALKSRLSISKDNSKSQVLLKMTSLQTDDTAMYYCARR GSSYSMDYWGQGTSVTVSS |
| | SEQ ID NO. 28 | CDR-H1<br>GFSLTSYG |
| | SEQ ID NO. 29 | CDR-H2<br>IWAGGFT |
| | SEQ ID NO. 30 | CDR-H3<br>ARRGSSYSMDY |
| D10 light chain variable region | SEQ ID NO. 32 | EIVLSQSPAITAASLGQKVTITCSASSNVSYIHWYQQRSGTSPRPWIYEISK LASGVPVRFSGSGSGTSYSLTISSMEAEDAAIYYCQQWNYPLITFGSGTKL EIQ |
| | SEQ ID NO. 33 | CDR-L1<br>SNVSY |
| | SEQ ID NO. 34 | CDR-L2<br>EIS |
| | SEQ ID NO. 35 | CDR-L3<br>QQWNYPLIT |
| G6 heavy chain variable region | SEQ ID NO. 37 | EVQLQQSGPELEKPGASVKISCKASGFAFTGYNMNWVKQTNGKSLEWI GSIDPYYGGSTYNQKFKDKATLTVDKSSSTAYMQLKSLTSDDSAVYYCAR SPGGDYAMDYWGQGTSVTVSS |
| | SEQ ID NO. 38 | CDR1<br>GFAFTGYN |
| | SEQ ID NO. 39 | CDR2<br>IDPYYGGS |
| | SEQ ID NO. 40 | CDR3<br>ARSPGGDYAMDY |
| G6 light chain variable region | SEQ ID NO. 41 | DIKMTQSPSSMYASVGERVTITCKASQGINSYSGWFQQKPGKSPKTLIYR GNRLVDGVPSRFSGSGSGQDYSLTISSLEYEDMGIYYCLQYDEFPYTFGG GTKLEIK |
| | SEQ ID NO. 42 | CDR1<br>QGINSY |
| | SEQ ID NO. 43 | CDR2<br>RGN |
| | SEQ ID NO. 44 | CDR3<br>LQYDEFPYT |
| G3 heavy chain variable region | SEQ ID NO. 45 | QVQLQQPGAELVKPGTSVKLSCKASGYNFTNYWINWVKLRPGQGLEWI GEIYPGSGSTNYNEKFKSKATLTADTSSSTAYMQLSSLASEDSALYYCARD GNYYAMDYWGQGTSVTVSS |

TABLE 2-continued

Sequence of the scFvs from murine origin, their CDRs of the scFv and humanized scFvs from D10 and H10

| ScFv sequences | SEQ ID # | Raw amino acid sequence |
| --- | --- | --- |
| | SEQ ID NO. 46 | CDR1<br>GYNFTNYW |
| | SEQ ID NO. 47 | CDR2<br>IYPGSGST |
| | SEQ ID NO. 48 | CDR3<br>ARDGNYYAMDY |
| G3 light chain variable region | SEQ ID NO. 49 | DIQMTQTTSSLSASLGDRVTITCRASQDINNYLNWYQQKPDGTVKLLIYY<br>TSALHSGVPSRFSGSGSGTDYSLTISNLEQEDIATYFCQQGNTLPPYTFGG<br>GTKLEIK |
| | SEQ ID NO. 50 | CDR1<br>QDINNY |
| | SEQ ID NO. 51 | CDR2<br>YTS |
| | SEQ ID NO. 52 | CDR3<br>QQGNTLPPYT |
| H10 heavy chain variable region | SEQ ID NO. 53 | EVKLVESGGGLVKPGGSLKLSCAASGFTFSSYAMSWVRQTPEKRLEWVA<br>SISTGASAYFPDSVKGRFTISRDNARNILYLQMSSLRSEDTAMYYCARITT<br>STWYFDVWGAGTTVTVSS |
| | SEQ ID NO. 54 | CDR1-H1<br>GFTFSSYA |
| | SEQ ID NO. 55 | CDR-H2<br>ISTGASA |
| | SEQ ID NO. 56 | CDR-H3<br>ARITTSTWYFDV |
| H10 light chain variable region | SEQ ID NO. 58 | DIKMTQSPSSMYASLGERVTITCKASQDINSYLSWFQQKPGKSPKTLIYR<br>ANRLVDGVPSRFSGSGSGQDYSLTISSLEYEDMGIYYCLQYDEFPYTFGG<br>GTKLEIK |
| | SEQ ID NO. 59 | CDR-L1<br>QDINSY |
| | SEQ ID NO. 60 | CDR-L2<br>RAN |
| | SEQ ID NO. 61 | CDR-L3<br>LQYDEFPYT |
| 2A4 heavy chain variable region | SEQ ID NO. 63 | EVKLQQSGPELVKPGASVKISCKTSGYTFTEYTMHWVKQSHGKSLEWIG<br>GINPNNGGTSYNQKFKGKATLTVDKSSSTAYMELRSLTSEDSAVYYCALQ<br>GFAYWGQGTPLTVSS |
| | SEQ ID NO. 64 | CDR1<br>GYTFTEYT |
| | SEQ ID NO. 65 | CDR2<br>INPNNGGT |
| | SEQ ID NO. 66 | CDR3<br>ALQGFAY |
| 2A4 light chain variable region | SEQ ID NO. 67 | MEIEITQTPALMSASPGEKVTMTCSASSSVSYMYWYQQKPRSSPKPWIY<br>LTSNLASGVPARFSGSGSGTSYSLTISSMEAEDAATYYCQQWSSNPYTFG<br>GGTRLELK |
| | SEQ ID NO. 68 | CDR1<br>SSVSY |
| | SEQ ID NO. 69 | CDR2<br>LTS |
| | SEQ ID NO. 70 | CDR3<br>QQWSSNPYT |
| 1C11 heavy chain variable region | SEQ ID NO. 71 | EVKLQESGAELARPGASVKMSCKASGYTFTSYTMHWVKQRPGQGLEWI<br>GYINPSSGYTEYNQKFKDKTTLTADKSSSTAYMQLSSLTSGDSAVYYCAR<br>RVLWLRRGDYWGQGTILTVSA |
| | SEQ ID NO. 72 | CDR1<br>GYTFTSYT |
| | SEQ ID NO. 73 | CDR2<br>INPSSGYT |
| | SEQ ID NO. 74 | CDR3<br>ARRVLWLRRGDY |
| 1C11 light chain variable region | SEQ ID NO. 75 | MEVLITQTPSSLSASLGERVSLTCRASQDIGSSLNWLQQEPDGTIKRLIYA<br>TSSLDSGVPKRFSGSRSGSDYSLTISSLESEDFVDYYCLQYASSPYTFGGGT<br>KLELK |
| | SEQ ID NO. 76 | CDR1<br>QDIGSS |
| | SEQ ID NO. 77 | CDR2<br>ATS |
| | SEQ ID NO. 78 | CDR3 |

TABLE 2-continued

Sequence of the scFvs from murine origin, their CDRs of the scFv and humanized scFvs from D10 and H10

| ScFv sequences | SEQ ID # | Raw amino acid sequence |
|---|---|---|
| | | LQYASSP |

HUMANIZED

| ScFv sequences | SEQ ID # | Raw amino acid sequence |
|---|---|---|
| For the VH chain of D10 antibody Hu D10-VH | SEQ ID NO. 31 | QVQL(Q/K)ESGPGLV(K/A)PSETLSLICTVSGFSLTSYGVHWVRCIPPGK GLEWLGVIWAGGFTNYN(P/S)SLKSRLTISKDNSKNQVSLKLSSVTA(A/D) DTA(V/M)YYCARRGSSYSMDYWGQGTLVTVSS |
| For the VL chain of D10 antibody Hu D10-VL | SEQ ID NO. 36 | EIVL(T/S)QSPATLSLSPGERATLSC(R/S)ASSNVSYIHWYQQK(P/S)GQA PRPWIYEISKLA(T/S)GIPARFSGSGSGTDYTLTISSLE(P/A)EDFA(V/I)YY CQQWNYPLITFGQGTKLEIK |
| For the VH chain of H10 antibody Hu H10-VH | SEQ ID NO. 57 | EV(Q/K)LVESGGGLVKPGGSLRLSCAASGFTFSSYAMSWVRQAPGKGLE WVASISTGASAYF(A/P)DSVKGRFTISRDNAKNSLYLQMNSLRAEDTA(V/M) YYCARITTSTWYFDVWGQGTTVTVSS |
| For the VL chain of H10 antibody Hu H10-VL | SEQ ID NO. 62 | DI(Q/K)MTQSPSSLSASVGDRVTITCRASQDINSYLSWFQQKPGKAPKTL IYRANRL(Q/V)SGVPSRFSGSGSGQDYTLTISSLQ(P/Y)EDFATYYCLQYD EFPYTFGQGTKLEIK |

TABLE 3

CAR of structure V-1

| CAR Designation V-1 | signal peptide (optional) | VH | VL | FcγRIIIα hinge | CD8α-TM | 41BB-IC | CD3ζ CD |
|---|---|---|---|---|---|---|---|
| 2A2-v1 (SEQ ID NO. 79) | SEQ ID NO. 1 | SEQ ID NO. 11 | SEQ ID NO. 15 | SEQ ID NO. 3 | SEQ ID NO. 6 | SEQ ID NO. 8 | SEQ ID NO. 9 |
| 4A5-v1 (SEQ ID NO. 85) | SEQ ID NO. 1 | SEQ ID NO. 19 | SEQ ID NO. 23 | SEQ ID NO. 3 | SEQ ID NO. 6 | SEQ ID NO. 8 | SEQ ID NO. 9 |
| D10-v1-murine & humanized (SEQ ID NO. 91 and 97) | SEQ ID NO. 1 | SEQ ID NO. 27 or 31 | SEQ ID NO. 32 or 36 | SEQ ID NO. 3 | SEQ ID NO. 6 | SEQ ID NO. 8 | SEQ ID NO. 9 |
| G6-v1 (SEQ ID NO. 103) | SEQ ID NO. 1 | SEQ ID NO. 37 | SEQ ID NO. 41 | SEQ ID NO. 3 | SEQ ID NO. 6 | SEQ ID NO. 8 | SEQ ID NO. 9 |
| G3-v1 (SEQ ID NO. 109) | SEQ ID NO. 1 | SEQ ID NO. 45 | SEQ ID NO. 49 | SEQ ID NO. 3 | SEQ ID NO. 6 | SEQ ID NO. 8 | SEQ ID NO. 9 |
| H10-v1 murine & humanized (SEQ ID NO. 115 and 121) | SEQ ID NO. 1 | SEQ ID NO. 53 or 57 | SEQ ID NO. 58 or 62 | SEQ ID NO. 3 | SEQ ID NO. 6 | SEQ ID NO. 8 | SEQ ID NO. 9 |
| 2A4-v1 (SEQ ID NO. 127) | SEQ ID NO. 1 | SEQ ID NO. 63 | SEQ ID NO. 67 | SEQ ID NO. 3 | SEQ ID NO. 6 | SEQ ID NO. 8 | SEQ ID NO. 9 |
| 1C11-v1 (SEQ ID NO. 133) | SEQ ID NO. 1 | SEQ ID NO. 71 | SEQ ID NO. 75 | SEQ ID NO. 3 | SEQ ID NO. 6 | SEQ ID NO. 8 | SEQ ID NO. 9 |

TABLE 4

CAR of structure V-2

| CAR Designation V-2 | signal peptide (optional) | VH | VL | FcγRIIIα hinge | 41BB-TM | 41BB-IC | CD3ζCD |
|---|---|---|---|---|---|---|---|
| 2A2-v2 (SEQ ID NO. 80) | SEQ ID NO. 1 | SEQ ID NO. 11 | SEQ ID NO. 15 | SEQ ID NO. 3 | SEQ ID NO. 7 | SEQ ID NO. 8 | SEQ ID NO. 9 |
| 4A5-v2 (SEQ ID NO. 86) | SEQ ID NO. 1 | SEQ ID NO. 19 | SEQ ID NO. 23 | SEQ ID NO. 3 | SEQ ID NO. 7 | SEQ ID NO. 8 | SEQ ID NO. 9 |
| D10-v2 murine & humanized (SEQ ID NO. 92 and 98) | SEQ ID NO. 1 | SEQ ID NO. 27 or 31 | SEQ ID NO. 32 or 36 | SEQ ID NO. 3 | SEQ ID NO. 7 | SEQ ID NO. 8 | SEQ ID NO. 9 |
| G6-v2 (SEQ ID NO. 104) | SEQ ID NO. 1 | SEQ ID NO. 37 | SEQ ID NO. 41 | SEQ ID NO. 3 | SEQ ID NO. 7 | SEQ ID NO. 8 | SEQ ID NO. 9 |
| G3-v2 (SEQ ID NO. 110) | SEQ ID NO. 1 | SEQ ID NO. 45 | SEQ ID NO. 49 | SEQ ID NO. 3 | SEQ ID NO. 7 | SEQ ID NO. 8 | SEQ ID NO. 9 |
| H10-v2 murine & humanized (SEQ ID NO. 116 and 122) | SEQ ID NO. 1 | SEQ ID NO. 53 or 57 | SEQ ID NO. 58 or 62 | SEQ ID NO. 3 | SEQ ID NO. 7 | SEQ ID NO. 8 | SEQ ID NO. 9 |
| 2A4-v2 (SEQ ID NO. 128) | SEQ ID NO. 1 | SEQ ID NO. 63 | SEQ ID NO. 67 | SEQ ID NO. 3 | SEQ ID NO. 7 | SEQ ID NO. 8 | SEQ ID NO. 9 |
| 1C11-v2 (SEQ ID NO. 134) | SEQ ID NO. 1 | SEQ ID NO. 71 | SEQ ID NO. 75 | SEQ ID NO. 3 | SEQ ID NO. 7 | SEQ ID NO. 8 | SEQ ID NO. 9 |

TABLE 5

CAR of structure V-3

| CAR Designation V-3 | signal peptide (optional) | VH | VL | CD8α hinge | CD8α-TM | 41BB-IC | CD3ζCD |
|---|---|---|---|---|---|---|---|
| 2A2-v3 (SEQ ID NO. 81) | SEQ ID NO. 1 | SEQ ID NO. 11 | SEQ ID NO. 15 | SEQ ID NO. 4 | SEQ ID NO. 6 | SEQ ID NO. 8 | SEQ ID NO. 9 |
| 4A5-v3 (SEQ ID NO. 87) | SEQ ID NO. 1 | SEQ ID NO. 19 | SEQ ID NO. 23 | SEQ ID NO. 4 | SEQ ID NO. 6 | SEQ ID NO. 8 | SEQ ID NO. 9 |
| D10-v3 murine & humanized (SEQ ID NO. 93 and 99)) | SEQ ID NO. 1 | SEQ ID NO. 27 or 31 | SEQ ID NO. 32 or 36 | SEQ ID NO. 4 | SEQ ID NO. 6 | SEQ ID NO. 8 | SEQ ID NO. 9 |
| G6-v3 (SEQ ID NO. 105) | SEQ ID NO. 1 | SEQ ID NO. 37 | SEQ ID NO. 41 | SEQ ID NO. 4 | SEQ ID NO. 6 | SEQ ID NO. 8 | SEQ ID NO. 9 |
| G3-v3 (SEQ ID NO. 111) | SEQ ID NO. 1 | SEQ ID NO. 45 | SEQ ID NO. 49 | SEQ ID NO. 4 | SEQ ID NO. 6 | SEQ ID NO. 8 | SEQ ID NO. 9 |
| H10-v3 murine & humanized (SEQ ID NO. 117 and 123) | SEQ ID NO. 1 | SEQ ID NO. 53 or 57 | SEQ ID NO. 58 or 62 | SEQ ID NO. 4 | SEQ ID NO. 6 | SEQ ID NO. 8 | SEQ ID NO. 9 |
| 2A4-v3 (SEQ ID NO. 129) | SEQ ID NO. 1 | SEQ ID NO. 63 | SEQ ID NO. 67 | SEQ ID NO. 4 | SEQ ID NO. 6 | SEQ ID NO. 8 | SEQ ID NO. 9 |
| 1C11-v3 (SEQ ID NO. 135) | SEQ ID NO. 1 | SEQ ID NO. 71 | SEQ ID NO. 75 | SEQ ID NO. 4 | SEQ ID NO. 6 | SEQ ID NO. 8 | SEQ ID NO. 9 |

TABLE 6

CAR of structure V-4

CAR Structure

| CAR Designation V-4 | signal peptide (optional) | VH | VL | CD8α hinge | 41BB-TM | 41BB-IC | CD3ζCD |
|---|---|---|---|---|---|---|---|
| 2A2-v4 (SEQ ID NO. 82) | SEQ ID NO. 1 | SEQ ID NO. 11 | SEQ ID NO. 15 | SEQ ID NO. 4 | SEQ ID NO. 7 | SEQ ID NO. 8 | SEQ ID NO. 9 |
| 4A5-v4 (SEQ ID NO. 88) | SEQ ID NO. 1 | SEQ ID NO. 19 | SEQ ID NO. 23 | SEQ ID NO. 4 | SEQ ID NO. 7 | SEQ ID NO. 8 | SEQ ID NO. 9 |
| D10-v4 murine & humanized (SEQ ID NO. 94 and 100) | SEQ ID NO. 1 | SEQ ID NO. 27 or 31 | SEQ ID NO. 32 or 36 | SEQ ID NO. 4 | SEQ ID NO. 7 | SEQ ID NO. 8 | SEQ ID NO. 9 |
| G6-v4 (SEQ ID NO. 106) | SEQ ID NO. 1 | SEQ ID NO. 37 | SEQ ID NO. 41 | SEQ ID NO. 4 | SEQ ID NO. 7 | SEQ ID NO. 8 | SEQ ID NO. 9 |
| G3-v4 (SEQ ID NO. 112) | SEQ ID NO. 1 | SEQ ID NO. 45 | SEQ ID NO. 49 | SEQ ID NO. 4 | SEQ ID NO. 7 | SEQ ID NO. 8 | SEQ ID NO. 9 |
| H10-v4 murine & humanized (SEQ ID NO. 118 and 124) | SEQ ID NO. 1 | SEQ ID NO. 53 or 57 | SEQ ID NO. 58 or 62 | SEQ ID NO. 4 | SEQ ID NO. 7 | SEQ ID NO. 8 | SEQ ID NO. 9 |
| 2A4-v4 (SEQ ID NO. 130) | SEQ ID NO. 1 | SEQ ID NO. 63 | SEQ ID NO. 67 | SEQ ID NO. 4 | SEQ ID NO. 7 | SEQ ID NO. 8 | SEQ ID NO. 9 |
| 1C11-v4 (SEQ ID NO. 136) | SEQ ID NO. 1 | SEQ ID NO. 71 | SEQ ID NO. 75 | SEQ ID NO. 4 | SEQ ID NO. 7 | SEQ ID NO. 8 | SEQ ID NO. 9 |

TABLE 7

CAR of structure V-5

CAR Structure

| CAR Designation V-5 | signal peptide (optional) | VH | VL | IgG1 hinge | CD8α-TM | 41BB-IC | CD3ζCD |
|---|---|---|---|---|---|---|---|
| 2A2-v5 (SEQ ID NO. 83) | SEQ ID NO. 1 | SEQ ID NO. 11 | SEQ ID NO. 15 | SEQ ID NO. 5 | SEQ ID NO. 6 | SEQ ID NO. 8 | SEQ ID NO. 9 |
| 4A5-v5 (SEQ ID NO. 89) | SEQ ID NO. 1 | SEQ ID NO. 19 | SEQ ID NO. 23 | SEQ ID NO. 5 | SEQ ID NO. 6 | SEQ ID NO. 8 | SEQ ID NO. 9 |
| D10-v5 murine & humanized (SEQ ID NO. 95 and 101) | SEQ ID NO. 1 | SEQ ID NO. 27 or 31 | SEQ ID NO. 32 or 36 | SEQ ID NO. 5 | SEQ ID NO. 6 | SEQ ID NO. 8 | SEQ ID NO. 9 |
| G6-v5 (SEQ ID NO. 107) | SEQ ID NO. 1 | SEQ ID NO. 37 | SEQ ID NO. 41 | SEQ ID NO. 5 | SEQ ID NO. 6 | SEQ ID NO. 8 | SEQ ID NO. 9 |
| G3-v5 (SEQ ID NO. 113) | SEQ ID NO. 1 | SEQ ID NO. 45 | SEQ ID NO. 49 | SEQ ID NO. 5 | SEQ ID NO. 6 | SEQ ID NO. 8 | SEQ ID NO. 9 |
| H10-v5 murine & humanized (SEQ ID NO. 119 and 125) | SEQ ID NO. 1 | SEQ ID NO. 53 or 57 | SEQ ID NO. 58 or 62 | SEQ ID NO. 5 | SEQ ID NO. 6 | SEQ ID NO. 8 | SEQ ID NO. 9 |
| 2A4-v5 (SEQ ID NO. 131) | SEQ ID NO. 1 | SEQ ID NO. 63 | SEQ ID NO. 67 | SEQ ID NO. 5 | SEQ ID NO. 6 | SEQ ID NO. 8 | SEQ ID NO. 9 |
| 1C11-v5 (SEQ ID NO. 137) | SEQ ID NO. 1 | SEQ ID NO. 71 | SEQ ID NO. 75 | SEQ ID NO. 5 | SEQ ID NO. 6 | SEQ ID NO. 8 | SEQ ID NO. 9 |

TABLE 8

CAR of structure V-6

| CAR Designation V-6 | signal peptide (optional) | VH | VL | IgG1 hinge | 41BB-TM | 41BB-IC | CD3ζCD |
|---|---|---|---|---|---|---|---|
| 2A2-v6 (SEQ ID NO. 84) | SEQ ID NO. 1 | VH | VL | SEQ ID NO. 5 | SEQ ID NO. 7 | SEQ ID NO. 8 | SEQ ID NO. 9 |
| 4A5-v6 (SEQ ID NO. 90) | SEQ ID NO. 1 | SEQ ID NO. 11 | SEQ ID NO. 15 | SEQ ID NO. 5 | SEQ ID NO. 7 | SEQ ID NO. 8 | SEQ ID NO. 9 |
| D10-v6 murine & humanized (SEQ ID NO. 96 and 102) | SEQ ID NO. 1 | SEQ ID NO. 19 | SEQ ID NO. 23 | SEQ ID NO. 5 | SEQ ID NO. 7 | SEQ ID NO. 8 | SEQ ID NO. 9 |
| G6-v6 (SEQ ID NO. 108) | SEQ ID NO. 1 | SEQ ID NO. 27 or 31 | SEQ ID NO. 32 or 36 | SEQ ID NO. 5 | SEQ ID NO. 7 | SEQ ID NO. 8 | SEQ ID NO. 9 |
| G3-v6 (SEQ ID NO. 114) | SEQ ID NO. 1 | SEQ ID NO. 37 | SEQ ID NO. 41 | SEQ ID NO. 5 | SEQ ID NO. 7 | SEQ ID NO. 8 | SEQ ID NO. 9 |
| H10-v6 murine & humanized (SEQ ID NO. 120 and 126) | SEQ ID NO. 1 | SEQ ID NO. 45 | SEQ ID NO. 49 | SEQ ID NO. 5 | SEQ ID NO. 7 | SEQ ID NO. 8 | SEQ ID NO. 9 |
| 2A4-v6 (SEQ ID NO. 132) | SEQ ID NO. 1 | SEQ ID NO. 53 or 57 | SEQ ID NO. 58 or 62 | SEQ ID NO. 5 | SEQ ID NO. 7 | SEQ ID NO. 8 | SEQ ID NO. 9 |
| 1C11-v6 (SEQ ID NO. 138) | SEQ ID NO. 1 | SEQ ID NO. 63 | SEQ ID NO. 67 | SEQ ID NO. 5 | SEQ ID NO. 7 | SEQ ID NO. 8 | SEQ ID NO. 9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

ROR1 Specific Chimeric Antigen Receptors

The present invention relates to new designs of anti-ROR1 chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In a preferred embodiment, said extracellular ligand-binding domain comprises a single chain antibody fragment (scFv) comprising the light ($V_L$) and the heavy ($V_H$) variable fragment of a target antigen specific monoclonal anti CD-123 antibody joined by a flexible linker. Said $V_L$ and $V_H$ are preferably selected from the antibodies referred to as 2A2, 4A5 and D10 as indicated in Table 2.

Moreover, Table 2 referring also to $V_L$ and $V_H$ of G6, G3, H10, 2A4 and 1C11, discloses their respective sequences SEQ ID NO. 37, 41, 45, 49, 53, 58, 63, 67, 71 and 75, as well as humanized $V_L$ and $V_H$ of D10 and H10 of respective sequence SEQ ID NO. 31, 36, 57 and 62.

Figure 4:
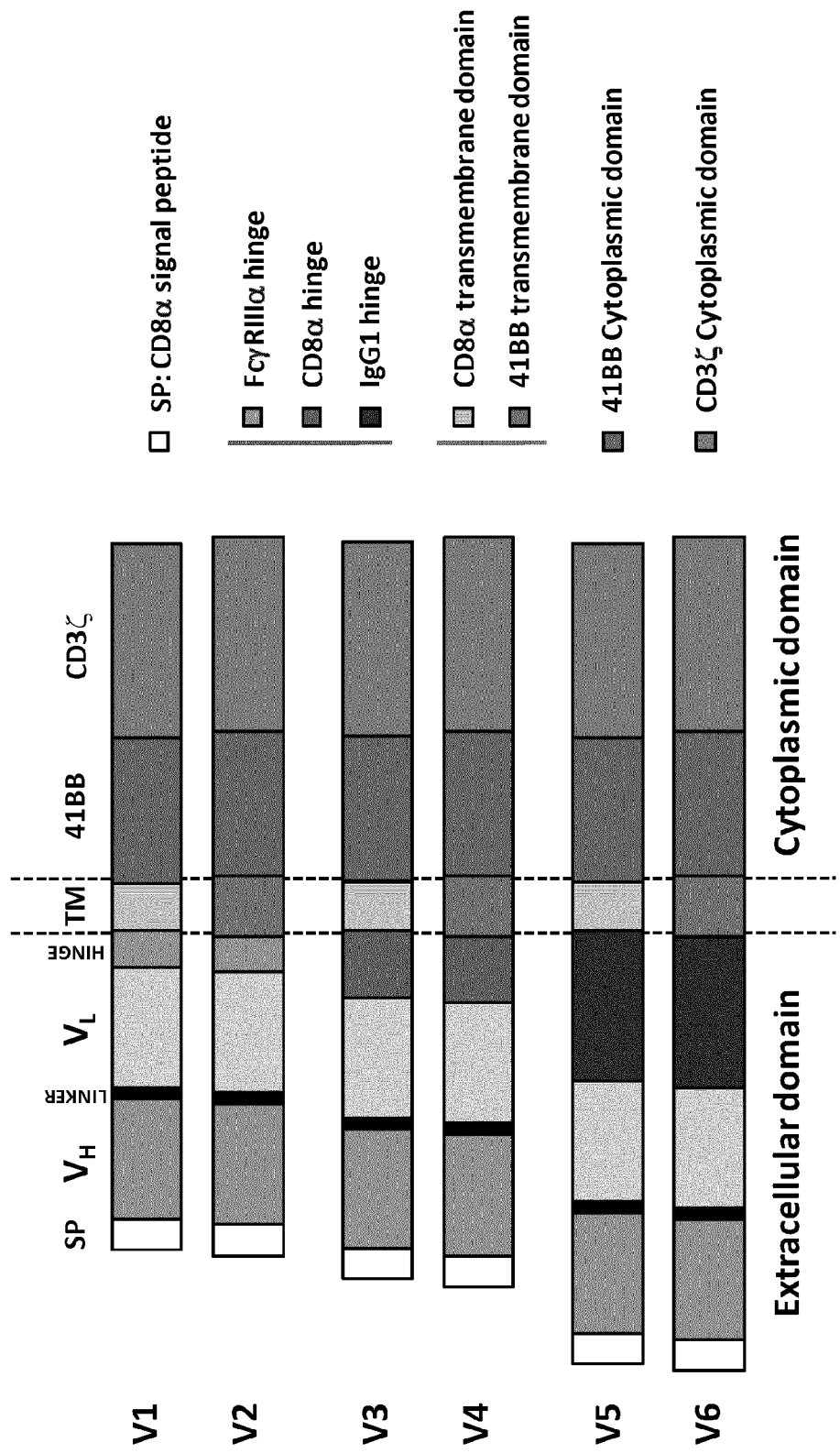
FIG. 4: schematic representation of the different CAR Architecture (V1 to V6).

FIG. 4 shows the architecture of the 6 versions of CARs according to the present invention. Table 1 shows, as examples, the components used in the further experiments.

A ROR1 (NTRKR1) specific chimeric antigen receptor (CAR) according to the present invention may have one of the polypeptide structure selected from V1 to V6 as illustrated in FIG. 4, said structure comprising an extra cellular ligand binding-domain comprising VH and VL from a monoclonal anti-ROR1 antibody, a hinge, a transmembrane domain and a cytoplasmic domain including a CD3 zeta signaling domain and a co-stimulatory domain from 4-1BB.

More specifically, the present invention relates to ROR1 (NTRKR1) specific chimeric antigen receptors (CARs) having one of the polypeptide structure selected from V3, V5 and V1 as illustrated in FIG. 4, said structure comprising an extra cellular ligand binding-domain comprising VH and VL from a monoclonal anti-ROR1 antibody, a hinge, a CD8α transmembrane domain and a cytoplasmic domain including a CD3 zeta signaling domain and a co-stimulatory domain from 4-1BB.

Antigen-Binding Domain

The antigen binding domain of the ROR1 CARs of the invention can be any domain that binds to the off-tissue antigen including but not limited to a monoclonal antibody, a recombinant antibody, a human antibody, a humanized antibody, and a functional fragment thereof.

In a preferred embodiment, said extracellular ligand-binding domain comprises a single chain antibody fragment (scFv) comprising the light ($V_L$) and the heavy ($V_H$) variable fragment of a target antigen specific monoclonal ROR1 antibody joined by a flexible linker. Said $V_L$ and $V_H$ are preferably selected from the antibodies referred to as H10, D10, 4A5, G6, G3, 2A2, 2A4, and 1C11 as indicated in Table 2. They are preferably linked together by a flexible linker comprising for instance the sequence SEQ ID NO:10. In other words, said CARs preferentially comprise an extracellular ligand-binding domain comprising a polypeptide sequence displaying at least 90%, 95% 97% or 99% identity with sequences issued from combinations of VH and VL chains—with a linker between them—as depicted in Table 3 to Table 8 for versions V1 to V6.

In particular preferred embodiments, said $V_L$ and $V_H$ are derived from the antibody H10.

In other particular embodiments, said $V_L$ and $V_H$ are derived from the antibody D10.

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system, and more especially by a T cell transduced with a viral vector comprising a nucleic acid sequence encoding CDR regions of an antibody. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

By the term "humanized antibody" as used herein, is meant the polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 90% humanized, at least about 95% humanized, at least about 98% humanized, or at least about 100% humanized, excluding the complementary-determining regions (CDRs). The antigen-binding polypeptides molecules may be derived from monoclonal antibody donors (e.g., mouse monoclonal antibody donors) and may include CDRs from the monoclonal antibodies (e.g., mouse monoclonal CDRs). When By the term "monoclonal antibody" as used herein, is meant antibody produced by a laboratory-grown cell clone, either of a hybridoma or a virus-transformed lymphocyte, that is more abundant and uniform than natural antibody and is able to bind specifically to a single site on ROR1 antigen. They are monospecific antibodies that are made by identical immune cells that are all clones of a unique parent cell, in contrast to polyclonal antibodies which are made from several different immune cells. Monoclonal antibodies have monovalent affinity, in that they bind to the same epitope.

The present invention discloses a ROR1 specific chimeric antigen receptor (ROR1 CAR) as above, wherein said extra cellular ligand binding-domain comprises VH and VL chains which are humanized.

Table 2 shows the sequences of humanized scFv (VH and VL chains) corresponding to the D10 and H10 anti-ROR1 antibodies.

FIGS. 3A to 3D present the alignments of D10 and H10 scFvs of murine versus their humanized form after having applied the methodology according to Lefranc M P et al (Lefranc, M P, Ehrenmann F, Ginestoux C, Giudicelli V, Duroux P "Use of IMGT (®) databases and tools for antibody engineering and humanization", Methods Mol Biol. 2012; 907: 3-37). In these four alignments are indicated:
  the CDRs,
  the "most critical" amino-acids (AAs) with a upper arrow which mean that those AAs are maintained as murine origin;
  the "less critical" amino-acids with a upper arrow which mean that those AAs can be of murine origin or human origin; it is understood that the humanized sequences of the invention are actually a set of all the different sequences possible made by all the combinations of such "less critical" AAs from human or murine origin; those sequences containing the CDRs and "most critical" AAs as presented just previously.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.).

One aspect of the present invention relates particularly to a ROR1 (NTRKR1) specific chimeric antigen receptor (CAR) having one of the polypeptide structure selected from V3, V5 and V1 as illustrated in FIG. 4, said structure comprising an extra cellular ligand binding-domain comprising VH and VL from a monoclonal anti-ROR1 antibody, a hinge, a CD8α transmembrane domain (CD8α TM) and a cytoplasmic domain including a CD3 zeta signaling domain and a co-stimulatory domain from 4-1BB.

According to a preferred embodiment, said transmembrane domain is encoded by a polypeptide which shares at least 80%, preferably at least 90%, more preferably at least 95%, and even more preferably at least 99% sequence identity with SEQ ID NO. 6 (CD8α TM).

According to another preferred embodiment, said hinge is encoded by a polypeptide which shares at least 80%, preferably at least 90%, more preferably at least 95%, and even more preferably at least 99% sequence identity, respectively for the structures V3, V5 and V1, with SEQ ID NO. 4 (CD8α), SEQ ID NO. 5 (IgG1) and SEQ ID NO. 3 (FcγRIIIα).

According to a more preferred embodiment, the ROR1-specific CAR of the invention has the polypeptide structure V3 comprising a CD8α hinge having the amino acid sequence set forth in SEQ ID NO. 4 and a CD8α transmembrane domain having the amino acid sequence set forth in SEQ ID NO:6.

According to another more preferred embodiment, the ROR1 specific CAR of the invention has the polypeptide structure V5 comprises IgG1 hinge having the amino acid sequence set forth in SEQ ID NO. 5 and a CD8α transmembrane domain having the amino acid sequence set forth in SEQ ID NO. 6.

According to an embodiment, said ROR1 (NTRKR1) specific chimeric antigen receptor (CAR) having one of the polypeptide structure selected from V3, V5 and V1 as illustrated in FIG. 4, wherein the extracellular ligand binding domain comprises:
  a variable heavy chain VH comprising the CDRs from the mouse monoclonal antibody H10 of SEQ ID NO. 54 (CDR-H1), SEQ ID NO:55 (CDR-H2) and SEQ ID NO:56 (CDR-H3), and;
  a variable light VL comprising the CDRs from the mouse monoclonal antibody H10 of SEQ ID NO. 59 (CDR-L1), SEQ ID NO:60 (CDR-L2) and SEQ ID NO:61 (CDR-L3);

or:
  a variable heavy VH comprising the CDRs from the mouse monoclonal antibody D10 of SEQ ID NO. 28 (CDR-H1), SEQ ID NO. 29 (CDR-H2) and SEQ ID NO. 30 (CDR-H3), and;
  a variable light VL comprising the CDRs from the mouse monoclonal antibody D10 of SEQ ID NO. 33 (CDR-L1), SEQ ID NO:34 (CDR-L2) and SEQ ID NO:35 (CDR-L3).

In a preferred embodiment, said ROR1 (NTRKR1) specific chimeric antigen receptor (CAR) having one of the polypeptide structure selected from V3, V5 and V1 as illustrated in FIG. 4, wherein said extra cellular ligand binding-domain comprising VH and VL chains which have at least 80%, preferably at least 90%, more preferably at least 95%, and even more preferably at least 99% sequence identity respectively with
  SEQ ID NO:53 (H10-VH) and SEQ ID NO:58 (H10-VL), or
  SEQ ID NO:27 (D10-VH) and SEQ ID NO:32 (D10-VL), or;

In another embodiment, said ROR1 (NTRKR1) specific chimeric antigen receptor (CAR) having one of the polypeptide structure selected from V3, V5 and V1 as illustrated in FIG. 4, wherein said extra cellular ligand binding-domain comprises VH and VL chains from H10 or D10 antibodies which have been humanized.

In particular, said cellular ligand binding-domain comprises humanized VH and VL chains, wherein,
  a variable heavy Hu H10 VH has a polypeptide encoded by SEQ ID NO: 57, and
  a variable light Hu H10 VH has a polypeptide encoded by SEQ ID NO: 62;
  or:
  a variable heavy Hu D10 VH has a polypeptide encoded by SEQ ID NO: 31, and
  a variable light Hu D10 has a polypeptide encoded by SEQ ID NO: 36.

According to another embodiment, said ROR1 (NTRKR1) specific chimeric antigen receptor (CAR) having one of the polypeptide structure selected from V3, V5 and V1 as illustrated in FIG. 4, wherein said CAR polypeptide shares at least 80%, preferably at least 90%, more preferably at least 95%, and even more preferably at least 99% sequence identity with SEQ ID NO:117 (H10v3-CAR sequence), or with SEQ ID NO:93 (D10v3-CAR sequence), or with SEQ ID NO:95 (D10v5-CAR sequence).

CAR Architectures

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transducing domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs or ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence (SEQ ID NO: 9).

In particular embodiment the signal transducing domain of the CAR of the present invention comprises a co-stimulatory signal molecule or a part of it. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transducing domain of the CAR of the present invention comprises a co-stimulatory signal molecule or a part of it selected from the group consisting of fragment of 4-1BB (GenBank: AAA53133.) and CD28 (NP_006130.1). In particular the signal transducing domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ζ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO. 5, or hinge polypeptides which display preferably at least 80%, more preferably at least 90%, 95% 97% or 99% sequence identity with these polypeptides.

A CAR according to the invention generally further comprises a transmembrane domain (TM) more particularly selected from CD8α and 4-1BB, showing identity with the polypeptides of SEQ ID NO. 6 or 7. The CD8α TM of SEQ ID NO. 6 is preferred.

According to preferred embodiments, the ROR1 specific CAR has a polypeptide structure selected from V3, V5 and V1 as illustrated in FIG. 4, said structure comprising an extra cellular ligand binding-domain comprising VH and VL from a monoclonal anti-ROR1 antibody, a CD8α hinge, a CD8α transmembrane domain, and a cytoplasmic domain including a CD3 zeta signaling domain and a co-stimulatory domain from 4-1BB.

According another preferred embodiment, the ROR1 specific CAR has a polypeptide structure selected from V3, V5 and V1 as illustrated in FIG. 4, said structure comprising an extra cellular ligand binding-domain comprising VH and VL from a monoclonal anti-ROR1 antibody, an IgG1 hinge, a CD8α transmembrane domain and a cytoplasmic domain including a CD3 zeta signaling domain and a co-stimulatory domain from 4-1BB.

According a preferred embodiment, the ROR1 specific CAR has a polypeptide structure selected from V3, V5 and V1 as illustrated in FIG. 4, said structure comprising an extracellular ligand binding-domain comprising VH and VL from a monoclonal anti-ROR1 antibody, a FcγRIIIα hinge, a CD8α transmembrane domain, and a cytoplasmic domain including a CD3 zeta signaling domain and a co-stimulatory domain from 4-1BB.

Tables 3-8 show the CAR structures for all the 6 versions V1 to V6.

Downregulation or mutation of target antigens is commonly observed in cancer cells, creating antigen-loss escape variants. Thus, to offset tumor escape and render immune cell more specific to target, the ROR1 specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

Polynucleotides, Vectors:

The present invention also relates to polynucleotides, vectors encoding the above described CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 or 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering Immune Cells Endowed with CARs:

The present invention encompasses the method of preparing immune cells for immunotherapy comprising introducing ex-vivo into said immune cells the polynucleotides or vectors encoding one of the ROR1 CAR as previously described.

In a preferred embodiment, said polynucleotides are included in lentiviral vectors in view of being stably expressed in the immune cells.

According to further embodiments, said method further comprises the step of genetically modifying said cell to make them more suitable for allogeneic transplantation.

According to a first aspect, the immune cell can be made allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly the risk of graft versus host syndrome and graft rejection is significantly reduced.

According to another aspect, the immune cells can be further genetically engineered to improve their resistance to immunosuppressive drugs or chemotherapy treatments, which are used as standard care for treating ROR1 positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells not endowed with specific ROR1 CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblastic leukemia.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 9.

TABLE 9

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD 223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | INFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Delivery Methods

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptive immune response. Said immune cell according to the present invention can be derived from a stem cell.

The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+T-lymphocytes and CD8+T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with a ROR1 CAR as described above, that do not express functional TCR and that a reactive towards ROR1 positive cells, for their allogeneic transplantation into patients.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohaemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:
(a) providing an immune-cell obtainable by any one of the methods previously described;
(b) Administrating said transformed immune cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed wherein a pre-malignant or malignant cancer condition characterized by ROR1-expressing cells, especially by an overabundance of ROR1-expressing cells. Such conditions are found in hematologic cancers, such as leukemia or malignant lymphoproliferative disorders.

Leukemia can be acute myelogenous leukemia, chronic myelogenous leukemia, myelodysplastic syndrome, acute lymphoid leukemia, chronic lymphoid leukemia, and myelodysplastic syndrome.

Lymphoproliferative disorder can be lymphoma, in particular chronic lymphocytic leukemia, non-Hodgkin's lymphoma, Burkitt's lymphoma, and follicular lymphoma (small cell and large cell).

According to one preferred embodiment, said engineered T cells are provided for the treatment of the Chronic Lymphocytic Leukemia (CLL) or the Small Lymphocytic Lymphoma (SLL).

According to another preferred embodiment, said treatment of CLL or SLL is administered to patients who have been lympho-depleted before the ROR1-CAR-T cell infusion. Said lympho-depletion is performed usually by chemotherapy, and preferably by using drugs as fludarabine (F), cyclophosphamide (C), bendamustine (B) or rituximab (R) or a combination thereof. Typically, the combination of ER or FBR can be used for lympho-depletion prior to CAR-T cell administration.

According to another preferred embodiment, said engineered T cells are provided for the treatment of Mantle Cell Lymphoma (MCL, Acute Lymphoblastic Leukemia (ALL) with a t(1;19) chromosome translocation.

Cancers that may be treated may comprise nonsolid tumors (such as hematological tumors, including but not limited to pre-B ALL (pedriatic indication), adult ALL, mantle cell lymphoma, diffuse large B-cell lymphoma and the like. Types of cancers to be treated with the CARs of the invention include, but are not limited leukemia or lymphoid malignancies. Adult tumors/cancers and pediatric tumors/cancers are also included.

Also, solid tumors such as breast, colon, lung, and kidney tumors can be treated by the CARs of the invention. Also, the engineered T cells of the invention can be used as a treatment of pancreas, renal or ovarian cancers.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

OTHER DEFINITIONS

Unless otherwise specified, "a," "an," "the," and "at least one" are used interchangeably and mean one or more than one. Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against ROR1 antigen and can comprise as non-limiting example the amino acid sequences: SEQ ID NO: 79 to 138.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Custom-made TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BILA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

General Method

Primary Cells Peripheral blood mononuclear cells were isolated by density gradient centrifugation from buffy coats from healthy volunteer donors (Etablissement Français du Sang). T lymphocytes were then purified using the EasySep human T cell enrichment kit (Stemcell Technologies), and activated with Dynabeads Human T-Activator CD3/CD28 (Life Technologies) in X-vivo 15 medium (Lonza) supplemented with 20 ng/ml IL-2 (Miltenyi) and 5% human AB serum (Seralab).

Cell Lines

The K562, Jeko-1, MDA-MB-231, PC-3 and MCF-7 cell lines were obtained from the American Type Culture Collection. K562 cells were cultured in IMDM supplemented with 10% heat-inactivated FCS, 2 mmol/L L-glutamine and 100 units/ml penicillin, and 100 µg/mL streptomycin. Jeko-1 cells were cultured in RPMI 1640 supplemented with 20% heat-inactivated FCS, 2 mmol/L L-glutamine and 100 units/ml penicillin, and 100m/mL streptomycin. MDA-MB-231 cells were cultured in DMEM supplemented with 10% heat-inactivated FCS, 2 mmol/L L-glutamine and 100 units/ml penicillin, and 100 µg/mL streptomycin. PC-3 cells were cultured in F-12K supplemented with 10% heat-inactivated FCS, 2 mmol/L L-glutamine and 100 units/ml penicillin, and 100 µg/mL streptomycin. MCF-7 cells were cultured in DMEM supplemented with 10% heat-inactivated FCS, 2 mmol/L L-glutamine and 100 units/ml penicillin, and 100m/mL streptomycin and 0.01 mg/ml human insulin.

Quantification of ROR1 Cell Surface Expression

The number of ROR1 surface molecules on different human cell lines was determined by saturation binding using the monoclonal anti-ROR1 antibody clone 2A (Miltenyi) and the Dako QiFIKIT according to the manufacturer's instructions.

Synthesis of DNA Encoding scCARs

The DNA encoding the scCARs was synthesized by GenScript.

Construction of In Vitro Transcription mRNA Vectors for scCARs

The DNA encoding the scCARs was cloned in the plasmid pCLS9632 between the T7 promoter and the BGH poly A.

RNA In Vitro Transcription mRNA encoding the scCAR were in vitro transcribed and polyadenylated using the mMessage mMachine T7 Ultra kit (Life technologies) following the manufacturer's instructions. RNAs were purified with RNeasy columns (Qiagen), eluted in cytoporation medium T (Harvard Apparatus), and quantified by measuring absorbance at 260 nm using a Nanodrop ND-1000 spectrophotometer. Quality of the RNA was verified on a denaturing formaldehyde/MOPS agarose gel.

RNA Electroporation of T Cells 4-5 days or 11-12 post-activation, T lymphocytes were transfected by electrotransfer of messenger RNA using an AgilePulse MAX system (Harvard Apparatus). I. $5 \times 10^6$ cells were mixed with 15 µg of the mRNA encoding the scCAR into a 0.4 cm cuvette. The electroporation was performed according to the protocol set forth in WO2013176915. Following electroporation, cells were diluted into culture medium and incubated at 37° C./5% $CO_2$.

Detection of scCAR

By flow cytometry: The T cells were stained with PE-labeled polyclonal goat anti-mouse $(Fab)_2$ antibodies (Jackson Immunoresearch) or biotin-labeled protein L (GenScript) followed by phycoerythrin-labeled streptavidin (BD pharmingen), and finally analysed using the MACSQuant flow cytometer (Miltenyi).

By Western blotting: $1 \times 10^6$ T cells were lysed in 50 µl RIPA buffer containing 1 mM orthovanadate, 3 µg/ml of protease inhibitor and 2 mM of PMSF. Cells lysates were separated by SDS-PAGE on a Any kD™ acrylamide gel (BioRad). After transfer to a nitrocellulose membrane, this was incubated with a mouse anti-human CD3z (pharmingen) and then with a goat anti-mouse IgG horseradish peroxidase-conjugated antibody (Sigma). Antibody binding was revealed by using the ECL kit (Pierce).

Degranulation Assay $5 \times 10^4$ T cells were co-cultured with $5 \times 10^4$ ROR1-positive or ROR1-negative cells in 0.1 ml per well in a 96-well plate. APC-labeled anti-CD107a (BD Biosciences) was added at the beginning of the co-culture in addition to 1 µg/ml of anti-CD49d (BD Biosciences), 1 µg/ml of anti-CD28 (Miltenyi), and 1× Monensin solution (eBioscience). After a 6h incubation, the cells were stained with a fixable viability dye (eBioscience) and vioblue-labeled anti-CD8 (Miltenyi) and analyzed using the MACSQuant flow cytometer (Miltenyi). Degranulating cytotoxic T cells correspond to CD8+ CD107a+ cells.

Cytokine Release Assay $5 \times 10^4$ T cells were co-cultured with $5 \times 10^4$ ROR1-positive or ROR1-negative cells in 0.1 ml per well in a 96-well plate. After a 24 hours incubation, the culture supernatants were collected and analysed for IFNγROR1-positive or ROR1-negative cells.

Cytotoxicity Assay

With Adherent Target Cells:

$2 \times 10^4$ ROR1-positive or ROR1-negative cells were seeded in 0.1 ml per well in a 96 well plate. The day after the plating, the ROR1-positive and the ROR1-negative cells were labeled with CellTrace CFSE and co-cultured with $4 \times 10^5$ T cells for 4 hours. The cells were then harvested, stained with a fixable viability dye (eBioscience) and analyzed using the MACSQuant flow cytometer (Miltenyi).

The percentage of specific lysis was calculated using the following formula:

$$\% \text{ cell lysis} = 100\% - \frac{\frac{\% \text{ viable target cells upon coculture with CAR modified } T \text{ cells}}{\% \text{ viable control cells upon coculture with modified } T \text{ cells}}}{\frac{\% \text{ viable target cells upon coculture with non modified } T \text{ cells}}{\% \text{ viable control cells upon coculture with non modified } T \text{ cells}}}$$

With Suspension Target Cells:

ROR1-positive and ROR1-negative cells were respectively labeled with CellTrace CFSE and CellTrace Violet. About $2 \times 10^4$ ROR1-positive cells were co-cultured with $2 \times 10^4$ ROR1negative cells with $4 \times 10^5$ T cells in 0.1 ml per well in a 96-well plate. After a 4 hours incubation, the cells were harvested and stained with a fixable viability dye (eBioscience) and analyzed using the MACSQuant flow cytometer (Miltenyi).

The percentage of specific lysis was calculated using the previous formula.

EXAMPLES

Examples of CAR Polypeptide Sequences:

Hereafter, the sequences SEQ ID NO. 79 to 138 (with peptide signal) of 60 ROR1 scCARs are presented. These have CAR architecture of V1 to V6, and scFvs from 8 different antibodies: 2A2, 4A5, D10, G6, G3, H10, 2A4 and 1C11.

The versions V1, V3 and V5 (scCARs with the CD8α transmembrane domain) were assayed in the following experiments excepted for the scCAR with the 2A2 scFvs, for which only the V1 version was tested (as benchmark for comparison), this one having the same structure as described by Hudecek et al (2013).

Framed sequences correspond to preferred VH and VL sequences. However, VH and VL may be swapped to improve CAR efficiency according to the invention.

2A2 v1

(SEQ ID NO. 1 + SEQ ID NO. 79)

MALPVTALLLPLALLLHAARP QVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSA GGGGSGGGGSGG

GGS DIVMTQSQKIMSTTVGDRVSITCKASQNVDAAVAWYQQKPGQSPKLLIYSASNRYTGVPDRFTGSGSGTDFT

LTISNMQSEDLADYFCQQYDIYPYTFGGGTKLEIK GLAVSTISSFFPPGYQIYIWAPLAGTCGVLLLSLVITLYCKRGRK

KLLYIFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKDTYDALHMQALPPR

2A2 v2

(SEQ ID NO. 1 + SEQ ID NO. 80)

MALPVTALLLPLALLLHAARP QVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSA GGGGSGGGGSGG

GGS DIVMTQSQKIMSTTVGDRVSITCKASQNVDAAVAWYQQKPGQSPKLLIYSASNRYTGVPDRFTGSGSGTDFT

LTISNMQSEDLADYFCQQYDIYPYTFGGGTKLEIK GLAVSTISSFFPPGYQIISFFLALTSTALLFLLFFLTLRFSVVKRGR

KKLLYIFKQPFMRPVQTTQEEDGCSCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKGHDGLYQGLSTATKDTYDALHMQALPP

R

2A2 v3
(SEQ ID NO. 1 + SEQ ID NO. 81)
MALPVTALLLPLALLLHAARPQVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSAGGGGSGGGGSGG

GGSDIVMTQSQKIMSTTVGDRVSITCKASQNVDAAVAWYQQKPGQSPKLLIYSASNRYTGVPDRFTGSGSGTDFT

LTISNMQSEDLADYFCQQYDIYPYTFGGGTKLEIKTTTPAPRPPTPAPTIASQPLSLRPEACRPAAGGAVHTRGLDFA

CDIYIWAPLAGTCGVLLLSLVITLYCKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR

2A2 v4
(SEQ ID NO. 1 + SEQ ID NO. 82)
MALPVTALLLPLALLLHAARPQVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSAGGGGSGGGGSGG

GGSDIVMTQSQKIMSTTVGDRVSITCKASQNVDAAVAWYQQKPGQSPKLLIYSASNRYTGVPDRFTGSGSGTDFT

LTISNMQSEDLADYFCQQYDIYPYTFGGGTKLEIKTTTPAPRPPTPAPTIASQPLSLRPEACRPAAGGAVHTRGLDFA

CDIISFFLALTSTALLFLLFFLTLRFSVVKRGRKKLLYIFKQPFMRPVQTTQEEDGCSCRFPEEEEGGCELRVKFSRSADA

PAYQQGQNQLYNELNLGRREEYDVLDKRRGRDPEMGGKPRRKNPQEGLYNELQKDKMAEAYSEIGMKGERRRG

KGHDGLYQGLSTATKDTYDALHMQALPPR

2A2 v5
(SEQ ID NO. 1 + SEQ ID NO. 83)
MALPVTALLLPLALLLHAARPQVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSAGGGGSGGGGSGG

GGSDIVMTQSQKIMSTTVGDRVSITCKASQNVDAAVAWYQQKPGQSPKWYSASNRYTGVPDRFTGSGSGTDFT

LTISNMQSEDLADYFCQQYDIYPYTFGGGTKLEIKEPKSPDKTHTCPPCPAPPVAGPSVFLFPPKPKDTLMIARTPEV

TCVVVDVSHEDPEVKFNWYVDGVEVHNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGKIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR

2A2 v6
(SEQ ID NO. 1 + SEQ ID NO. 84)
MALPVTALLLPLALLLHAARPQVQLQQSGAELVRPGASVTLSCKASGYTFSDYEMHWVIQTPVHGLEWIGAIDPET

GGTAYNQKFKGKAILTADKSSSTAYMELRSLTSEDSAVYYCTGYYDYDSFTYWGQGTLVTVSAGGGGSGGGGSGG

GGSDIVMTQSQKIMSTTVGDRVSITCKASQNVDAAVAWYQQKPGQSPKWYSASNRYTGVPDRFTGSGSGTDFT

LTISNMQSEDLADYFCQQYDIYPYTFGGGTKLEIKEPKSPDKTHTCPPCPAPPVAGPSVFLFPPKPKDTLMIARTPEV

TCVVVDVSHEDPEVKFNWYVDGVEVHNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGKIISFFLALTSTALLFLLFFLTLRFSVVKRGRKKLLYIFKQPFMR

PVQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKHDGLYQGLSTATKDTYDALHMQALPPR

4A5 v1
(SEQ ID NO. 1 + SEQ ID NO. 85)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVIVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKHDGLYQGLSTATKDTYDALHMQALPPR

4A5 v2
(SEQ ID NO. 1 + SEQ ID NO. 86)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVTVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKGLAVSTISSFFPPGYQIISFFLALTSTALLFLLFFLTLRFSVVKRGRK

KLLYIFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKHDGLYQGLSTATKDTYDALHMQALPPR

4A5 v3
(SEQ ID NO. 1 + SEQ ID NO. 87)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVTVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKTTTPAPRPPTPAPTIASQPLSLRPEACRPAAGGAVHTRGLDFAC

DIYIWAPLAGTCGVLLLSLVITLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGERRRGKG

HDGLYQGLSTATKDTYDALHMQALPPR

4A5 v4
(SEQ ID NO. 1 + SEQ ID NO. 88)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVTVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKTTTPAPRPPTPAPTIASQPLSLRPEACRPAAGGAVHTRGLDFAC

```
DIISFFLALTSTALLFLLFFLTLRFSVVKRGRKKLLYIFKQPFMRPVQTTQEEDGCSCRFPEEEEGGCELRVKFSRSADAP
AYQQGQNQLYNELNLGRREEYDVLDKRRGRDPEMGGKPRRKNPQEGLYNELQKDMAEAYSEIGMKGERRRGK
GHDGLYQGLSTATKDTYDALHMQALPPR

4A5 v5
                                                          (SEQ ID NO. 1 + SEQ ID NO. 89)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVTVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDMAEAYSEIGMKGERRRGKGHDGLYQGLSTATKDTYDALHMQALPPR

4A5 v6
                                                          (SEQ ID NO. 1 + SEQ ID NO. 90)
MALPVTALLLPLALLLHAARPEVKLVESGGGLVKPGGSLKLSCAASGFTFSSYAMSWVRQIPEKRLEWVASISRGGT

TYYPDSVKGRFTISRDNVRNILYLQMSSLRSEDTAMYYCGRYDYDGYYAMDYWGQGTSVTVSSGGGGSGGGGSG

GGGSDIKMTQSPSSMYASLGERVTITCKASPDINSYLSWFQQKPGKSPKTLIYRANRLVDGVPSRFSGGGSGQDYSL

TINSLEYEDMGIYYCLQYDEFPYTFGGGTKLEMKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIISFFLALTSTALLFLLFFLTLRFSVVKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDMAEAYSEIGMKGERRRGKGHDGLYQGLSTATKDTYDALHMQALPPR

D10 v1
                                                          (SEQ ID NO. 1 + SEQ ID NO. 91)
MALPVTALLLPLALLLHAARPQVQLKESGPGLVAPSQTLSITCTVSGFSLTSYGVHWVRQPPGKGLEWLGVIWAGG

FTNYNSALKSRLSISKDNSKSQVLLKMTSLQTDDTAMYYCARRGSSYSMDYWGQGTSVTVSSGGGGSGGGGSGG

GGSEIVLSQSPAITAASLGQKVTITCSASSNVSYIHWYQQRSGTSPRPWIYEISKLASGVPVRFSGSGSGTSYSLTISSM

EAEDAAIYYCQQWNYPLITFGSGTKLEIQGLAVSTISSFFPPGYQIYIWAPLAGTCGVLLLSLVITLYCKRGRKKLLYIFK

QPFMRPVQTTQEEDGCSCRFPEEEEGGCELRVKFSRSADAPAYQQGQNQLYNELNLGRREEYDVLDKRRGRDPE

MGGKPRRKNPQEGLYNELQKDMAEAYSEIGMKGERRRGKGHDGLYQGLSTATKDTYDALHMQALPPR

D10 v2
                                                          (SEQ ID NO. 1 + SEQ ID NO. 92)
MALPVTALLLPLALLLHAARPQVQLKESGPGLVAPSQTLSITCTVSGFSLTSYGVHWVRQPPGKGLEWLGVIWAGG

FTNYNSALKSRLSISKDNSKSQVLLKMTSLQTDDTAMYYCARRGSSYSMDYWGQGTSVTVSSGGGGSGGGGSGG
```

GGS`EIVLSQSPAITAASLGQKVTITCSASSNVSYIHWYQQRSGTSPRPWIYEISKLASGVPVRFSGSGSGTSYSLTISSM`

`EAEDAAIYYCQQWNYPLITFGSGTKLEIQ`GLAVSTISSFFPPGYQIISFFLALTSTALLFLLFFLTLRFSVVKRGRKKLLYIF

KQPFMRPVQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPPR

D10 v3
(SEQ ID NO. 1 + SEQ ID NO. 93)
MALPVTALLLPLALLLHAAR`PQVQLKESGPGLVAPSQTLSITCTVSGFSLTSYGVHWVRQPPGKGLEWLGVIWAGG`

`FTNYNSALKSRLSISKDNSKSQVLLKMTSLQTDDTAMYYCARRGSSYSMDYWGQGTSVTVSS`GGGGSGGGGSGG

GGS`EIVLSQSPAITAASLGQKVTITCSASSNVSYIHWYQQRSGTSPRPWIYEISKLASGVPVRFSGSGSGTSYSLTISSM`

`EAEDAAIYYCQQWNYPLITFGSGTKLEIQ`TTTPAPRPPTPAPTIASQPLSLRPEACRPAAGGAVHTRGLDFACDIYIW

APLAGTCGVLLLSLVITLYCKRGRKKLLYIFKQPFMRPVQTTQEEDGCSCRFPEEEEGGCELRVKFSRSADAPAYQQG

QNQLYNELNLGRREEYDVLDKRRGRDPEMGGKPRRKNPQEGLYNELQKDKMAEAYSEIGMKGERRRGKGHDGL

YQGLSTATKDTYDALHMQALPPR

D10 v4
(SEQ ID NO. 1 + SEQ ID NO. 94)
MALPVTALLLPLALLLHAAR`PQVQLKESGPGLVAPSQTLSITCTVSGFSLTSYGVHWVRQPPGKGLEWLGVIWAGG`

`FTNYNSALKSRLSISKDNSKSQVLLKMTSLQTDDTAMYYCARRGSSYSMDYWGQGTSVIVSS`GGGGSGGGGSGG

GGS`EIVLSQSPAITAASLGQKVTITCSASSNVSYIHWYQQRSGTSPRPWIYEISKLASGVPVRFSGSGSGTSYSLTISSM`

`EAEDAAIYYCQQWNYPLITFGSGTKLEIQ`TTTPAPRPPTPAPTIASQPLSLRPEACRPAAGGAVHTRGLDFACDIISFF

LALTSTALLFLLFFLTLRFSVVKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR

D10 v5
(SEQ ID NO. 1 + SEQ ID NO. 95)
MALPVTALLLPLALLLHAAR`PQVQLKESGPGLVAPSQTLSITCTVSGFSLTSYGVHWVRQPPGKGLEWLGVIWAGG`

`FTNYNSALKSRLSISKDNSKSQVLLKMTSLQTDDTAMYYCARRGSSYSMDYWGQGTSVTVSS`GGGGSGGGGSGG

GGS`EIVLSQSPAITAASLGQKVTITCSASSNVSYIHWYQQRSGTSPRPWIYEISKLASGVPVRFSGSGSGTSYSLTISSM`

`EAEDAAIYYCQQWNYPLITFGSGTKLEIQ`EPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGKIYIWAPLAGTCGVLLLSLVITLYCKRGRKKLLYIFKQPFMRPVQTTQEE

DGCSCRFPEEEEGGCELRVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR

D10 v6
(SEQ ID NO. 1 + SEQ ID NO. 96)
MALPVTALLLPLALLLHAAR`PQVQLKESGPGLVAPSQTLSITCTVSGFSLTSYGVHWVRQPPGKGLEWLGVIWAGG`

`FTNYNSALKSRLSISKDNSKSQVLLKMTSLQTDDTAMYYCARRGSSYSMDYWGQGTSVTVSS`GGGGSGGGGSGG

GGS[EIVLSQSPAITAASLGQKVTITCSASSNVSYIHWYQQRSGTSPRPWIYEISKLASGVPVRFSGSGSGTSYSLTISSM

EAEDAAIYYCQQWNYPLITFGSGTKLEIQ]EPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGKIISFFLALTSTALLFLLFFLTLRFSVVKRGRKKLLYIFKQPFMRPVQTTQE

EDGCSCRFPEEEEGGCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

Humanized D10-V1
(SEQ ID NO. 1 + SEQ ID NO. 97)
MALPVTALLLPLALLLHAARP[QVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

S]GGGGSGGGGSGGGGS[EIVL(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIK]GLAVSTISSFFPPGYQIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR

Humanized D10-V2
(SEQ ID NO. 1 + SEQ ID NO. 98)
MALPVTALLLPLALLLHAARP[QVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

S]GGGGSGGGGSGGGGS[EIVL(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIK]GLAVSTISSFFPPGYQIIS

FFLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHD

GLYQGLSTATKDTYDALHMQALPPR

Humanized D10-V3
(SEQ ID NO. 1 + SEQ ID NO. 99)
MALPVTALLLPLALLLHAARP[QVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

S]GGGGSGGGGSGGGGS[EIVL(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIK]TTTPAPRPPTPAPTIASQ

PLSLRPEACRPAAGGAVHTRGLDFACDIYIWAPLAGTCGVLLLSLVITLYCKRGRKKLLYIFKQPFMRPVQTTQEEDG

CSCRFPEEEEGGCELRVKFSRSADAPAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR

Humanized D10-V4
(SEQ ID NO. 1 + SEQ ID NO. 100)
MALPVTALLLPLALLLHAARP[QVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

SGGGGSGGGGSGGGGSEIVQ(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIKTTTPAPRPPTPAPTIASQ

PLSLRPEACRPAAGGAVHTRGLDFACDIISFFLALTSTALLFLLFFLTLRFSVVKRGRKKLLYIFKQPFMRPVQTTQEED

GCSCRFPEEEEGGCELRVKFSRSADAPAYQQGQNQLYNELNLGRREEYDVLDKRRGRDPEMGGKPRRKNPQEGLY

NELQKDKMAEAYSEIGMKGERRGKGHDGLYQGLSTATKDTYDALHMQALPPR

Humanized D10-V5

(SEQ ID NO. 1 + SEQ ID NO. 101)

MALPVTALLLPLALLLHAARPQVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

SGGGGSGGGGSGGGGSEIVL(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIKEPKSPDKTHTCPPCPAP

PVAGPSVFLFPPKPKDTLMIARTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPGKIYIWAPLAGTCGVLLL

SLVITLYCKRGRKKLLYIFKQPFMRPVQTTQEEDGCSCRFPEEEEGGCELRVKFSRSADAPAYQQGQNQLYNELNLG

RREEYDVLDKRRGRDPEMGGKPRRKNPQEGLYNELQKDKMAEAYSEIGMKGERRRGKGHDGLYQGLSTATKDTY

DALHMQALPPR

Humanized D10-V6

(SEQ ID NO. 1 + SEQ ID NO. 102)

MALPVTALLLPLALLLHAARPQVQL(Q/K)ESGPGLV(K/A)PSETLSLTCTVSGFSLTSYGYVHWVRQPPGKGLEWLG

VIWAGGFTNYN(P/S)SLKSRLTISKDNSKNQVSLKLSSVTA(A/D)DTA(V/M)YYCARRGSSYSMDYWGQGTLVTVS

SGGGGSGGGGSGGGGSEIVL(T/S)QSPATLSLSPGERATLSC(R/S)ASSNVSYIHWYQQK(P/S)GQAPRPWIYEISK

LA(T/S)GIPARFSGSGSGTDYTLTISSLE(P/A)EDFA(V/I)YYCQQWNYPLITFGQGTKLEIKEPKSPDKTHTCPPCPAP

PVAGPSVFLFPPKPKDTLMIARTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPGKIISFFLALTSTALLFLLF

FLTLRFSVVKRGRKKLLYIFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRGKGHDGLYQGLSTATKDT

YDALHMQALPPR

G6 v1

(SEQ ID NO. 1 + SEQ ID NO. 103)

MALPVTALLLPLALLLHAARPEVQLQQSGPELEKPGASVKISCKASGFAFTGYNMNWVKQTNGKSLEWIGSIDPYY

GGSTYNQKFKDKATLTVDKSSSTAYMQLKSLTSDDSAVYYCARSPGGDYAMDYWGQGTSVTVSSGGGGSGGGG

SGGGGSDIKMTQSPSSMYASVGERVTITCKASQGINSYSGWFQQKPGKSPKTLIYRGNRLVDGVPSRFSGSGSGQ

DYSLTISSLEYEDMGIYYCLQYDEFPYTFGGGTKLEIKGLAVSTISSFFPPGYQIYIWAPLAGTCGVLLLSLVITLYCKRGR

KKLLYIFKQPFMRPVQTTQEEDGCSCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKHDGLYQGLSTATKDTYDALHMQALPP

R

G6 v2

(SEQ ID NO. 1 + SEQ ID NO. 104)

MALPVTALLLPLALLLHAARPEVQLQQSGPELEKPGASVKISCKASGFAFTGYNMNWVKQTNGKSLEWIGSIDPYY

GGSTYNQKFKDKATLTVDKSSSTAYMQLKSLTSDDSAVYYCARSPGGDYAMDYWGQGTSVTVSSGGGGSGGGG

SGGGGSDIKMTQSPSSMYASVGERVTITCKASQGINSYSGWFQQKPGKSPKTLIYRGNRLVDGVPSRFSGSGSGQ

DYSLTISSLEYEDMGIYYCLQYDEFPYTFGGGTKLEIKGLAVSTISSFFPPGYQIISFFLALTSTALLFLLFFLTLRFSVVKRG

RKKLLYIFKQPFMRPVQTTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKHDGLYQGLSTATKDTYDALHMQALP

PR

G6 v3

(SEQ ID NO. 1 + SEQ ID NO. 105)

MALPVTALLLPLALLLHAARPEVQLQQSGPELEKPGASVKISCKASGFAFTGYNMNWVKQTNGKSLEWIGSIDPYY

GGSTYNQKFKDKATLTVDKSSSTAYMQLKSLTSDDSAVYYCARSPGGDYAMDYWGQGTSVTVSSGGGGSGGGG

SGGGGSDIKMTQSPSSMYASVGERVTITCKASQGINSYSGWFQQKPGKSPKTLIYRGNRLVDGVPSRFSGSGSGQ

DYSLTISSLEYEDMGIYYCLQYDEFPYTFGGGTKLEIKTTTPAPRPPTPAPTIASQPLSLRPEACRPAAGGAVHTRGLD

FACDIYIWAPLAGTCGVLLLSLVITLYCKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDKMAEAYSEIGMKGERRR

GKGHDGLYQGLSTATKDTYDALHMQALPPR

G6 v4

(SEQ ID NO. 1 + SEQ ID NO. 106)

MALPVTALLLPLALLLHAARPEVQLQQSGPELEKPGASVKISCKASGFAFTGYNMNWVKQTNGKSLEWIGSIDPYY

GGSTYNQKFKDKATLTVDKSSSTAYMQLKSLTSDDSAVYYCARSPGGDYAMDYWGQGTSVTVSSGGGGSGGGG

SGGGGSDIKMTQSPSSMYASVGERVTITCKASQGINSYSGWFQQKPGKSPKTLIYRGNRLVDGVPSRFSGSGSGQ

DYSLTISSLEYEDMGIYYCLQYDEFPYTFGGGTKLEIKTTTPAPRPPTPAPTIASQPLSLRPEACRPAAGGAVHTRGLD

FACDIISFFLALTSTALLFLLFFLTLRFSVVKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR

G6 v5

(SEQ ID NO. 1 + SEQ ID NO. 107)

MALPVTALLLPLALLLHAARPEVQLQQSGPELEKPGASVKISCKASGFAFTGYNMNWVKQTNGKSLEWIGSIDPYY

GGSTYNQKFKDKATLTVDKSSSTAYMQLKSLTSDDSAVYYCARSPGGDYAMDYWGQGTSVTVSSGGGGSGGGG

SGGGGSDIKMTQSPSSMYASVGERVTITCKASQGINSYSGWFQQKPGKSPKTLIYRGNRLVDGVPSRFSGSGSGQ

DYSLTISSLEYEDMGIYYCLQYDEFPYTFGGGTKLEIKEPKSPDKTHTCPPCPAPPVAGPSVFLFPPKPKDTLMIARTPE

VTCVVVDVSHEDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPGKIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYDALHMQALPPR

G6 v6
(SEQ ID NO. 1 + SEQ ID NO. 108)
MALPVTALLLPLALLLHAARP<u>EVQLQQSGPELEKPGASVKISCKASGFAFTGYNMNWVKQTNGKSLEWIGSIDPYY</u>
<u>GGSTYNQKFKDKATLTVDKSSTAYMQLKSLTSDDSAVYYCARSPGGDYAMDYWGQGTSVTVSS</u>GGGGSGGGG
SGGGGS<u>DIKMTQSPSSMYASVGERVTITCKASQGINSYSGWFQQKPGKSPKTLIYRGNRLVDGVPSRFSGSGSGQ</u>
<u>DYSLTISSLEYEDMGIYYCLQYDEFPYTFGGGTKLEIK</u>EPKSPDKTHTCPPCPAPPVAGPSVFLFPPKPKDTLMIARTPE
VTCVVVDVSHEDPEVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGKIISFFLALTSTALLFLLFFLTLRFSVVKRGRKKLLYIFKQPFM
RPVQTTQEEDGCSCRFPEEEEGGCELRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQALPPR

G3 v1
(SEQ ID NO. 1 + SEQ ID NO. 109)
MALPVTALLLPLALLLHAARP<u>QVQLQQPGAELVKPGTSVKLSCKASGYNFTNYWINWVKLRPGQGLEWIGEIYPGS</u>
<u>GSTNYNEKFKSKATLTADTSSSTAYMQLSSLASEDSALYYCARDGNYYAMDYWGQGTSVTVSS</u>GGGGSGGGGSG
GGGS<u>DIQMTQTTSSLSASLGDRVTITCRASQDINNYLNWYQQKPDGTVKLLIYYTSALHSGVPSRFSGSGSGTDYSL</u>
<u>TISNLEQEDIATYFCQQGNTLPPYTFGGGTKLEIK</u>GLAVSTISSFFPPGYQIYIWAPLAGTCGVLLLSLVITLYCKRGRKK
LLYIFKQPFMRPVQTTQEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKDTYDALHMQALPPR

G3 v2
(SEQ ID NO. 1 + SEQ ID NO. 110)
MALPVTALLLPLALLLHAARP<u>QVQLQQPGAELVKPGTSVKLSCKASGYNFTNYWINWVKLRPGQGLEWIGEIYPGS</u>
<u>GSTNYNEKFKSKATLTADTSSSTAYMQLSSLASEDSALYYCARDGNYYAMDYWGQGTSVTVSS</u>GGGGSGGGGSG
GGGS<u>DIQMTQTTSSLSASLGDRVTITCRASQDINNYLNWYQQKPDGTVKLLIYYTSALHSGVPSRFSGSGSGTDYSL</u>
<u>TISNLEQEDIATYFCQQGNTLPPYTFGGGTKLEIK</u>GLAVSTISSFFPPGYQIISFFLALTSTALLFLLFFLTLRFSVVKRGRK
KLLYIFKQPFMRPVQTTQEEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLSTATKDTYDALHMQALPPR

G3 v3
(SEQ ID NO. 1 + SEQ ID NO. 111)
MALPVTALLLPLALLLHAARP<u>QVQLQQPGAELVKPGTSVKLSCKASGYNFTNYWINWVKLRPGQGLEWIGEIYPGS</u>
<u>GSTNYNEKFKSKATLTADTSSSTAYMQLSSLASEDSALYYCARDGNYYAMDYWGQGTSVTVSS</u>GGGGSGGGGSG
GGGS<u>DIQMTQTTSSLSASLGDRVTITCRASQDINNYLNWYQQKPDGTVKLLIYYTSALHSGVPSRFSGSGSGTDYSL</u>
<u>TISNLEQEDIATYFCQQGNTLPPYTFGGGTKLEIK</u>TTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGERRRGKG

HDGLYQGLSTATKDTYDALHMQALPPR

G3 v4

(SEQ ID NO. 1 + SEQ ID NO. 112)

MALPVTALLLPLALLLHAARP QVQLQQPGAELVKPGTSVKLSCKASGYNFTNYWINWVKLRPGQGLEWIGEIYPGS

GSTNYNEKFKSKATLTADTSSSTAYMQLSSLASEDSALYYCARDGNYYAMDYWGQGTSVTVSS GGGGSGGGGSG

GGGS DIQMTQTTSSLSASLGDRVTITCRASQDINNYLNWYQQKPDGTVKLLIYYTSALHSGVPSRFSGSGSGTDYSL

TISNLEQEDIATYFCQQGNTLPPYTFGGGTKLEIK TTTPAPRPPTPAPTIASQPLSLRPEACRPAAGGAVHTRGLDFAC

DIISFFLALTSTALLFLLFFLTLRFSVVKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR

G3 v5

(SEQ ID NO. 1 + SEQ ID NO. 113)

MALPVTALLLPLALLLHAARP QVQLQQPGAELVKPGTSVKLSCKASGYNFTNYWINWVKLRPGQGLEWIGEIYPGS

GSTNYNEKFKSKATLTADTSSSTAYMQLSSLASEDSALYYCARDGNYYAMDYWGQGTSVTVSS GGGGSGGGGSG

GGGS DIQMTQTTSSLSASLGDRVTITCRASQDINNYLNWYQQKPDGTVKLLIYYTSALHSGVPSRFSGSGSGTDYSL

TISNLEQEDIATYFCQQGNTLPPYTFGGGTKLEIK EPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR

G3 v6

(SEQ ID NO. 1 + SEQ ID NO. 114)

MALPVTALLLPLALLLHAARP QVQLQQPGAELVKPGTSVKLSCKASGYNFTNYWINWVKLRPGQGLEWIGEIYPGS

GSTNYNEKFKSKATLTADTSSSTAYMQLSSLASEDSALYYCARDGNYYAMDYWGQGTSVTVSS GGGGSGGGGSG

GGGS DIQMTQTTSSLSASLGDRVTITCRASQDINNYLNWYQQKPDGTVKLLIYYTSALHSGVPSRFSGSGSGTDYSL

TISNLEQEDIATYFCQQGNTLPPYTFGGGTKLEIK EPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIISFFLALTSTALLFLLFFLTLRFSVVKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR

H10 v1

(SEQ ID NO. 1 + SEQ ID NO. 115)

MALPVTALLLPLALLLHAARP EVKLVESGGGLVKPGGSLKLSCAASGFTFSSYAMSWVRQTPEKRLEWVASISTGAS

AYFPDSVKGRFTISRDNARNILYLQMSSLRSEDTAMYYCARITTSTWYFDVWGAGTTVTVSS GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>GLAVSTISSFFPPGYQIYIWAPLAGTCGVLLLSLVITLYCKRGRKKLLYIF

KQPFMRPVQTTQEEDGCSCRFPFEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPPR

H10 v2

(SEQ ID NO. 1 + SEQ ID NO. 116)

MALPVTALLLPLALLLHAARP<u>EVKLVESGGGLVKPGGSLKLSCAASGFTFSSYAMSWVRQTPEKRLEWVASISTGAS</u>

<u>AYFPDSVKGRFTISRDNARNILYLQMSSLRSEDTAMYYCARITTSTWYFDVWGAGTTVTVSS</u>GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>GLAVSTISSFFPPGYQIISFFLALTSTALLFLLFFLTLRFSVVKRGRKKLLYI

FKQPFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDALHMQALPPR

H10 v3

(SEQ ID NO. 1 + SEQ ID NO. 117)

MALPVTALLLPLALLLHAARP<u>EVKLVESGGGLVKPGGSLKLSCAASGFTFSSYAMSWVRQTPEKRLEWVASISTGAS</u>

<u>AYFPDSVKGRFTISRDNARNILYLQMSSLRSEDTAMYYCARITTSTWYFDVWGAGTTVTVSS</u>GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>TTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR

H10 v4

(SEQ ID NO. 1 + SEQ ID NO. 118)

MALPVTALLLPLALLLHAARP<u>EVKLVESGGGLVKPGGSLKLSCAASGFTFSSYAMSWVRQTPEKRLEWVASISTGAS</u>

<u>AYFPDSVKGRFTISRDNARNILYLQMSSLRSEDTAMYYCARITTSTWYFDVWGAGTTVTVSS</u>GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>TTTPAPRPPTPAPTIASQPLSLRPEACRPAAGGAVHTRGLDFACDIISF

FLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHD

GLYQGLSTATKDTYDALHMQALPPR

H10 v5

(SEQ ID NO.1 + SEQ ID NO.119)

MALPVTALLLPLALLLHAARP<u>EVKLVESGGGLVKPGGSLKLSCAASGFTFSSYAMSWVRQTPEKRLEWVASISTGAS</u>

<u>AYFPDSVKGRFTISRDNARNILYLQMSSLRSEDTAMYYCARITTSTWYFDVWGAGTTVTVSS</u>GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>EPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGKIYIWAPLAGTCGVLLLSLVITLYCKRGRKKLLYIFKQPFMRPVQTTQE

EDGCSCRFPEEEEGGCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

H10 v6
(SEQ ID NO. 1 + SEQ ID NO. 120)
MALPVTALLLPLALLLHAARP<u>EVKLVESGGGLVKPGGSLKLSCAASGFTFSSYAMSWVRQTPEKRLEWVASISTGAS</u>

<u>AYFPDSVKGRFTISRDNARNILYLQMSSLRSEDTAMYYCARITTSTWYFDVWGAGTTVTVSS</u>GGGGSGGGGSGGG

GS<u>DIKMTQSPSSMYASLGERVTITCKASQDINSYLSWFQQKPGKSPKTLIYRANRLVDGVPSRFSGSGSGQDYSLTIS</u>

<u>SLEYEDMGIYYCLQYDEFPYTFGGGTKLEIK</u>EPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGKIISFFLALTSTALLFLLFFLTLRFSVVKRGRKKLLYIFKQPFMRPVQTTQ

EEDGCSCRFPEEEEGGCELRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR

Humanized H10-v1
(SEQ ID NO. 1 + SEQ ID NO. 121)
MALPVTALLLPLALLLHAARP<u>EV(Q/K)LVESGGGLVKPGGSLRLSCAASGFTFSSYAMSWVRQAPGKGLEWVASIS</u>

<u>TGASAYF(A/P)DSVKGRFTISRDNAKNSLYLQMNSLRAEDTA(V/M)YYCARITTSTWYFDVWGQGTTVTVSS</u>GGG

GSGGGGSGGGGS<u>DIQMT(Q/K)SPSSLSASVGDRVTITCRASQDINSYLSWFQQKPGKAPKTLIYRANRL(Q/V)SGV</u>

<u>PSRFSGSGSGQDYTLTISSLQ(P/Y)EDFATYYCLQYDEFPYTFGQGTKLEIK</u>GLAVSTISSFFPPGYQIYIWAPLAGTCG

VLLLSLVITLYCKRGRKKLLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRGKGHDGLYQGLSTATK

DTYDALHMQALPPR

Humanized H10-v2
(SEQ ID NO. 1 + SEQ ID NO. 122)
MALPVTALLLPLALLLHAARP<u>EV(Q/K)LVESGGGLVKPGGSLRLSCAASGFTFSSYAMSWVRQAPGKGLEWVASIS</u>

<u>TGASAYF(A/P)DSVKGRFTISRDNAKNSLYLQMNSLRAEDTA(V/M)YYCARITTSTWYFDVWGQGTTVTVSS</u>GGG

GSGGGGSGGGGS<u>DIQMT(Q/K)SPSSLSASVGDRVTITCRASQDINSYLSWFQQKPGKAPKTLIYRANRL(Q/V)SGV</u>

<u>PSRFSGSGSGQDYTLTISSLQ(P/Y)EDFATYYCLQYDEFPYTFGQGTKLEIK</u>GLAVSTISSFFPPGYQIISFFLALTSTALL

FLLFFLTLRFSVVKRGRKKLLYIFKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIGMKGERRRGKGHDGLYQGLSTA

TKDTYDALHMQALPPR

Humanized H10-v3
(SEQ ID NO. 1 + SEQ ID NO. 123)
MALPVTALLLPLALLLHAARP<u>EV(Q/K)LVESGGGLVKPGGSLRLSCAASGFTFSSYAMSWVRQAPGKGLEWVASIS</u>

<u>TGASAYF(A/P)DSVKGRFTISRDNAKNSLYLQMNSLRAEDTA(V/M)YYCARITTSTWYFDVWGQGTTVTVSS</u>GGG

GSGGGGSGGGGS|DIQMT(Q/K)SPSSLSASVGDRVTITCRASQDINSYLSWFQQKPGKAPKTLIYRANRL(Q/V)SGV

PSRFSGSGSGQDYTLTISSLQ(P/Y)EDFATYYCLQYDEFPYTFGQGTKLEIK|TTTPAPRPPTPAPTIASQPLSLRPEACR

PAAGGAVHTRGLDFACDIYIWAPLAGTCGVLLLSLVITLYCKRGRKKLLYIFKQPFMRPVQTTQEEDGCSCRFPEEEE

GGCELRVKFSRSADAPAYQQGQNQLYNELNLGRREEYDVLDKRRGRDPEMGGKPRRKNPQEGLYNELQKDKMA

EAYSEIGMKGERRRGKGHDGLYQGLSTATKDTYDALHMQALPPR

Humanized H10-v4
(SEQ ID NO. 1 + SEQ ID NO. 124)
MALPVTALLLPLALLLHAARP|EV(Q/K)LVESGGGLVKPGGSLRLSCAASGFTFSSYAMSWVRQAPGKGLEWVASIS

TGASAYF(A/P)DSVKGRFTISRDNAKNSLYLQMNSLRAEDTA(V/M)YYCARITTSTWYFDVWGQGTTVTVSS|GGG

GSGGGGSGGGGS|DIQMT(Q/K)SPSSLSASVGDRVTITCRASQDINSYLSWFQQKPGKAPKTLIYRANRL(Q/V)SGV

PSRFSGSGSGQDYTLTISSLQ(P/Y)EDFATYYCLQYDEFPYTFGQGTKLEIK|TTTPAPRPPTPAPTIASQPLSLRPEACR

PAAGGAVHTRGLDFACDIISFFLALTSTALLFLLFFLTLRFSVVKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQEGLYNELQKDKM

AEAYSEIGMKGERRRGKGHDGLYQGLSTATKDTYDALHMQALPPR

Humanized H10-v5
(SEQ ID NO. 1 + SEQ ID NO. 125)
MALPVTALLLPLALLLHAARP|EV(Q/K)LVESGGGLVKPGGSLRLSCAASGFTFSSYAMSWVRQAPGKGLEWVASIS

TGASAYF(A/P)DSVKGRFTISRDNAKNSLYLQMNSLRAEDTA(V/M)YYCARITTSTWYFDVWGQGTTVTVSS|GGG

GSGGGGSGGGGS|DIQMT(Q/K)SPSSLSASVGDRVTITCRASQDINSYLSWFQQKPGKAPKTLIYRANRL(Q/V)SGV

PSRFSGSGSGQDYTLTISSLQ(P/Y)EDFATYYCLQYDEFPYTFGQGTKLEIK|EPKSPDKTHTCPPCPAPPVAGPSVFLF

PPKPKDILMIARTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGKIYIWAPLAGTCGVLLLSLVITLYCKR

GRKKLLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQAL

PPR

Humanized H10-v6
(SEQ ID NO. 1 + SEQ ID NO. 126)
MALPVTALLLPLALLLHAARP|EV(Q/K)LVESGGGLVKPGGSLRLSCAASGFTFSSYAMSWVRQAPGKGLEWVASIS

TGASAYF(A/P)DSVKGRFTISRDNAKNSLYLQMNSLRAEDTA(V/M)YYCARITTSTWYFDVWGQGTTVTVSS|GGG

GSGGGGSGGGGS|DIQMT(Q/K)SPSSLSASVGDRVTITCRASQDINSYLSWFQQKPGKAPKTLIYRANRL(Q/V)SGV

PSRFSGSGSGQDYTLTISSLQ(P/Y)EDFATYYCLQYDEFPYTFGQGTKLEIK|EPKSPDKTHTCPPCPAPPVAGPSVFLF

PPKPKDTLMIARTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGKIISFFLALTSTALLFLLFFLTLRFSVVK

RGRKKLLYIFKQPFMRPVQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQGLSTATKDTYDALHMQA

```
LPPR

2A4 v1
                                                    (SEQ ID NO. 1 + SEQ ID NO. 127)
MALPVTALLLPLALLLHAARPEVKLQQSGPELVKPGASVKISCKTSGYTFTEYTMHWVKQSHGKSLEWIGGINPNN

GGTSYNQKFKGKATLTVDKSSSTAYMELRSLTSEDSAVYYCALQGFAYWGQGTPLIVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKGLAVSTISSFFPPGYQIYIWAPLAGTCGVLLLSLVITLYCKRGRKKLLY

IFKQPFMRPVQTTQEEDGCSCRFPEEEEGGCELRVKFSRSADAPAYQQGQNQLYNELNLGRREEYDVLDKRRGRD

PEMGGKPRRKNPQEGLYNELQKDKMAEAYSEIGMKGERRRGKGHDGLYQGLSTATKDTYDALHMQALPPR

2A4 v2
                                                    (SEQ ID NO. 1 + SEQ ID NO. 128)
MALPVTALLLPLALLLHAARPEVKLQQSGPELVKPGASVKISCKTSGYTFTEYTMHWVKQSHGKSLEWIGGINPNN

GGTSYNQKFKGKATLTVDKSSSTAYMELRSLTSEDSAVYYCALQGFAYWGQGTPLIVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKGLAVSTISSFFPPGYQIISFFLALTSTALLFLLFFLTLRFSVVKRGRKKL

LYIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR

2A4 v3
                                                    (SEQ ID NO. 1 + SEQ ID NO. 129)
MALPVTALLLPLALLLHAARPEVKLQQSGPELVKPGASVKISCKTSGYTFTEYTMHWVKQSHGKSLEWIGGINPNN

GGTSYNQKFKGKATLTVDKSSSTAYMELRSLTSEDSAVYYCALQGFAYWGQGTPLTVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKTTTPAPRPPTPAPTIASQPLSLRPEACRPAAGGAVHTRGLDFACDI

YIWAPLAGTCGVLLLSLVITLYCKRGRKKLLYIFKQPFMRPVQTTQEEDGCSCRFPEEEEGGCELRVKFSRSADAPAY

QQGQNQLYNELNLGRREEYDVLDKRRGRDPEMGGKPRRKNPQEGLYNELQKDKMAEAYSEIGMKGERRRGKGH

DGLYQGLSTATKDTYDALHMQALPPR

2A4 v4
                                                    (SEQ ID NO. 1 + SEQ ID NO. 130)
MALPVTALLLPLALLLHAARPEVKLQQSGPELVKPGASVKISCKTSGYTFTEYTMHWVKQSHGKSLEWIGGINPNN

GGTSYNQKFKGKATLTVDKSSSTAYMELRSLTSEDSAVYYCALQGFAYWGQGTPLTVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKTTTPAPRPPTPAPTIASQPLSLRPEACRPAAGGAVHTRGLDFACDII

SFFLALTSTALLFLLFFLTLRFSVVKRGRKKLLYIFKQPFMRPVQTTQEEDGCSCRFPEEEEGGCELRVKFSRSADAPAY

QQGQNQLYNELNLGRREEYDVLDKRRGRDPEMGGKPRRKNPQEGLYNELQKDKMAEAYSEIGMKGERRRGKGH

DGLYQGLSTATKDTYDALHMQALPPR

2A4 v5
                                                    (SEQ ID NO. 1 + SEQ ID NO. 131)
MALPVTALLLPLALLLHAARPEVKLQQSGPELVKPGASVKISCKTSGYTFTEYTMHWVKQSHGKSLEWIGGINPNN
```

```
GGTSYNQKFKGKATLTVDKSSTAYMELRSLTSEDSAVYYCALQGFAYWGQGTPLIVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKEPKSPDKTHTCPPCPAPPVAGPSVFLFPPKPKDTLMIARTPEVTCV

VVDVSHEDPEVKFNWYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGKIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

2A4 v6
                                                                (SEQ ID NO. 1 + SEQ ID NO. 132)
MALPVTALLLPLALLLLHAARPEVKLQQSGPELVKPGASVKISCKTSGYTFTEYTMHWVKQSHGKSLEWIGGINPNN

GGTSYNQKFKGKATLTVDKSSTAYMELRSLTSEDSAVYYCALQGFAYWGQGTPLTVSSGGGGSGGGGSGGGGS

MEIEITQTPALMSASPGEKVTMTCSASSSVSYMYWYQQKPRSSPKPWIYLTSNLASGVPARFSGSGSGTSYSLTISS

MEAEDAATYYCQQWSSNPYTFGGGTRLELKEPKSPDKTHTCPPCPAPPVAGPSVFLFPPKPKDTLMIARTPEVTCV

VVDVSHEDPEVKFNWYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGKIISFFLALTSTALLFLLFFLTLRFSVVKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

1C11 v1
                                                                (SEQ ID NO. 1 + SEQ ID NO. 133)
MALPVTALLLPLALLLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLTCRASQDIGSSLNWLQQEPDGTIKRLIYATSSLDSGVPKRFSGSRSGSDYSLT

ISSLESEDFVDYYCLQYASSPYTFGGGTKLELKGLAVSTISSFFPPGYQIYIWAPLAGTCGVLLLSLVITLYCKRGRKKLLY

IFKQPFMRPVQTTQEEDGCSCRFPEEEEGGCELRVKFSRSADAPAYQQGQNQLYNELNLGRREEYDVLDKRRGRD

PEMGGKPRRKNPQEGLYNELQKDKMAEAYSEIGMKGERRRGKGHDGLYQGLSTATKDTYDALHMQALPPR

1C11 v2
                                                                (SEQ ID NO. 1 + SEQ ID NO. 134)
MALPVTALLLPLALLLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLICRASQDIGSSLNWLQQEPDGTIKRLIYATSSLDSGVPKRFSGSRSGSDYSLT

ISSLESEDFVDYYCLQYASSPYTFGGGTKLELKGLAVSTISSFFPPGYQIISFFLALTSTALLFLLFFLTLRFSVVKRGRKKLL

YIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR

1C11 v3
```

-continued (SEQ ID NO. 1 + SEQ ID NO. 135)
MALPVTALLLPLALLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLTCRASQDIGSSLNWLQQEPDGTIKRLIYATSSLDSGVPKRFSGSRSGSDYSLT

ISSLESEDFVDYYCLQYASSPYTFGGGTKLELKTTTPAPRPPTPAPTIASQPLSLRPEACRPAAGGAVHTRGLDFACDIY

IWAPLAGTCGVLLLSLVITLYCKRGRKKLLYIFKQPFMRPVQTTQEEDGCSCRFPEEEEGGCELRVKFSRSADAPAYQ

QGGNQLYNELNLGRREEYDVLDKRRGRDPEMGGKPRRKNPQEGLYNELQKDKMAEAYSEIGMKGERRRGKGHD

GLYQGLSTATKDTYDALHMQALPPR

1C11 v4

(SEQ ID NO. 1 + SEQ ID NO. 136)
MALPVTALLLPLALLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLTCRASQDIGSSLNWLQQEPDGTIKRLIYATSSLDSGVPKRFSGSRSGSDYSLT

ISSLESEDFVDYYCLQYASSPYTFGGGTKLELKTTTPAPRPPTPAPTIASQPLSLRPEACRPAAGGAVHTRGLDFACDII

SFFLALTSTALLFLLFFLTLRFSVVKRGRKKLLYIFKQPFMRPVQTTQEEDGCSCRFPEEEEGGCELRVKFSRSADAPAY

QQGGNQLYNELNLGRREEYDVLDKRRGRDPEMGGKPRRKNPQEGLYNELQKDKMAEAYSEIGMKGERRRGKGH

DGLYQGLSTATKDTYDALHMQALPPR

1C11 v5

(SEQ ID NO. 1 + SEQ ID NO. 137)
MALPVTALLLPLALLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLTCRASQDIGSSLNWLQQEPDGTIKRLIYATSSLDSGVPKRFSGSRSGSDYSLT

ISSLESEDFVDYYCLQYASSPYTFGGGTKLELKEPKSPDKTHTCPPCPAPPVAGPSVFLFPPKPKDTLMIARTPEVTCV

VVDVSHEDPEVKFNWYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGKIYIWAPLAGTCGVLLLSLVITLYCKRGRKKLLYIFKQPFMRPVQT

TQEEDGCSCRFPEEEEGGCELRVKFSRSADAPAYQQGGNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

1C11 v6

(SEQ ID NO. 1 + SEQ ID NO. 138)
MALPVTALLLPLALLLHAARPEVKLQESGAELARPGASVKMSCKASGYTFTSYTMHWVKQRPGQGLEWIGYINPSS

GYTEYNQKFKDKTTLTADKSSSTAYMQLSSLTSGDSAVYYCARRVLWLRRGDYWGQGTILTVSAGGGGSGGGGSG

GGGSMEVLITQTPSSLSASLGERVSLTCRASQDIGSSLNWLQQEPDGTIKRLIYATSSLDSGVPKRFSGSRSGSDYSLT

ISSLESEDFVDYYCLQYASSPYTFGGGTKLELKEPKSPDKTHTCPPCPAPPVAGPSVFLFPPKPKDTLMIARTPEVTCV

VVDVSHEDPEVKFNWYVDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGKIISFFLALTSTALLFLLFFLTLRFSVVKRGRKKLLYIFKQPFMRPVQ

-continued

```
TTQEEDGCSCRFPEEEEGGCELRVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR
```

Example 1: Selection of ROR1-Positive and -Negative Cell Lines

To identify cell lines expressing different cell surface expression levels of ROR1, 12 human cell lines were analysed by flow cytometry using the Qifikit (Dako) and the anti-human ROR1 mAb clone 2A2 (see materials and methods). Nine of these cell lines had previously been described in the literature to be positive for ROR1 at the mRNA or protein level (Table 10).

TABLE 10

Cell lines reported to be positive for ROR1 in the literature

| cell line | description | cell type |
| --- | --- | --- |
| MDA-MB-231 | adherent | breast adenocarcinoma |
| PC-3 | adherent | prostatic adenocarcinoma |
| MDA-MB-468 | adherent | breast adenocarcinoma |
| Hs746T | adherent | gastric carcinoma |
| NCI-H1993 | adherent | non-small cell lung cancer |
| HT-29 | adherent | colorectal adenocarcinoma |
| A549 | adherent | human lung adenocarcinoma |
| Cal51 | adherent | breast carcinoma |
| Jeko-1 | suspension | Mantle cell lymphoma |

Figure 5:
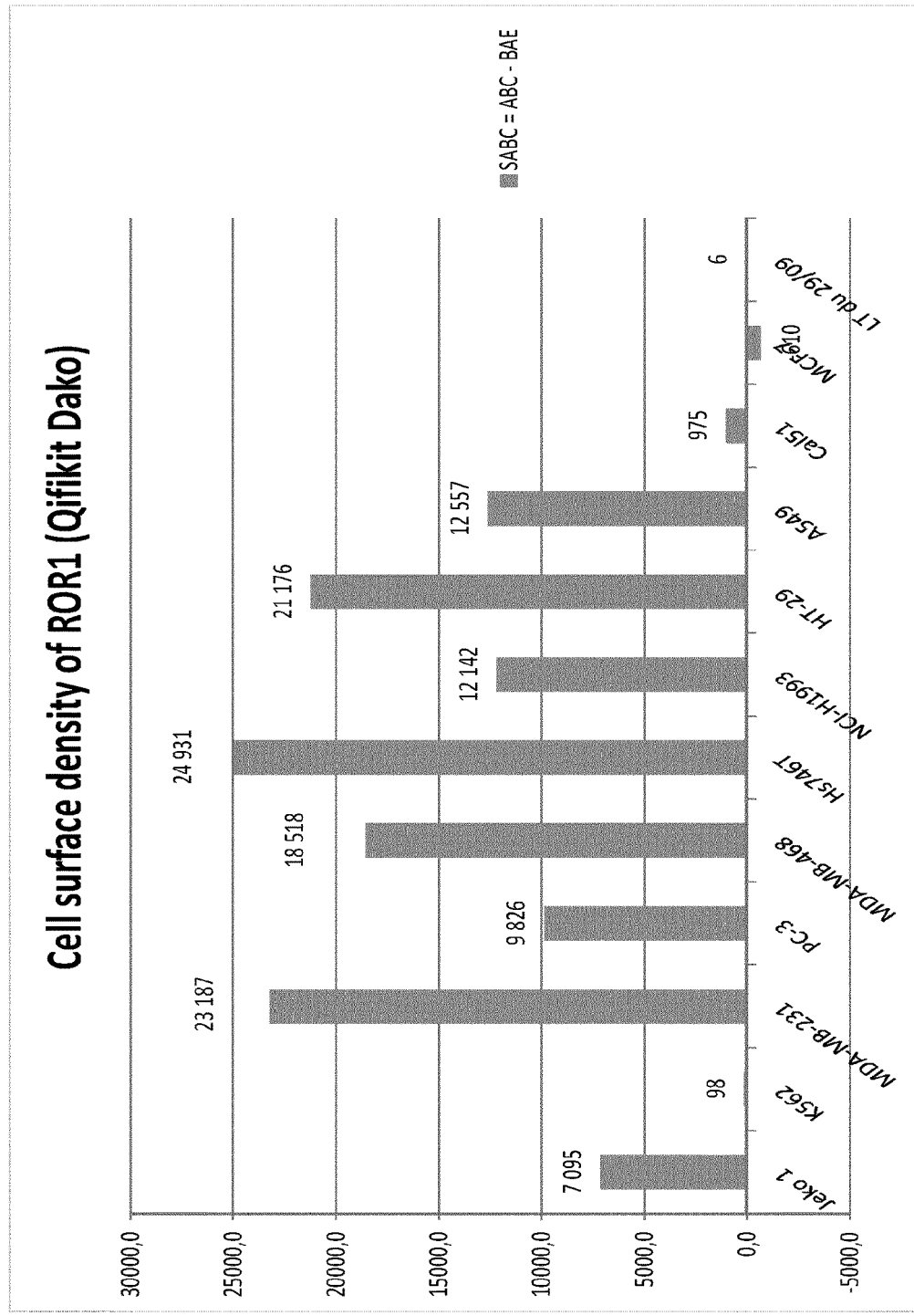
FIG. 5: Number of ROR1 surface molecules on different human cell lines.

Flow cytometry results indicate that MDA-MB-231 (ATCC® HTB-26), MDA-MB-468 (ATCC® HTB. 132), Hs746T (ATCC® HTB-135) and HT-29 (ATCC HTB-38) cells expressed the highest levels of ROR1 cell surface expression. Lower levels of ROR1 cell surface expression, approximately half that of the high expressing cell lines, were detected on PC-3 (ATCC.®. CRL-1435), NCI-H1993 (ATCC CRL 5909), A549 (ATCC CCL-185) and Jeko-1 (ATCC CRL-3006) cells (FIG. 5).

From these results, it is also observed that MCF-7, K562 and T cells did not express ROR1 and that the Cal51 expressed only very low levels of ROR1 on their surface.

From this cell lines, three adherent ones were selected to screen the activity of anti-ROR1 scCARs: PC-3 and MDA-MB-231 cells that express different levels of ROR1, and MCF-7 cells that are ROR1 negative.

Also, two suspension cell lines were selected to screen the activity of anti-ROR1 scCARs: Jeko-1 cells that are ROR1 positive and K562 cells that are ROR1 negative.

Example 2: Generation of Anti-ROR1 scCARs

A set of 18 ROR1-specific scCARs of 2nd generation (FIG. 1C) were created and tested in the following experiments.

They result from the fusion of the following building blocks of Tables 1-2:
scFvs from murine origin or humanized form from D10, G6, G3, H10, 2A4 or 1C11;
one spacer: human FcγRIIIα, CD8α or IgG1 hinge;
the transmembrane domain of human CD8α and the costimulatory domain of human 41BB;
the activation domain of human CD3

Different scFv were used in the scCARs to generate receptors of different binding affinities and different epitope specificities.

Figure 2:
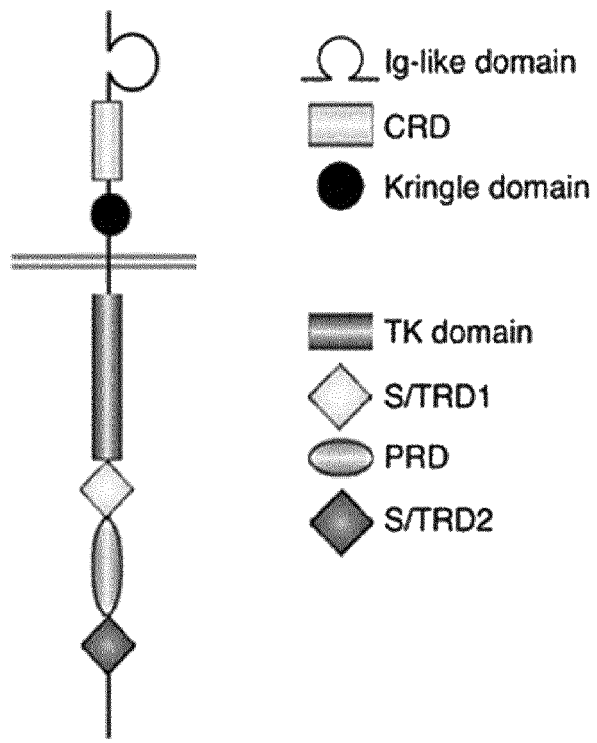
FIG. 2: Structure of the ROR1 protein which is composed of extracellular part, transmembrane part, and intracellular domains; the extra and intracellular ones containing multiple parts as explained previously.

The mAbs D10 and G6 target the 3' Ig like region and linker region between the Ig like domain and the CRD domain of ROR1 (FIG. 2)

The mAbs G3, H10 and 2A4 target the IgG like region of ROR1 (FIG. 2)

The mAb 1C11 targets the CRD domain of ROR1 (FIG. 2).

Three spacers of different length (16 AA, 45 AA and 231 AA) were used in the scCARs to try to optimize scCAR engagement by both proximal and distal epitopes of ROR1 (Guest et al., 2005).

Example 3: In Vitro Testing of Anti-ROR1 scCARs

Figure 6:
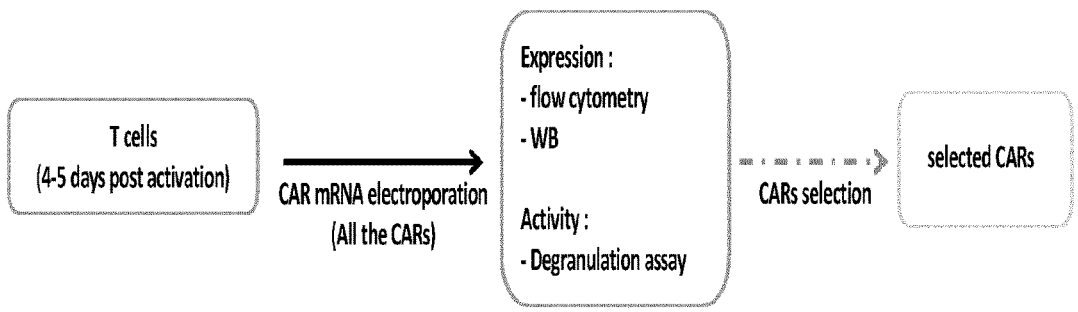
FIG. 6: scCARs screening procedure
Figure 6:
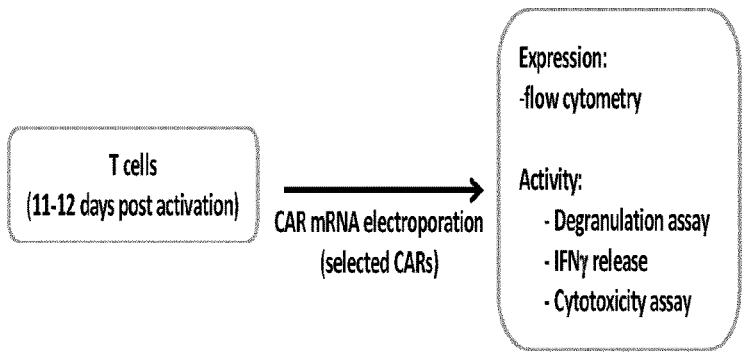

The anti-ROR1 scCARs designed as previously were tested in human primary T cells using a two-step screening method presented in FIG. 6.

In the first step of the screening process, primary human T cells previously activated for 4-5 days with anti-CD28/CD3 beads and IL-2 were electroporated with mRNA encoding the 18 anti-ROR1 scCARs presented earlier. One day post electroporation, scCAR expression was assessed by flow cytometry and western blot, and scCAR-modified T cell activity was assessed by measuring T cells degranulation. The scCARs that were detected by western blot and that induced significant specific degranulation of T cells (≥20%) upon coculture with at least one ROR1 positive cell line were selected to pass through the second step of the screening process.

In the second step of the screening process, primary human T cells previously activated for 11-12 days with anti-CD28/CD3 beads and IL-2 were electroporated with mRNA encoding the anti-ROR1 scCARs selected after the first screening step. One-two days post electroporation, scCARs expression was assessed by flow cytometry, and scCAR-modified T cell activity was assessed by measuring effector functions of T cells (degranulation, IFNg production and cytotolytic activity. The scCARs that induced significant specific degranulation of T cells (≥20%), significant specific cytotoxicity of T cells (≥20% of target cell lysis) and significant production of IFNg by T cells (≥1500 pg/ml) upon co-culture with at least one ROR1 positive cell line were selected as potential scCAR candidates.

The above scCARs were systematically compared to a benchmark scCAR containing the 2A2 scFv fused to a short hinge (SEQ ID NO. 79) as this scCAR was previously shown to be functional in Hudecek et al., 2013.

a) Primary Screening of scCARs scCAR Expression

Figure 7A:
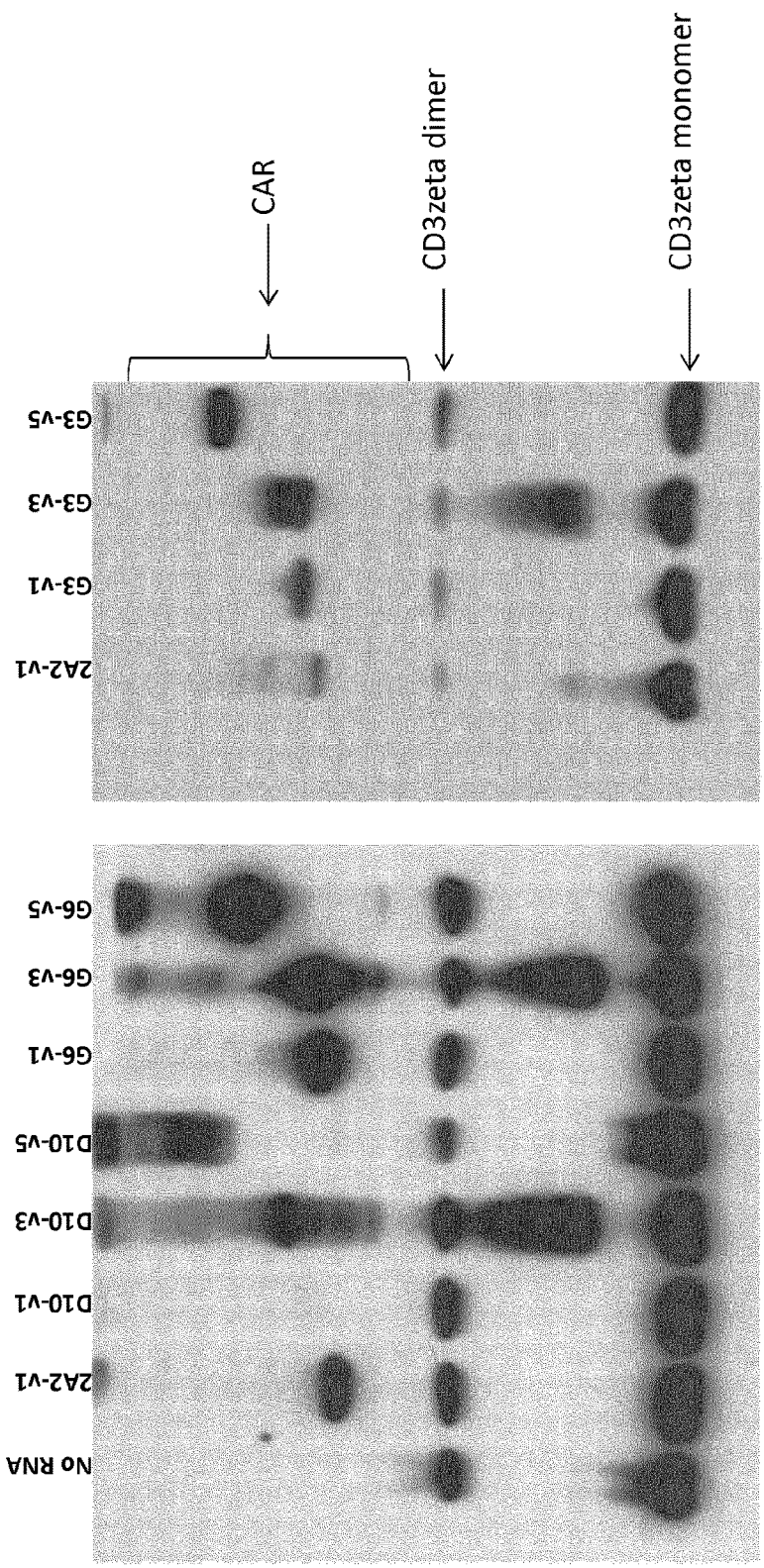
FIG. 7: Total expression of scCARs in human T cells. (A) Experiment 1. (B) Experiment 2.
Figure 7B:
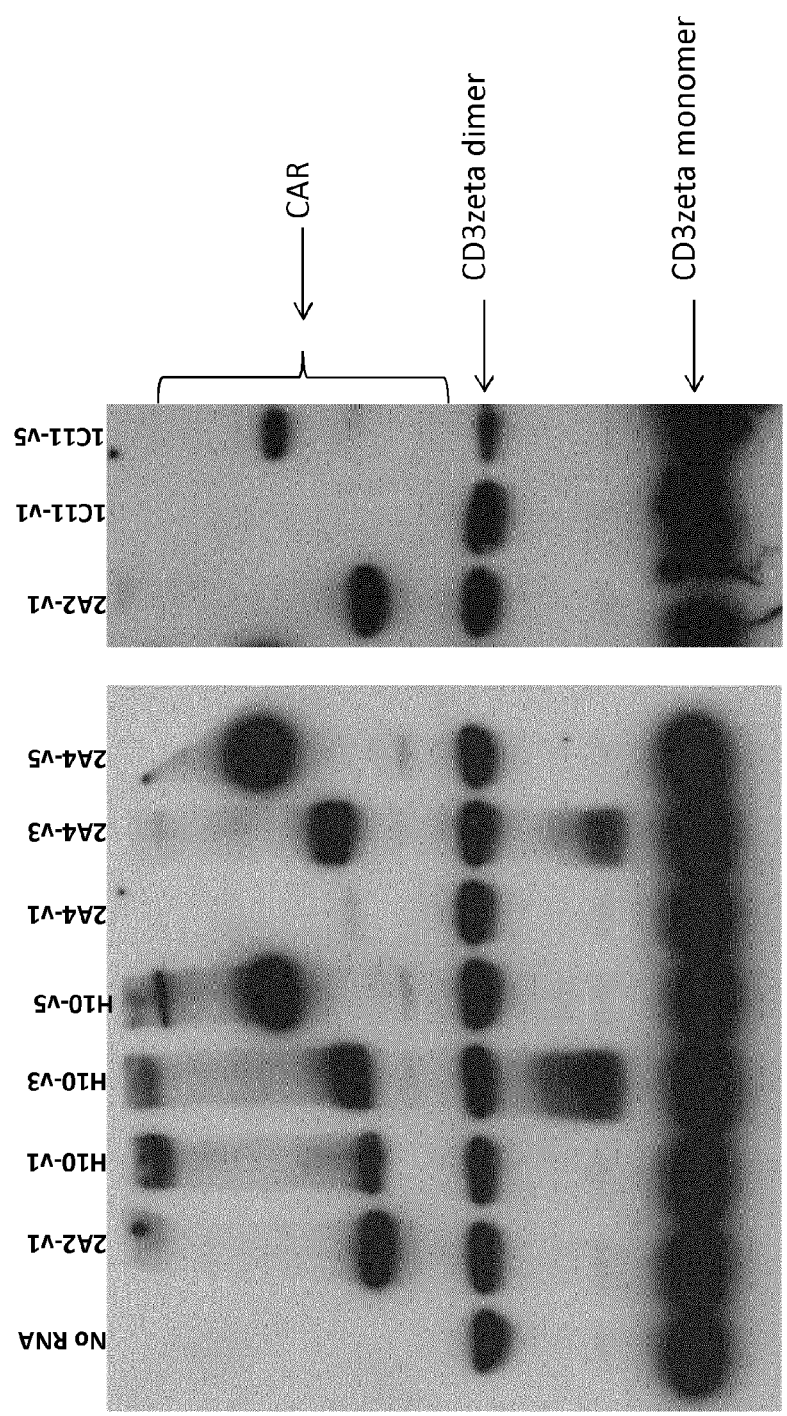

First, the total expression of anti-ROR1 scCARs was assessed in T cells by western blot using an anti-human CD3 zeta mAb. It was observed that the scCARs that contained the intermediate (CD8α hinge) or the long spacer (IgG1 hinge) were strongly detected in T cells lysates whatever the scFv they harbored. However, for the scCARs that contained the short spacer (FcγRIIIα), those with the G6, G3 and H10 scFvs were well detected, whereas those with the D10, 2A4 and 1C11 scFvs were weakly or not detected (FIGS. 7A and 7B).

Figure 8A:
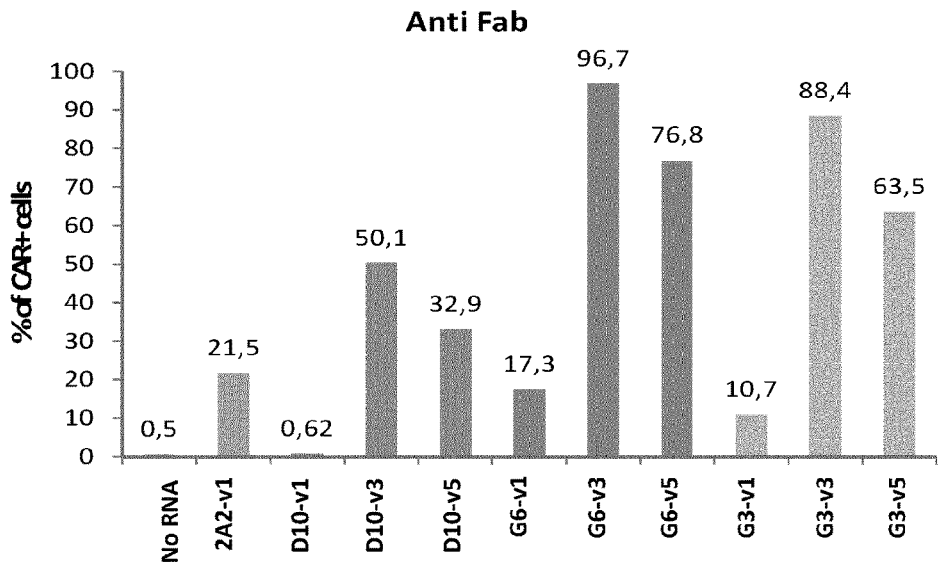
FIG. 8: Cell surface expression of scCARs on human T cells. (A) Experiment 1. (B) Experiment 2.
Figure 8A:
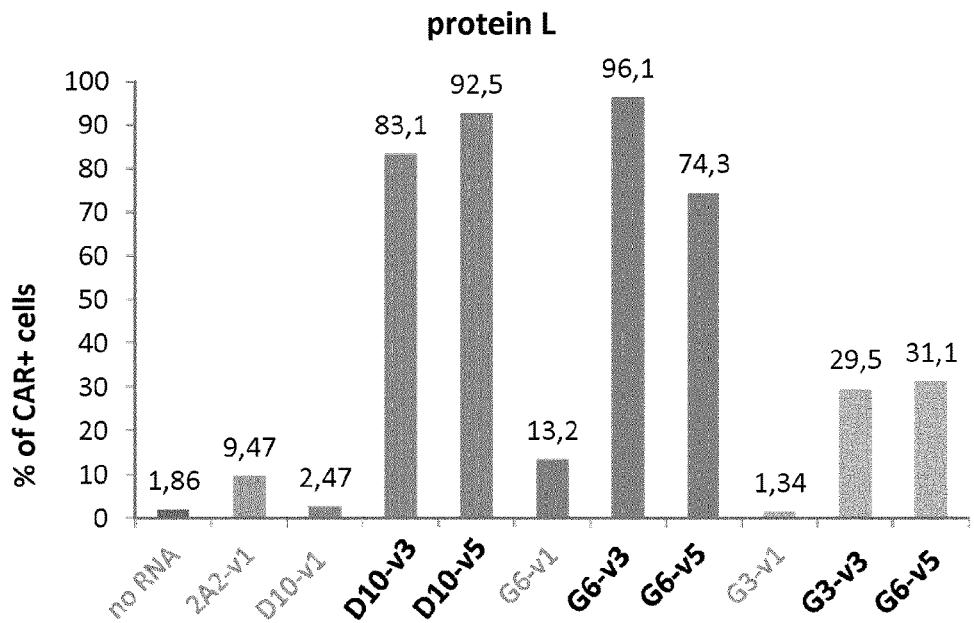
Figure 8B:
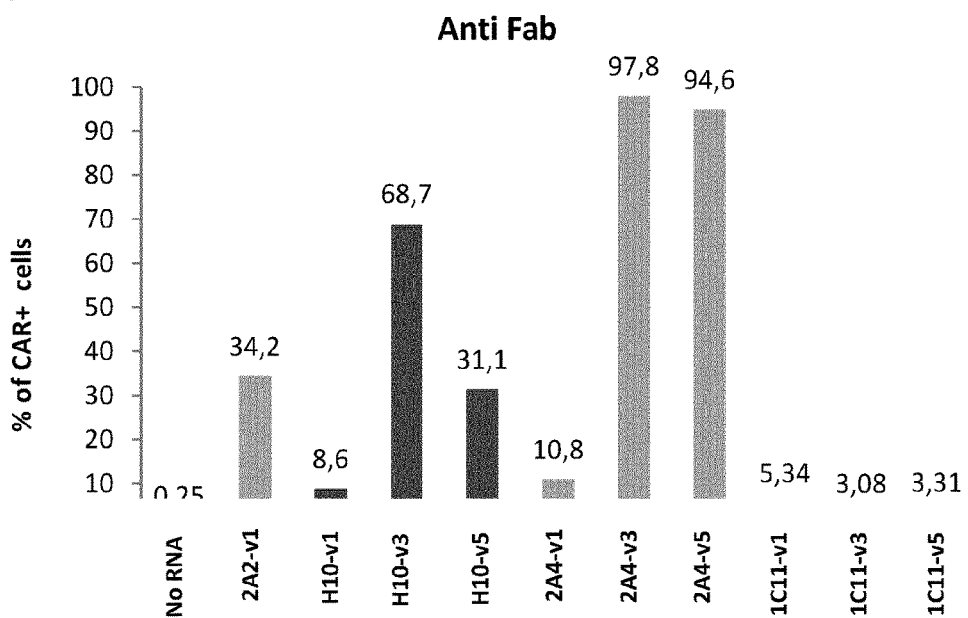
Figure 8B:
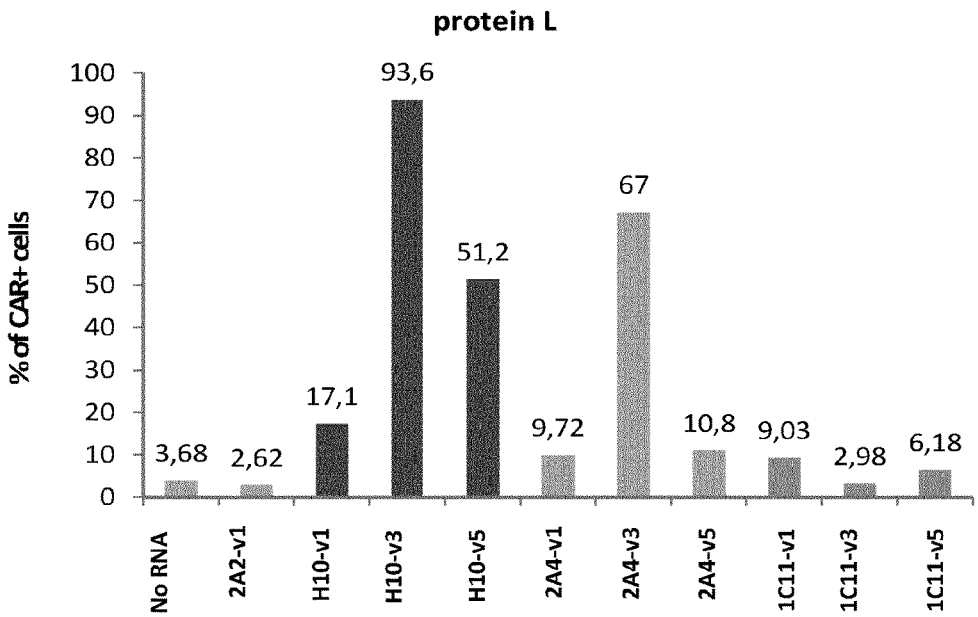

Then, the surface expression of anti-ROR1 scCARs on T cell was assessed by flow cytometry using anti-Fab or protein L (FIGS. 8A and 8B).

It was observed that:
  the scCARs D10-v3, D10-v5, G6-v3, G6-v5, G3-v3, G3-v5, H10-v3, H10-v5, 2A4-v3 and 2A4-v5 that were well detected in T cells lysate by western blot were also well detected on the T cell surface by flow cytometry;
  the scCARs D10-v1, 2A4-v1 and 1C11-v1 that were not or almost not detected in T cells lysate by western blot were also not detected on the T cell surface by flow cytometry.

scCAR Activity

To assess scCAR activity, the degranulation of scCAR-modified T cells was analysed upon co-culture with ROR1-positive (MDA-MB-231 and PC-3) or ROR1-negative (MCF-7) cells.

Figure 9A:
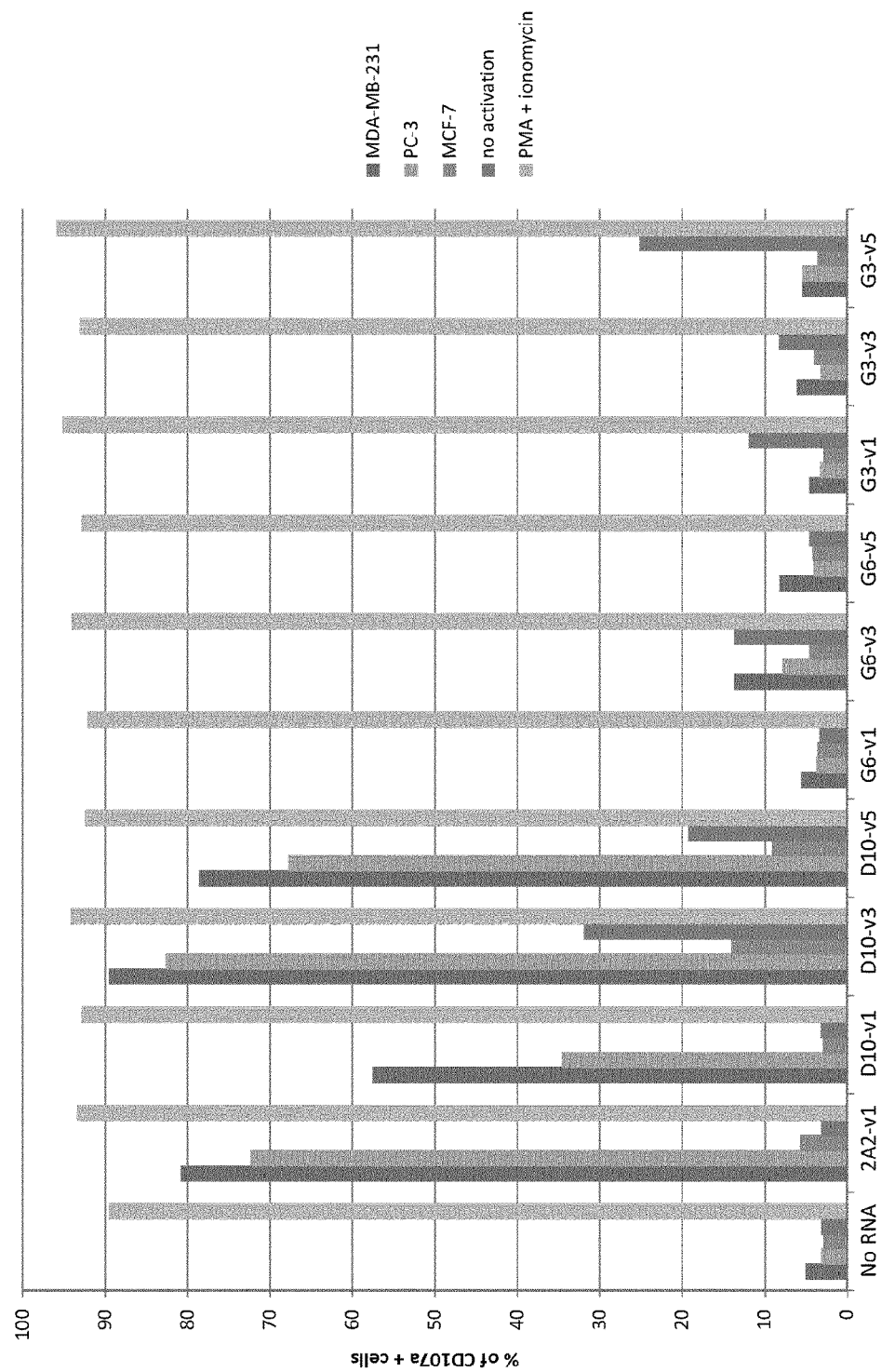
FIG. 9: Degranulation of scCAR modified T cells upon co-culture with target cells. (A) Experiment 1. (B) Experiment 2 (cell lines and/or treatment from the left to the right: MDA-MB-2301, PC-3, MCF-7, no activation, PMA+ ionomycin).
Figure 9B:
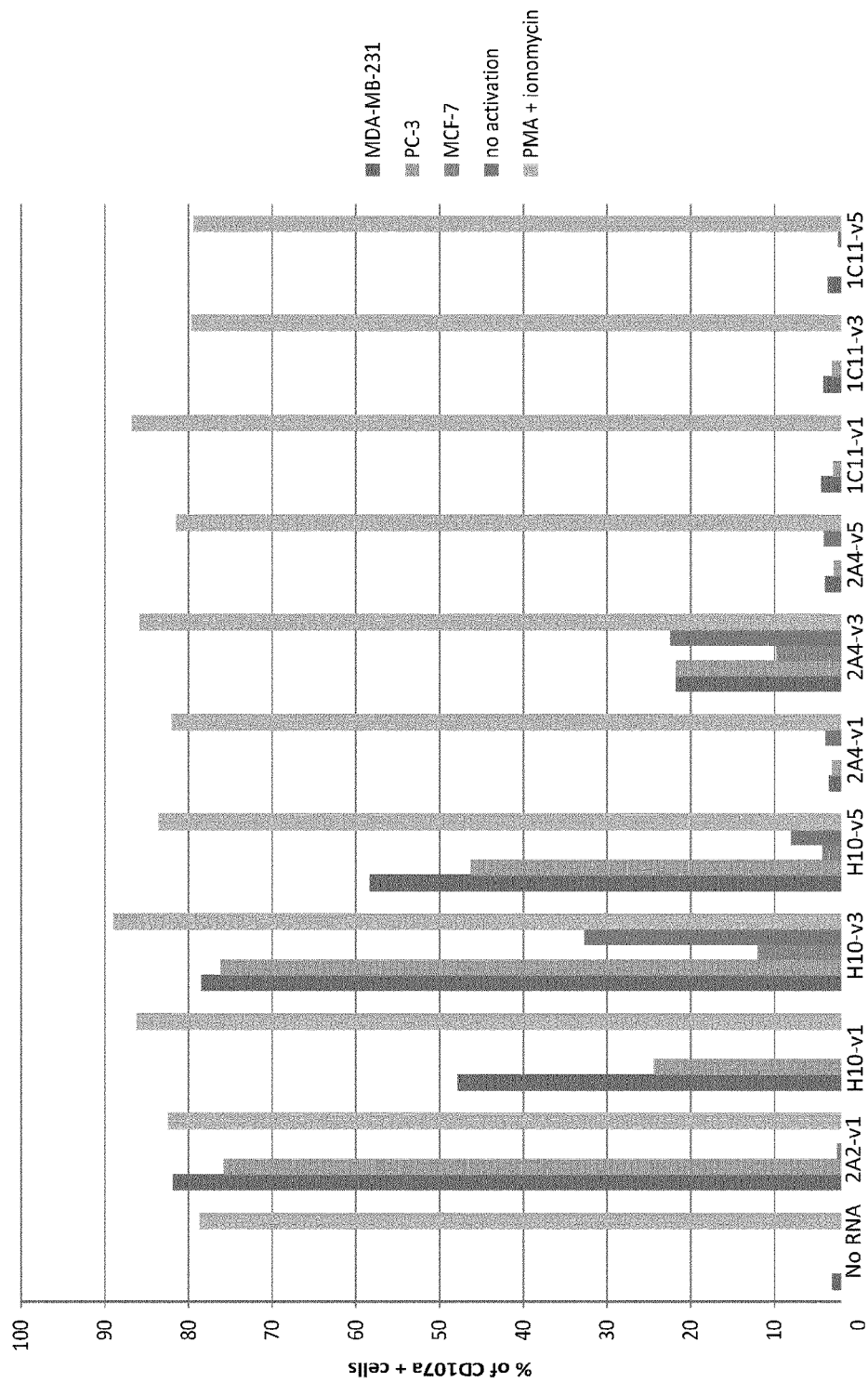

It was observed that the T cells modified with the scCARs D10-v1, D10-v3, D10-v5, H10-v1, H10-v3 and H10-v5 degranulated significantly more (≥20%) upon co-culture with MDA-MB-231 and PC-3 cells than upon co-culture with MCF-7 cells (FIGS. 9A and 9B).

FIG. 9 A and FIG. 9B show that the non-modified T cells as well as the T cells modified with the scCARs H10 and D10 degranulate at all upon coculture with MDA-MB-231, PC-3 and MCF-7 cells much better than with the scCAR G6, G3, 2A4 and 1C11.

Conclusion of Primary Screening:

Altogether these results demonstrated that among the 18 anti-ROR1 scCARs designed within the present invention, 6 (D10-v1, D10-v3, D10-v5, H10-v1, H10-v3 and H10-v5) met the criteria to be selected to pass through the second step of the screening process.

b) Secondary Screening of scCARs scCAR Expression

The surface expression of anti-ROR1 scCARs on T cells was assessed by flow cytometry using protein L.

Figure 10:
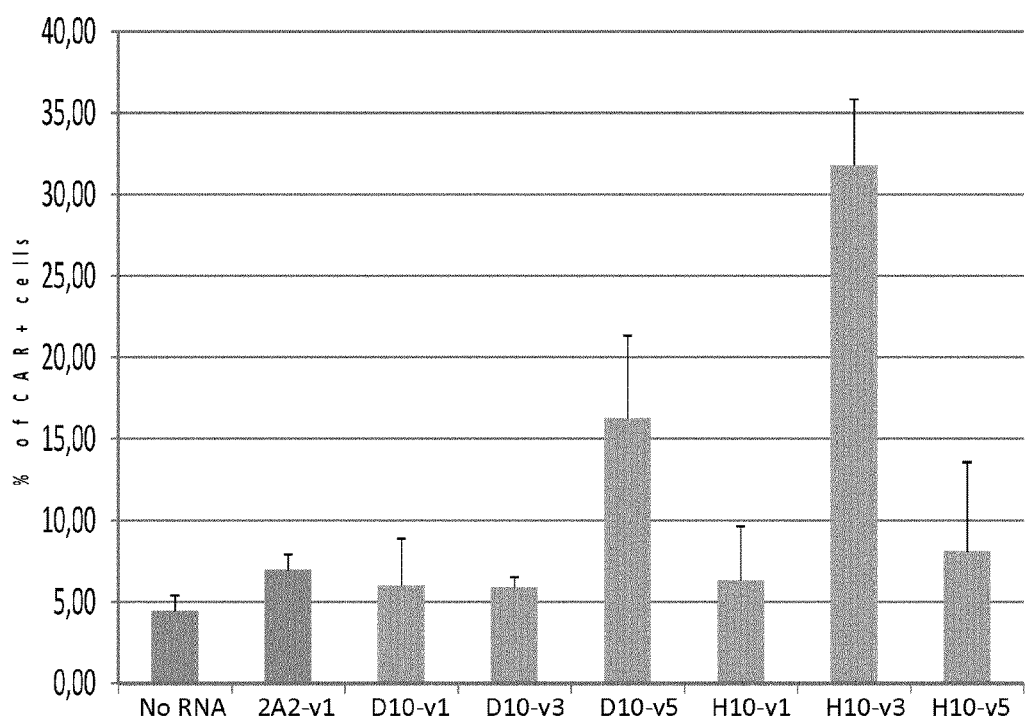
FIG. 10: Cell surface expression of scCARs on human T cells. Data are presented as mean+/−SD of four independent experiments.

It was observed that the scCARs D10-v3, D10-v5, H10-v3 and H10-v5 that were well detected on T cells electroporated 4-5 days post activation (FIGS. 8A and 8B) were not detected or only weakly detected on T cells electroporated 11-12 days post activation (FIG. 10).

scCAR Activity

First, to assess scCAR activity, the degranulation of scCAR-modified T cells was analysed upon co-culture with ROR1-positive (MDA-MB-231, PC-3 and Jeko-1) or ROR1-negative (MCF-7 and K562) cells.

Figure 11:
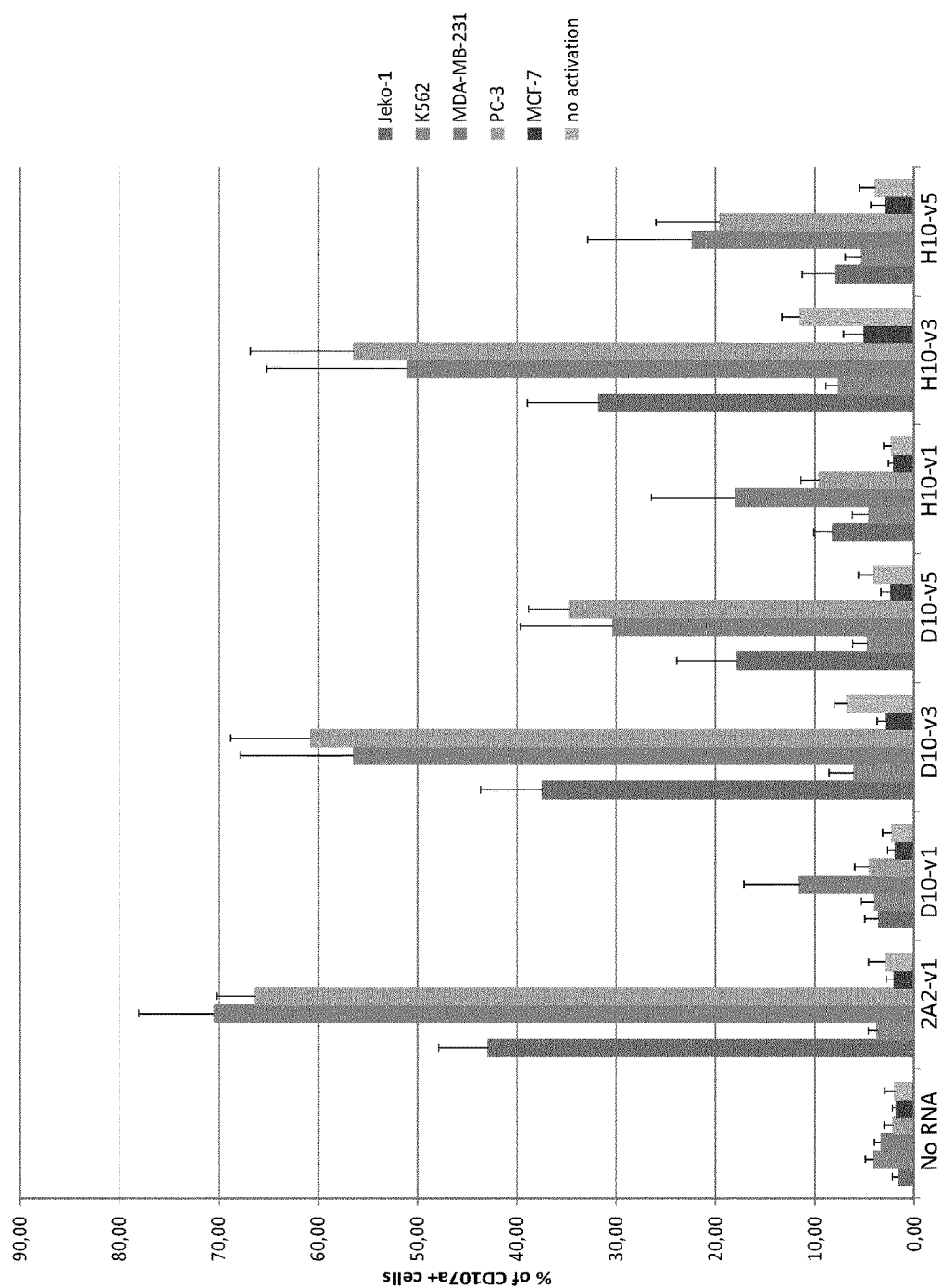
FIG. 11: Degranulation of scCAR modified T cells upon co-culture with target cells. Data are presented as mean+/−SD of four independent experiments.

It was observed that contrary to the T cells modified with the scCARs D10-v1, H10-v1 and H10-v5, the T cells modified with the scCARs D10-v3, D10-v5 and H10-v3 degranulated significantly more (≥20%) upon co-culture with MDA-MB-231 and PC-3 cells than upon co-culture with MCF-7 cells or in media alone (FIG. 11).

Then was analysed the production of IFNγ by scCAR-modified T cells upon co-culture with ROR1-positive (MDA-MB-231, PC-3 and Jeko-1) or ROR1-negative (MCF-7 and K562) cells.

Figure 12:
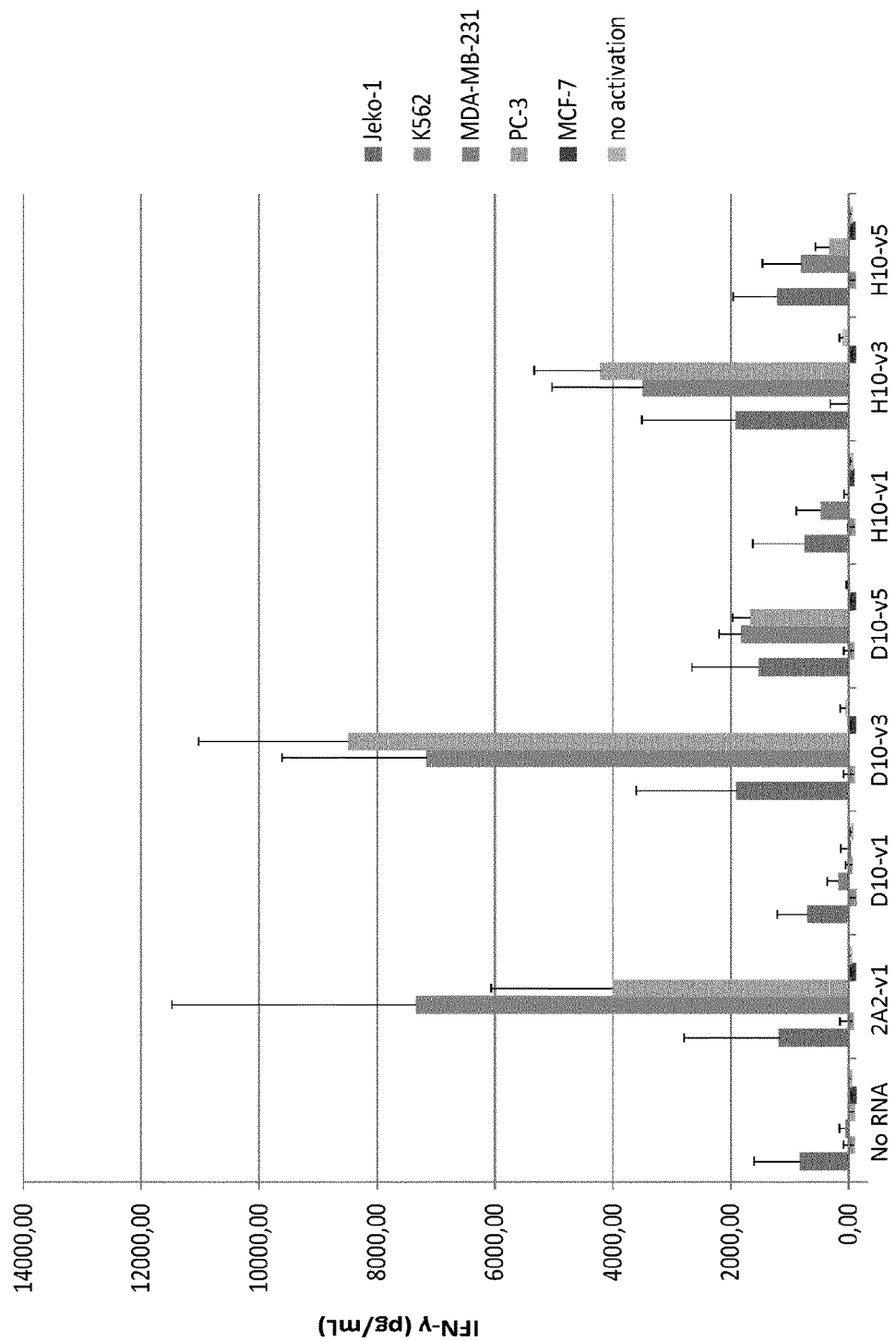
FIG. 12: IFNγ production by scCAR-modified T cells upon co-culture with target cells. Data are presented as mean+/−SD of four independent experiments (cell lines and/or treatment from the left to the right: Jeko-1, K562, MDA-MB-2301, PC-3, MCF-7, no activation).

It was observed that contrary to the T cells modified with the scCARs D10-v1, H10-v1 and H10-v5, the T cells modified with the scCARs D10-v3, D10-v5 and H10-v3 produced significantly more IFNγ (≥1500 pg/ml) upon co-culture with MDA-MB-231, PC-3 and Jeko-1 cells than upon co-culture with MCF-7, K562 cells or media alone (FIG. 12).

Finally, the cytotoxic activity of scCAR-modified T cells was analysed upon co-culture with ROR-1-negative (MCF-7 and K562) or ROR1-positive (MDA-MB-231, PC-3 and Jeko-1) cells.

Figure 13:
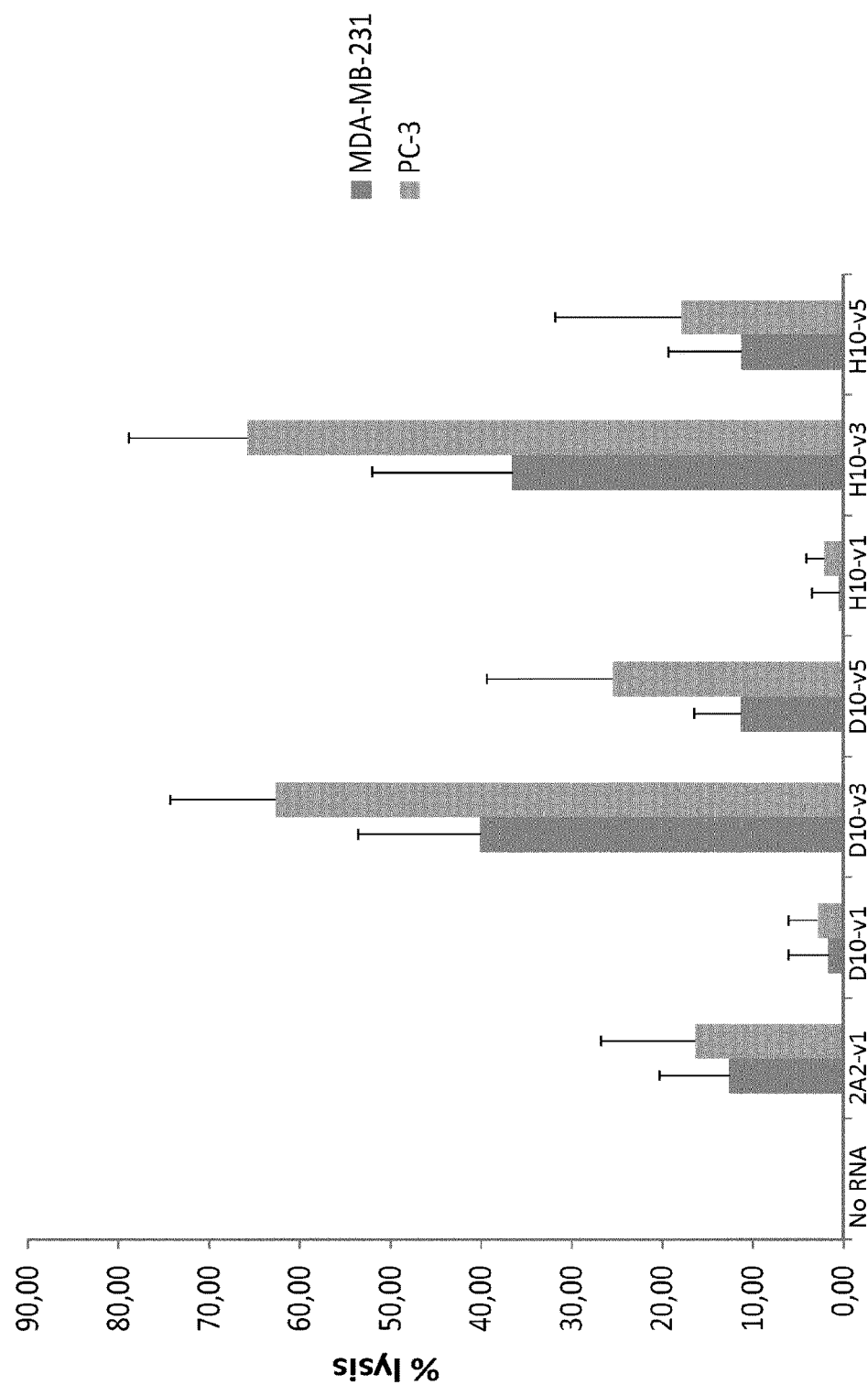
FIG. 13: Cytotoxic activity of scCAR-modified T cells upon co-culture with adherent target cells. Data are presented as mean+/−SD of four independent experiments.
Figure 14:
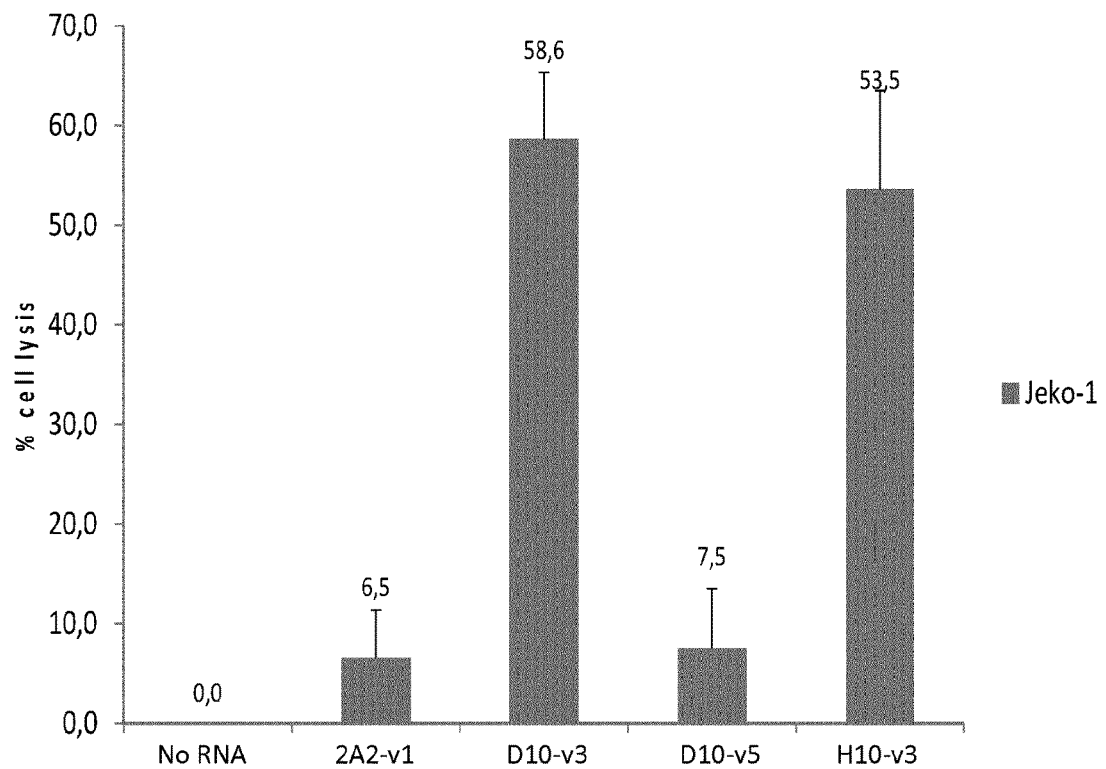
FIG. 14: Cytotoxic activity of scCAR-modified T cells upon co-culture with suspension target cells. Data are presented as mean+/−SD of four independent experiments.

It was observed that contrary to the T cells modified with the scCARs D10-v1, H10-v1 and H10-v5, the T cells modified with the scCARs D10-v3, D10-v5 and H10-v3 specifically killed more than 20% of PC-3 cells in co-culture (FIG. 13). Although the T cells modified with the scCARs D10-v3 and H10-v3 also killed more than 20% of MDA-MB-231 and Jeko-1 cells in co-culture, this was not the case for the T cells modified with the scCAR D10-v5 (FIG. 13 and FIG. 14).

Conclusion of Secondary Screening:

Altogether these results demonstrated that, from all the scCARs tested, D10-v3, D10-v5 and H10-v3 represent the most valuable scCARs.

A slight advantage for the 2 CARs of version V2 can be noted in terms of induction of cytotoxicity (better responses against the different ROR1-positive cell lines tested).

Example 4: Proliferation of TCRα Inactivated Cells Expressing a ROR1-CAR

Figure 15:
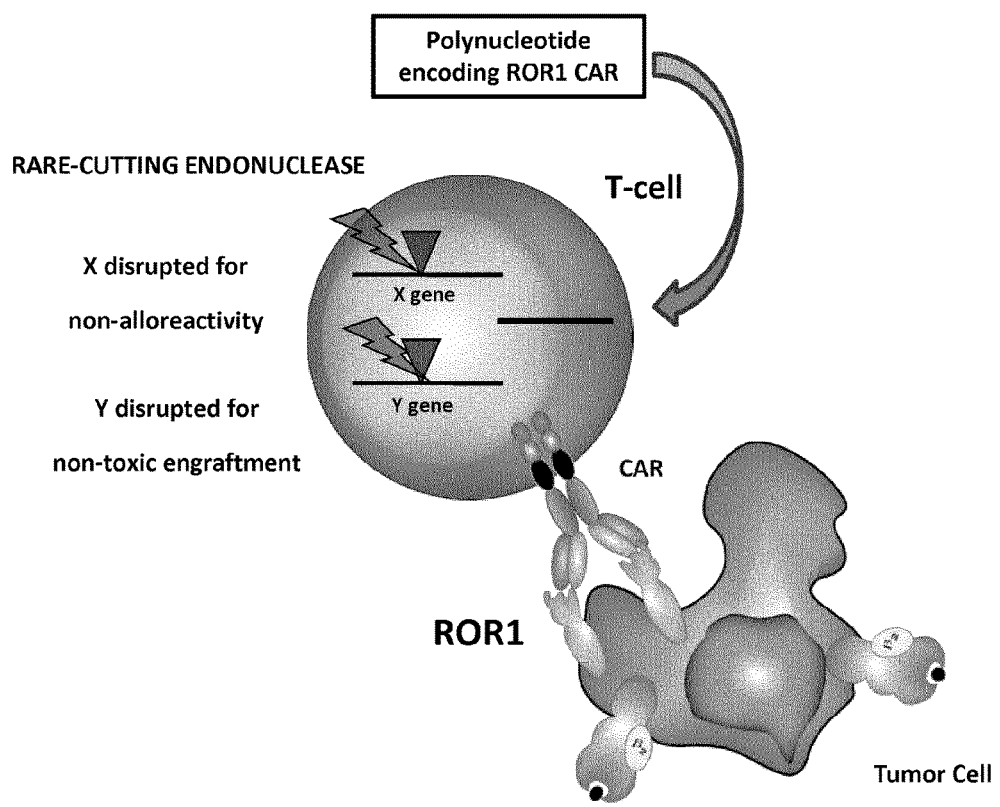
FIG. 15: Schematic representation of an engineered immune cell according to the invention. The engineered immune cell presented in this figure is a T-cell transduced with a retroviral polypeptide encoding CAR. This T-cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs such as CD52 (with respect to alemtuzumab) or HPRT (with respect to 6-Thioguanine).

FIG. 15 shows a schematic representation of TCRα inactivation by using rare cutting endonuclease. Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 11.

TABLE 11

TAL-nucleases targeting TCRalpha gene

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 139) | Repeat TRAC_T01-L (SEQ ID NO: 140) Repeat TRAC_T01-R (SEQ ID NO: 141) | TRAC_T01-L TALEN (SEQ ID NO: 142) TRAC_T01-R TALEN (SEQ ID NO: 143) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC T01 TALE-nucleases. 48 hours post-transfection, different groups of T cells from the same donor were respectively transduced with a lentiviral vector encoding one of the ROR1 CAR previously described (SEQ ID NO: 79 to 138). 2 days post-transduction, CD3$_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the ROR1 CARs, especially when reactivated with anti-CD28, was observed compared to non-transduced cells.

To investigate whether the human T cells expressing the ROR1 CAR display activated state, the expression of the activation marker CD25 are analyzed by FACS 7 days post transduction. The purified cells transduced with the lentiviral vector encoding ROR1 CAR assayed for CD25 expression at their surface in order to assess their activation in comparison with the non-transduced cells. Increased CD25 expression was indicative of anti-CD28 reactivation or no reactivation conditions.

REFERENCES

Arimondo, P. B., C. J. Thomas, et al. (2006). "Exploring the cellular activity of camptothecin-triple-helix-forming oligonucleotide conjugates." Mol Cell Biol 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." Rna 13(6): 803-10.

Baskar, S., Kwong, K. Y., Hofer, T., Levy, J. M., Kennedy, M. G., Lee, E., Staudt, L. M., Wilson, W. H., Wiestner, A., and Rader, C. (2008). Unique cell surface expression of receptor tyrosine kinase ROR1 in human B-cell chronic lymphocytic leukemia. Clin. Cancer Res. Off. J. Am. Assoc. Cancer Res. 14, 396-404.

Bicocca, V. T., Chang, B. H., Masouleh, B. K., Muschen, M., Loriaux, M. M., Druker, B. J., and Tyner, J. W. (2012). Crosstalk between ROR1 and the Pre-B cell receptor promotes survival of t(1;19) acute lymphoblastic leukemia. Cancer Cell 22, 656-667.

Bierer, B. E., G. Hollander, et al. (1993). "Cyclosporin A and FK506: molecular mechanisms of immunosuppression and probes for transplantation biology." Curr Opin Immunol 5(5): 763-9.

Boch, J., H. Scholze, et al. (2009). "Breaking the code of DNA binding specificity of TAL-type III effectors." Science 326(5959): 1509-12.

Byrd, John. (2014). "Chronic Lymphocytic Leukemia". ASH Annual Meeting & Exposition Choudhury, A., Derkow, K., Daneshmanesh, A. H., Mikaelsson, E., Kiaii, S., Kokhaei, P., Osterborg, A., and Mellstedt, H. (2010). Silencing of ROR1 and FMOD with siRNA results in apoptosis of CLL cells. Br. J. Haematol. 151, 327-335.

Choulika, A., A. Perrin, et al. (1995). "Induction of homologous recombination in mammalian chromosomes by using the I-SceI system of *Saccharomyces cerevisiae*." Mol Cell Biol 15(4): 1968-73.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Cooper, L. Innovative T Cell-Targeted Therapy for Ovarian Cancer. Annual report 2012 prepared for US Army medical research and Medical Command.

Cros, E. et al. (2004)."Problems related to resistance to cytarabine in acute myeloid leukemia". Leukemia & Lymphoma. 45(6):1123-1132.

Daneshmanesh A H, Mikaelsson E, Jeddi-Tehrani M, et al. (2008). "Ror1, a cell surface receptor tyrosine kinase is expressed in chronic lymphocytic leukemia and may serve as a putative target for therapy.". Int. J. Cancer 123 (5): 1190-5. doi:10.1002/ijc.23587

Dave, H., Anver, M. R., Butcher, D. O., Brown, P., Khan, J., Wayne, A. S., Baskar, S., and Rader, C. (2012). Restricted cell surface expression of receptor tyrosine kinase ROR1 in pediatric B-lineage acute lymphoblastic leukemia suggests targetability with therapeutic monoclonal antibodies. Plos One 7, e52655.

Deltcheva, E., K. Chylinski, et al. (2011). "CRISPR RNA maturation by trans-encoded small RNA and host factor RNase III." Nature 471(7340): 602-7.

Donnelly, M. and G. Elliott (2001). "Nuclear localization and shuttling of herpes simplex virus tegument protein VP13/14." J Virol 75(6): 2566-74.

Doronina, V. A., C. Wu, et al. (2008). "Site-specific release of nascent chains from ribosomes at a sense codon." Mol Cell Biol 28(13): 4227-39.

Eisenschmidt, K., T. Lanio, et al. (2005). "Developing a programmed restriction endonuclease for highly specific DNA cleavage." Nucleic Acids Res 33(22): 7039-47.

Fukuda, T., Chen, L., Endo, T., Tang, L., Lu, D., Castro, J. E., Widhopf, G. F., 2nd, Rassenti, L. Z., Cantwell, M. J., Prussak, C. E., et al. (2008). Antisera induced by infusions of autologous Ad-CD154-leukemia B cells identify ROR1 as an oncofetal antigen and receptor for Wnt5a. Proc. Natl. Acad. Sci. U.S.A 105, 3047-3052.

Gardin, C. et al. (2007). "Postremission treatment of elderly patients with acute myeloid leukemia in first complete remission after intensive induction chemotherapy:results of the multicenter randomized Acute Leukemia French Association (ALFA) 9803 trial". Blood. 109(12):5129-5135.

Gentile, A., Lazzari, L., Benvenuti, S., Trusolino, L., and Comoglio, P. M. (2011). Ror1 is a pseudokinase that is crucial for Met-driven tumorigenesis. Cancer Res. 71, 3132-3141.

Garneau, J. E., M. E. Dupuis, et al. (2010). "The CRISPR/Cas bacterial immune system cleaves bacteriophage and plasmid DNA." Nature 468(7320): 67-71.

Gasiunas, G., R. Barrangou, et al. (2012). "Cas9-crRNA ribonucleoprotein complex mediates specific DNA cleavage for adaptive immunity in bacteria." Proc Natl Acad Sci USA 109(39): E2579-86.

Guest, R. D., Hawkins, R. E., Kirillova, N., Cheadle, E. J., Arnold, J., O'Neill, A., Irlam, J., Chester, K. A., Kemshead, J. T., Shaw, D. M., et al. (2005). The role of extracellular spacer regions in the optimal design of chimeric immune receptors: evaluation of four different scFvs and antigens. J. Immunother. Hagerstown Md. 1997 28, 203-211.

Henderson, D. J., I. Naya, et al. (1991). "Comparison of the effects of FK-506, cyclosporin A and rapamycin on IL-2 production." Immunology 73(3): 316-21.

Hudecek, M., Schmitt, T. M., Baskar, S., Lupo-Stanghellini, M. T., Nishida, T., Yamamoto, T. N., Bleakley, M., Turtle, C. J., Chang, W.-C., Greisman, H. A., et al. (2010). The B-cell tumor-associated antigen ROR1 can be targeted with T cells modified to express a ROR1-specific chimeric antigen receptor. Blood 116, 4532-4541.

Hudecek M., Lupo Stanghellini M. T., Kosasih P. L., Sommermeyer D., Jensen M., Rader C., Riddell S. (2013).

"Receptor affinity and extracellular domain modifications affect tumor recognition by ROR1-specific chimeric antigen receptor T-cells." Clinical Cancer Researc 19(12): 3153-64

Jena, B., G. Dotti, et al. (2010). "Redirecting T-cell specificity by introducing a tumor-specific chimeric antigen receptor." Blood 116(7): 1035-44.

Jinek, M., K. Chylinski, et al. (2012). "A programmable dual-RNA-guided DNA endonuclease in adaptive bacterial immunity." Science 337(6096): 816-21.

June, C. H. et al. (2011). "T Cells with Chimeric Antigen Receptors Have Potent Antitumor Effects and Can Establish Memory in Patients with Advanced Leukemia". Sci. Transl. Med. 3(95):ra73.

Kalish, J. M. and P. M. Glazer (2005). "Targeted genome modification via triple helix formation." Ann N Y Acad Sci 1058: 151-61.

Klein, U., Tu, Y., Stolovitzky, G. A., Mattioli, M., Cattoretti, G., Husson, H., Freedman, A., Inghirami, G., Cro, L., Baldini, L., et al. (2001). Gene expression profiling of B cell chronic lymphocytic leukemia reveals a homogeneous phenotype related to memory B cells. J. Exp. Med. 194, 1625-1638.

Li, T., S. Huang, et al. (2011). "TAL nucleases (TALNs): hybrid proteins composed of TAL effectors and FokI DNA-cleavage domain." Nucleic Acids Res 39(1): 359-72.

Liu, J., M. W. Albers, et al. (1992). "Inhibition of T cell signaling by immunophilin-ligand complexes correlates with loss of calcineurin phosphatase activity." Biochemistry 31(16): 3896-901.

Mali, P., L. Yang, et al. (2013). "RNA-guided human genome engineering via Cas9." Science 339(6121): 823-6.

Matsuda, T., Nomi, M., Ikeya, M., Kani, S., Oishi, I., Terashima, T., Takada, S., and Minami, Y. (2001). Expression of the receptor tyrosine kinase genes, Ror1 and Ror2, during mouse development. Mech. Dev. 105, 153-156.

Moscou, M. J. and A. J. Bogdanove (2009). "A simple cipher governs DNA recognition by TAL effectors." Science 326(5959): 1501.

Paques, F. and P. Duchateau (2007). "Meganucleases and DNA double-strand break-induced recombination: perspectives for gene therapy." Curr Gene Ther 7(1): 49-66.

Park, T. S., S. A. Rosenberg, et al. (2011). "Treating cancer with genetically engineered T cells." Trends Biotechnol 29(11): 550-7.

Peipp, M., D. Saul, et al. (2004). "Efficient eukaryotic expression of fluorescent scFv fusion proteins directed against CD antigens for FACS applications." J Immunol Methods 285(2): 265-80.

Perrin, A., M. Buckle, et al. (1993). "Asymmetrical recognition and activity of the I-SceI endonuclease on its site and on intron-exon junctions." Embo J 12(7): 2939-47.

Pingoud, A. and G. H. Silva (2007). "Precision genome surgery." Nat Biotechnol 25(7): 743-4.

Porteus, M. H. and D. Carroll (2005). "Gene targeting using zinc finger nucleases." Nat Biotechnol 23(8): 967-73.

Reddy U R, Phatak S, Allen C, et al. (1997). "Localization of the human Ror1 gene (NTRKR1) to chromosome 1p31-p32 by fluorescence in situ hybridization and somatic cell hybrid analysis.". Genomics 41 (2): 283-5. doi:10.1006/geno.1997.4653

Rosenwald, A., Alizadeh, A. A., Widhopf, G., Simon, R., Davis, R. E., Yu, X., Yang, L., Pickeral, O. K., Rassenti, L. Z., Powell, J., et al. (2001). Relation of gene expression phenotype to immunoglobulin mutation genotype in B cell chronic lymphocytic leukemia. J. Exp. Med. 194, 1639-1647.

Rouet, P., F. Smih, et al. (1994). "Introduction of double-strand breaks into the genome of mouse cells by expression of a rare-cutting endonuclease." Mol Cell Biol 14(12): 8096-106.

Sorek, R., C. M. Lawrence, et al. (2013). "CRISPR-mediated Adaptive Immune Systems in Bacteria and Archaea." Annu Rev Biochem.

Stoddard, B. L. (2005). "Homing endonuclease structure and function." Q Rev Biophys 38(1): 49-95.

Yamaguchi, T., Yanagisawa, K., Sugiyama, R., Hosono, Y., Shimada, Y., Arima, C., Kato, S., Tomida, S., Suzuki, M., Osada, H., et al. (2012). NKX2-1/TITF1/TTF-1-Induced ROR1 is required to sustain EGFR survival signaling in lung adenocarcinoma. Cancer Cell 21 348-361.

Zhang, S., Chen, L., Cui, B., Chuang, H.-Y., Yu, J., Wang-Rodriguez, J., Tang, L., Chen, G., Basak, G. W., and Kipps, T. J. (2012a). ROR1 is expressed in human breast cancer and associated with enhanced tumor-cell growth. Plos One 7, e31127.

Zhang, S., Chen, L., Wang-Rodriguez, J., Zhang, L., Cui, B., Frankel, W., Wu, R., and Kipps, T. J. (2012b). The onco-embryonic antigen ROR1 is expressed by a variety of human cancers. Am. J. Pathol. 181, 1903-1910.

The invention claimed is:

1. A ROR1 (NTRKR1) specific chimeric antigen receptor (CAR) comprising:
   (a) an extracellular ligand binding-domain comprising a variable heavy chain comprising CDR regions as set forth in SEQ ID NO:54, SEQ ID NO:55, and SEQ ID NO:56, and a variable light chain comprising CDR regions as set forth in SEQ ID NO:59, SEQ ID NO:60, and SEQ ID NO:61,
   (b) a hinge comprising an amino acid sequence at least 95 percent identical to SEQ ID NO:4,
   (c) a transmembrane domain comprising an amino acid sequence at least 95 percent identical to SEQ ID NO:6, and
   (d) a cytoplasmic domain comprising (i) a signaling domain comprising an amino acid sequence at least 95 percent identical to SEQ ID NO:9 and (ii) a co-stimulatory domain comprising an amino acid sequence at least 95 percent identical to SEQ ID NO:8.

2. The ROR1 specific CAR according to claim 1, wherein the transmembrane domain comprises the amino acid sequence set forth in SEQ ID NO:6.

3. The ROR1 specific CAR according to claim 1, wherein the hinge comprises the amino acid sequence set forth in SEQ ID NO:4.

4. The ROR1 specific CAR according to claim 1, wherein said extracellular ligand binding-domain comprises VH and VL chains with at least 95 percent sequence identity to SEQ ID NO:53 and SEQ ID NO:58, respectively.

5. The ROR1 specific CAR according to claim 1, wherein said extracellular ligand binding-domain comprises humanized $V_H$ and $V_L$ chains from an H10 antibody.

6. The ROR1 specific CAR according to claim 5, wherein said humanized $V_H$ chain comprises the amino acid sequence encoded by SEQ ID NO:57, and said humanized $V_L$ chain comprises the amino acid sequence encoded by SEQ ID NO:62.

7. The ROR1 specific CAR according to claim 1, wherein said CAR comprises an amino acid sequence at least 95 percent identical to the sequence set forth in SEQ ID NO:117.

8. The ROR1 specific CAR according to claim 1, wherein said co-stimulatory domain comprises the amino acid sequence set forth in SEQ ID NO:8.

9. The ROR1 specific CAR according to claim 1, wherein said signaling domain comprises the amino acid sequence set forth in SEQ ID NO:9.

10. The ROR1 specific CAR according to claim 1, further comprising a signal peptide.

* * * * *

SEQUENCE LISTING

<160> NUMBER OF SEQ ID NOS: 143

<210> SEQ ID NO 1
<211> LENGTH: 20
<212> TYPE: PRT
<213> ORGANISM: artificial sequence
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
            20

-continued

<210> SEQ ID NO 2
<211> LENGTH: 21
<212> TYPE: PRT
<213> ORGANISM: artificial sequence
<220> FEATURE:
<223> OTHER INFORMATION: signal peptide

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
<220> FEATURE:
<223> OTHER INFORMATION: CD8alpha hinge

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg

```
               115                 120                 125
Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
<213> ORGANISM: homo sapiens
```

<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: linker sequence

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 118
<212> TYPE: PRT
<213> ORGANISM: artificial sequence
<220> FEATURE:
<223> OTHER INFORMATION: 2A2 heavy chain

<400> SEQUENCE: 11

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 12
<211> LENGTH: 8
<212> TYPE: PRT
<213> ORGANISM: artificial sequence
<220> FEATURE:
<223> OTHER INFORMATION: CDR1 of 2A2 heavy chain

<400> SEQUENCE: 12

Gly Tyr Thr Phe Ser Asp Tyr Glu
1               5

<210> SEQ ID NO 13
<211> LENGTH: 8
<212> TYPE: PRT
<213> ORGANISM: artificial sequence
<220> FEATURE:
<223> OTHER INFORMATION: CDR2 of 2A2 heavy chain

<400> SEQUENCE: 13

Ile Asp Pro Glu Thr Gly Gly Thr
1               5

<210> SEQ ID NO 14
<211> LENGTH: 11
<212> TYPE: PRT
<213> ORGANISM: artificial sequence
<220> FEATURE:
<223> OTHER INFORMATION: CDR3 of2A2 heavy chain

<400> SEQUENCE: 14

Thr Gly Tyr Tyr Asp Tyr Asp Ser Phe Thr Tyr
1               5                   10

<210> SEQ ID NO 15
<211> LENGTH: 107
<212> TYPE: PRT
<213> ORGANISM: artificial sequence
<220> FEATURE:
<223> OTHER INFORMATION: 2A2 light chain variable region

<400> SEQUENCE: 15

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
            100                 105

<210> SEQ ID NO 16
<211> LENGTH: 6
<212> TYPE: PRT
<213> ORGANISM: artificial sequence
<220> FEATURE:
<223> OTHER INFORMATION: CDR1 of 2A2 light chain

<400> SEQUENCE: 16

Gln Asn Val Asp Ala Ala
1               5

```
<210> SEQ ID NO 17
<211> LENGTH: 3
<212> TYPE: PRT
<213> ORGANISM: artificial sequence
<220> FEATURE:
<223> OTHER INFORMATION: CDR2 of 2A2 light chain

<400> SEQUENCE: 17

Ser Ala Ser
1

<210> SEQ ID NO 18
<211> LENGTH: 9
<212> TYPE: PRT
<213> ORGANISM: artificial sequence
<220> FEATURE:
<223> OTHER INFORMATION: CDR3 of2A2 light chain

<400> SEQUENCE: 18

Gln Gln Tyr Asp Ile Tyr Pro Tyr Thr
1               5

<210> SEQ ID NO 19
<211> LENGTH: 119
<212> TYPE: PRT
<213> ORGANISM: artificial sequence
<220> FEATURE:
<223> OTHER INFORMATION: 4A5 heavy chain

<400> SEQUENCE: 19

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 20
<211> LENGTH: 8
<212> TYPE: PRT
<213> ORGANISM: artificial sequence
<220> FEATURE:
<223> OTHER INFORMATION: CDR1 of 4A5 heavy chain

<400> SEQUENCE: 20

Gly Phe Thr Phe Ser Ser Tyr Ala
1               5

<210> SEQ ID NO 21
<211> LENGTH: 7
<212> TYPE: PRT
<213> ORGANISM: artificial sequence
<220> FEATURE:
<223> OTHER INFORMATION: CDR2 of 4A5 heavy chain
```

<400> SEQUENCE: 21

Ile Ser Arg Gly Gly Thr Thr
1               5

<210> SEQ ID NO 22
<211> LENGTH: 13
<212> TYPE: PRT
<213> ORGANISM: artificial sequence
<220> FEATURE:
<223> OTHER INFORMATION: CDR3 of 4A5 heavy chain

<400> SEQUENCE: 22

Gly Arg Tyr Asp Tyr Asp Gly Tyr Tyr Ala Met Asp Tyr
1               5                  10

<210> SEQ ID NO 23
<211> LENGTH: 107
<212> TYPE: PRT
<213> ORGANISM: artificial sequence
<220> FEATURE:
<223> OTHER INFORMATION: 4A5 light chain

<400> SEQUENCE: 23

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
                100                 105

<210> SEQ ID NO 24
<211> LENGTH: 6
<212> TYPE: PRT
<213> ORGANISM: artificial sequence
<220> FEATURE:
<223> OTHER INFORMATION: CDR1 of 4A5 light chain

<400> SEQUENCE: 24

Pro Asp Ile Asn Ser Tyr
1               5

<210> SEQ ID NO 25
<211> LENGTH: 3
<212> TYPE: PRT
<213> ORGANISM: artificial sequence
<220> FEATURE:
<223> OTHER INFORMATION: CDR2 of 4A5 light chain

<400> SEQUENCE: 25

Arg Ala Asn
1

<210> SEQ ID NO 26
<211> LENGTH: 9

```
<212> TYPE: PRT
<213> ORGANISM: artificial sequence
<220> FEATURE:
<223> OTHER INFORMATION: CDR3 of 4A5 light chain

<400> SEQUENCE: 26

Leu Gln Tyr Asp Glu Phe Pro Tyr Thr
1               5

<210> SEQ ID NO 27
<211> LENGTH: 117
<212> TYPE: PRT
<213> ORGANISM: artificial sequence
<220> FEATURE:
<223> OTHER INFORMATION: D10 heavy chain

<400> SEQUENCE: 27

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser
        115

<210> SEQ ID NO 28
<211> LENGTH: 8
<212> TYPE: PRT
<213> ORGANISM: artificial sequence
<220> FEATURE:
<223> OTHER INFORMATION: CDR1 of D10 heavy chain

<400> SEQUENCE: 28

Gly Phe Ser Leu Thr Ser Tyr Gly
1               5

<210> SEQ ID NO 29
<211> LENGTH: 7
<212> TYPE: PRT
<213> ORGANISM: artificial sequence
<220> FEATURE:
<223> OTHER INFORMATION: CDR2 of D10 heavy chain

<400> SEQUENCE: 29

Ile Trp Ala Gly Gly Phe Thr
1               5

<210> SEQ ID NO 30
<211> LENGTH: 11
<212> TYPE: PRT
<213> ORGANISM: artificial sequence
<220> FEATURE:
<223> OTHER INFORMATION: CDR3 of D10 heavy chain

<400> SEQUENCE: 30
```

```
Ala Arg Arg Gly Ser Ser Tyr Ser Met Asp Tyr
1               5                   10

<210> SEQ ID NO 31
<211> LENGTH: 117
<212> TYPE: PRT
<213> ORGANISM: artificial sequence
<220> FEATURE:
<223> OTHER INFORMATION: Humanized D10 heavy chain
<220> FEATURE:
<221> NAME/KEY: VARIANT
<222> LOCATION: (5)....(5)
<223> OTHER INFORMATION: /replace= " Lys"
<220> FEATURE:
<221> NAME/KEY: VARIANT
<222> LOCATION: (13)....(13)
<223> OTHER INFORMATION: /replace= " Ala "
<220> FEATURE:
<221> NAME/KEY: VARIANT
<222> LOCATION: (61)....(61)
<223> OTHER INFORMATION: /replace= " Ser"
<220> FEATURE:
<221> NAME/KEY: VARIANT
<222> LOCATION: (87)....(87)
<223> OTHER INFORMATION: /replace= " Asp"
<220> FEATURE:
<221> NAME/KEY: VARIANT
<222> LOCATION: (92)....(92)
<223> OTHER INFORMATION: /replace= " Met"

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Pro Ser Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Arg Gly Ser Ser Tyr Ser Met Asp Tyr Trp Gly Gln Gly Thr Leu
            100                 105                 110

Val Thr Val Ser Ser
        115

<210> SEQ ID NO 32
<211> LENGTH: 106
<212> TYPE: PRT
<213> ORGANISM: artificial sequence
<220> FEATURE:
<223> OTHER INFORMATION: D10 light chain

<400> SEQUENCE: 32

Glu Ile Val Leu Ser Gln Ser Pro Ala Ile Thr Ala Ala Ser Leu Gly
1               5                   10                  15

Gln Lys Val Thr Ile Thr Cys Ser Ala Ser Ser Asn Val Ser Tyr Ile
            20                  25                  30

His Trp Tyr Gln Gln Arg Ser Gly Thr Ser Pro Arg Pro Trp Ile Tyr
        35                  40                  45

Glu Ile Ser Lys Leu Ala Ser Gly Val Pro Val Arg Phe Ser Gly Ser
    50                  55                  60
```

```
Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Gln
            100                 105

<210> SEQ ID NO 33
<211> LENGTH: 5
<212> TYPE: PRT
<213> ORGANISM: artificial sequence
<220> FEATURE:
<223> OTHER INFORMATION: CDR1 of D10 light chain

<400> SEQUENCE: 33

Ser Asn Val Ser Tyr
1               5

<210> SEQ ID NO 34
<211> LENGTH: 3
<212> TYPE: PRT
<213> ORGANISM: artificial sequence
<220> FEATURE:
<223> OTHER INFORMATION: CDR2 of D10 light chain

<400> SEQUENCE: 34

Glu Ile Ser
1

<210> SEQ ID NO 35
<211> LENGTH: 9
<212> TYPE: PRT
<213> ORGANISM: artificial sequence
<220> FEATURE:
<223> OTHER INFORMATION: CDR3 of D10 light chain

<400> SEQUENCE: 35

Gln Gln Trp Asn Tyr Pro Leu Ile Thr
1               5

<210> SEQ ID NO 36
<211> LENGTH: 106
<212> TYPE: PRT
<213> ORGANISM: artificial sequence
<220> FEATURE:
<223> OTHER INFORMATION: Humanized D10 light chain
<220> FEATURE:
<221> NAME/KEY: VARIANT
<222> LOCATION: (5)....(5)
<223> OTHER INFORMATION: /replace= " Ser"
<220> FEATURE:
<221> NAME/KEY: VARIANT
<222> LOCATION: (34)....(34)
<223> OTHER INFORMATION: /replace= " Ser"
<220> FEATURE:
<221> NAME/KEY: VARIANT
<222> LOCATION: (50)....(50)
<223> OTHER INFORMATION: /replace= " Ser"
<220> FEATURE:
<221> NAME/KEY: VARIANT
<222> LOCATION: (66)....(66)
<223> OTHER INFORMATION: /replace= " Ser"
<220> FEATURE:
<221> NAME/KEY: VARIANT
<222> LOCATION: (90)....(90)
<223> OTHER INFORMATION: /replace= " Ala"
<220> FEATURE:
<221> NAME/KEY: VARIANT
<222> LOCATION: (95)....(95)
```

<223> OTHER INFORMATION: /replace= " Ile"

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Asn Val Ser Tyr Ile
            20                  25                  30

His Trp Tyr Gln Gln Lys Pro Gly Gln Ala Pro Arg Pro Trp Ile Tyr
        35                  40                  45

Glu Ile Ser Lys Leu Ala Thr Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Asn Tyr Pro Leu Ile Thr
                85                  90                  95

Phe Gly Gln Gly Thr Lys Leu Glu Ile Lys
            100                 105

<210> SEQ ID NO 37
<211> LENGTH: 119
<212> TYPE: PRT
<213> ORGANISM: artificial sequence
<220> FEATURE:
<223> OTHER INFORMATION: G6 heavy chain

<400> SEQUENCE: 37

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser
        115

<210> SEQ ID NO 38
<211> LENGTH: 8
<212> TYPE: PRT
<213> ORGANISM: artificial sequence
<220> FEATURE:
<223> OTHER INFORMATION: CDR1 of G6 heavy chain

<400> SEQUENCE: 38

Gly Phe Ala Phe Thr Gly Tyr Asn
1               5

<210> SEQ ID NO 39
<211> LENGTH: 8
<212> TYPE: PRT
<213> ORGANISM: artificial sequence
<220> FEATURE:
<223> OTHER INFORMATION: CDR2 of G6 heavy chain

<400> SEQUENCE: 39

Ile Asp Pro Tyr Tyr Gly Gly Ser
1               5

<210> SEQ ID NO 40
<211> LENGTH: 12
<212> TYPE: PRT
<213> ORGANISM: artificial sequence
<220> FEATURE:
<223> OTHER INFORMATION: CDR3 of G6 heavy chain

<400> SEQUENCE: 40

Ala Arg Ser Pro Gly Gly Asp Tyr Ala Met Asp Tyr
1               5                   10

<210> SEQ ID NO 41
<211> LENGTH: 107
<212> TYPE: PRT
<213> ORGANISM: artificial sequence
<220> FEATURE:
<223> OTHER INFORMATION: G6 light chain

<400> SEQUENCE: 41

Asp Ile Lys Met Thr Gln Ser Pro Ser Ser Met Tyr Ala Ser Val Gly
1               5                   10                  15

Glu Arg Val Thr Ile Thr Cys Lys Ala Ser Gln Gly Ile Asn Ser Tyr
            20                  25                  30

Ser Gly Trp Phe Gln Gln Lys Pro Gly Lys Ser Pro Lys Thr Leu Ile
        35                  40                  45

Tyr Arg Gly Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 42
<211> LENGTH: 6
<212> TYPE: PRT
<213> ORGANISM: artificial sequence
<220> FEATURE:
<223> OTHER INFORMATION: CDR1 of G6 light chain

<400> SEQUENCE: 42

Gln Gly Ile Asn Ser Tyr
1               5

<210> SEQ ID NO 43
<211> LENGTH: 3
<212> TYPE: PRT
<213> ORGANISM: artificial sequence
<220> FEATURE:
<223> OTHER INFORMATION: CDR2 of G6 light chain

<400> SEQUENCE: 43

Arg Gly Asn
1

<210> SEQ ID NO 44
<211> LENGTH: 9

```
<212> TYPE: PRT
<213> ORGANISM: artificial sequence
<220> FEATURE:
<223> OTHER INFORMATION: CDR3 of G6 light chain

<400> SEQUENCE: 44

Leu Gln Tyr Asp Glu Phe Pro Tyr Thr
1               5

<210> SEQ ID NO 45
<211> LENGTH: 118
<212> TYPE: PRT
<213> ORGANISM: artificial sequence
<220> FEATURE:
<223> OTHER INFORMATION: G3 heavy chain

<400> SEQUENCE: 45

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

Lys Ser Lys Ala Thr Leu Thr Ala Asp Thr Ser Ser Ser Thr Ala Tyr
65                  70                  75                  80

Met Gln Leu Ser Ser Leu Ala Ser Glu Asp Ser Ala Leu Tyr Tyr Cys
                85                  90                  95

Ala Arg Asp Gly Asn Tyr Tyr Ala Met Asp Tyr Trp Gly Gln Gly Thr
            100                 105                 110

Ser Val Thr Val Ser Ser
        115

<210> SEQ ID NO 46
<211> LENGTH: 8
<212> TYPE: PRT
<213> ORGANISM: artificial sequence
<220> FEATURE:
<223> OTHER INFORMATION: CDR1 of G3 heavy chain

<400> SEQUENCE: 46

Gly Tyr Asn Phe Thr Asn Tyr Trp
1               5

<210> SEQ ID NO 47
<211> LENGTH: 8
<212> TYPE: PRT
<213> ORGANISM: artificial sequence
<220> FEATURE:
<223> OTHER INFORMATION: CDR2 of G3 heavy chain

<400> SEQUENCE: 47

Ile Tyr Pro Gly Ser Gly Ser Thr
1               5

<210> SEQ ID NO 48
<211> LENGTH: 11
<212> TYPE: PRT
<213> ORGANISM: artificial sequence
<220> FEATURE:
<223> OTHER INFORMATION: CDR3 of G3 heavy chain

<400> SEQUENCE: 48
```

Ala Arg Asp Gly Asn Tyr Tyr Ala Met Asp Tyr
1               5                   10

<210> SEQ ID NO 49
<211> LENGTH: 108
<212> TYPE: PRT
<213> ORGANISM: artificial sequence
<220> FEATURE:
<223> OTHER INFORMATION: G3 light chain

<400> SEQUENCE: 49

Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ala Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Tyr Thr Phe Gly Gly Gly Thr Lys Leu Glu Ile Lys
            100                 105

<210> SEQ ID NO 50
<211> LENGTH: 6
<212> TYPE: PRT
<213> ORGANISM: artificial sequence
<220> FEATURE:
<223> OTHER INFORMATION: CDR1 of G6 light chain

<400> SEQUENCE: 50

Gln Asp Ile Asn Asn Tyr
1               5

<210> SEQ ID NO 51
<211> LENGTH: 3
<212> TYPE: PRT
<213> ORGANISM: artificial sequence
<220> FEATURE:
<223> OTHER INFORMATION: CDR2 of G6 light chain

<400> SEQUENCE: 51

Tyr Thr Ser
1

<210> SEQ ID NO 52
<211> LENGTH: 10
<212> TYPE: PRT
<213> ORGANISM: artificial sequence
<220> FEATURE:
<223> OTHER INFORMATION: CDR3 of G6 light chain

<400> SEQUENCE: 52

Gln Gln Gly Asn Thr Leu Pro Pro Tyr Thr
1               5                   10

<210> SEQ ID NO 53
<211> LENGTH: 118
<212> TYPE: PRT
<213> ORGANISM: artificial sequence

```
<220> FEATURE:
<223> OTHER INFORMATION: H10 heavy chain

<400> SEQUENCE: 53

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser
        115

<210> SEQ ID NO 54
<211> LENGTH: 8
<212> TYPE: PRT
<213> ORGANISM: artificial sequence
<220> FEATURE:
<223> OTHER INFORMATION: CDR1 of H10 heavy chain

<400> SEQUENCE: 54

Gly Phe Thr Phe Ser Ser Tyr Ala
1               5

<210> SEQ ID NO 55
<211> LENGTH: 7
<212> TYPE: PRT
<213> ORGANISM: artificial sequence
<220> FEATURE:
<223> OTHER INFORMATION: CDR2 of H10 heavy chain

<400> SEQUENCE: 55

Ile Ser Thr Gly Ala Ser Ala
1               5

<210> SEQ ID NO 56
<211> LENGTH: 12
<212> TYPE: PRT
<213> ORGANISM: artificial sequence
<220> FEATURE:
<223> OTHER INFORMATION: CDR3 of H10 heavy chain

<400> SEQUENCE: 56

Ala Arg Ile Thr Thr Ser Thr Trp Tyr Phe Asp Val
1               5                   10

<210> SEQ ID NO 57
<211> LENGTH: 118
<212> TYPE: PRT
<213> ORGANISM: artificial sequence
<220> FEATURE:
<223> OTHER INFORMATION: Humanized H10 heavy chain
<220> FEATURE:
<221> NAME/KEY: VARIANT
<222> LOCATION: (3)...(3)
<223> OTHER INFORMATION: /replace= " Lys"
```

<220> FEATURE:
<221> NAME/KEY: VARIANT
<222> LOCATION: (71)....(71)
<223> OTHER INFORMATION: /replace= " Pro"
<220> FEATURE:
<221> NAME/KEY: VARIANT
<222> LOCATION: (103)....(103)
<223> OTHER INFORMATION: /replace= " Met"

<400> SEQUENCE: 57

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Thr Gly Ala Ser Ala Tyr Phe Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ile Thr Thr Ser Thr Trp Tyr Phe Asp Val Trp Gly Gln Gly Thr
            100                 105                 110

Thr Val Thr Val Ser Ser
        115
```

<210> SEQ ID NO 58
<211> LENGTH: 107
<212> TYPE: PRT
<213> ORGANISM: artificial sequence
<220> FEATURE:
<223> OTHER INFORMATION: H10 light chain

<400> SEQUENCE: 58

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 59
<211> LENGTH: 6
<212> TYPE: PRT
<213> ORGANISM: artificial sequence
<220> FEATURE:
<223> OTHER INFORMATION: CDR1 of H10 light chain

<400> SEQUENCE: 59

```
Gln Asp Ile Asn Ser Tyr
1               5
```

<210> SEQ ID NO 60
<211> LENGTH: 3
<212> TYPE: PRT
<213> ORGANISM: artificial sequence
<220> FEATURE:
<223> OTHER INFORMATION: CDR2 of H10 light chain

<400> SEQUENCE: 60

Arg Ala Asn
1

<210> SEQ ID NO 61
<211> LENGTH: 9
<212> TYPE: PRT
<213> ORGANISM: artificial sequence
<220> FEATURE:
<223> OTHER INFORMATION: CDR3 of H10 light chain

<400> SEQUENCE: 61

Leu Gln Tyr Asp Glu Phe Pro Tyr Thr
1               5

<210> SEQ ID NO 62
<211> LENGTH: 107
<212> TYPE: PRT
<213> ORGANISM: artificial sequence
<220> FEATURE:
<223> OTHER INFORMATION: Humanized H10 light chain
<220> FEATURE:
<221> NAME/KEY: VARIANT
<222> LOCATION: (3)....(3)
<223> OTHER INFORMATION: /replace= " Lys"
<220> FEATURE:
<221> NAME/KEY: VARIANT
<222> LOCATION: (65)....(65)
<223> OTHER INFORMATION: /replace= " Val"
<220> FEATURE:
<221> NAME/KEY: VARIANT
<222> LOCATION: (90)....(05)
<223> OTHER INFORMATION: /replace= " Tyr"

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105

<210> SEQ ID NO 63
<211> LENGTH: 114
<212> TYPE: PRT
<213> ORGANISM: artificial sequence
<220> FEATURE:
<223> OTHER INFORMATION: 2A4 heavy chain

<400> SEQUENCE: 63

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser

<210> SEQ ID NO 64
<211> LENGTH: 8
<212> TYPE: PRT
<213> ORGANISM: artificial sequence
<220> FEATURE:
<223> OTHER INFORMATION: CDR1 of 2A4 heavy chain

<400> SEQUENCE: 64

Gly Tyr Thr Phe Thr Glu Tyr Thr
1               5

<210> SEQ ID NO 65
<211> LENGTH: 8
<212> TYPE: PRT
<213> ORGANISM: artificial sequence
<220> FEATURE:
<223> OTHER INFORMATION: CDR2 of 2A4 heavy chain

<400> SEQUENCE: 65

Ile Asn Pro Asn Asn Gly Gly Thr
1               5

<210> SEQ ID NO 66
<211> LENGTH: 7
<212> TYPE: PRT
<213> ORGANISM: artificial sequence
<220> FEATURE:
<223> OTHER INFORMATION: CDR3 of 2A4 heavy chain

<400> SEQUENCE: 66

Ala Leu Gln Gly Phe Ala Tyr
1               5

<210> SEQ ID NO 67
<211> LENGTH: 107
<212> TYPE: PRT
<213> ORGANISM: artificial sequence
<220> FEATURE:
<223> OTHER INFORMATION: 2A4 light chain

<400> SEQUENCE: 67

Met Glu Ile Glu Ile Thr Gln Thr Pro Ala Leu Met Ser Ala Ser Pro
1               5                   10                  15

Gly Glu Lys Val Thr Met Thr Cys Ser Ala Ser Ser Ser Val Ser Tyr
            20                  25                  30

Met Tyr Trp Tyr Gln Gln Lys Pro Arg Ser Ser Pro Lys Pro Trp Ile

```
                35                  40                  45
Tyr Leu Thr Ser Asn Leu Ala Ser Gly Val Pro Ala Arg Phe Ser Gly
         50                  55                  60
Ser Gly Ser Gly Thr Ser Tyr Ser Leu Thr Ile Ser Ser Met Glu Ala
 65                  70                  75                  80
Glu Asp Ala Ala Thr Tyr Tyr Cys Gln Gln Trp Ser Ser Asn Pro Tyr
                 85                  90                  95
Thr Phe Gly Gly Gly Thr Arg Leu Glu Leu Lys
            100                 105

<210> SEQ ID NO 68
<211> LENGTH: 5
<212> TYPE: PRT
<213> ORGANISM: artificial sequence
<220> FEATURE:
<223> OTHER INFORMATION: CDR1 of 2A4 light chain

<400> SEQUENCE: 68

Ser Ser Val Ser Tyr
 1               5

<210> SEQ ID NO 69
<211> LENGTH: 3
<212> TYPE: PRT
<213> ORGANISM: artificial sequence
<220> FEATURE:
<223> OTHER INFORMATION: CDR2 of 2A4 light chain

<400> SEQUENCE: 69

Leu Thr Ser
 1

<210> SEQ ID NO 70
<211> LENGTH: 9
<212> TYPE: PRT
<213> ORGANISM: artificial sequence
<220> FEATURE:
<223> OTHER INFORMATION: CDR3 of 2A4 light chain

<400> SEQUENCE: 70

Gln Gln Trp Ser Ser Asn Pro Tyr Thr
 1               5

<210> SEQ ID NO 71
<211> LENGTH: 119
<212> TYPE: PRT
<213> ORGANISM: artificial sequence
<220> FEATURE:
<223> OTHER INFORMATION: 1C11 heavy chain

<400> SEQUENCE: 71

Glu Val Lys Leu Gln Glu Ser Gly Ala Glu Leu Ala Arg Pro Gly Ala
 1               5                  10                  15
Ser Val Lys Met Ser Cys Lys Ala Ser Gly Tyr Thr Phe Thr Ser Tyr
                 20                  25                  30
Thr Met His Trp Val Lys Gln Arg Pro Gly Gln Gly Leu Glu Trp Ile
             35                  40                  45
Gly Tyr Ile Asn Pro Ser Ser Gly Tyr Thr Glu Tyr Asn Gln Lys Phe
         50                  55                  60
Lys Asp Lys Thr Thr Leu Thr Ala Asp Lys Ser Ser Ser Thr Ala Tyr
 65                  70                  75                  80
Met Gln Leu Ser Ser Leu Thr Ser Gly Asp Ser Ala Val Tyr Tyr Cys
```

```
                    85                  90                  95
Ala Arg Arg Val Leu Trp Leu Arg Arg Gly Asp Tyr Trp Gly Gln Gly
            100                 105                 110

Thr Ile Leu Thr Val Ser Ala
        115

<210> SEQ ID NO 72
<211> LENGTH: 8
<212> TYPE: PRT
<213> ORGANISM: artificial sequence
<220> FEATURE:
<223> OTHER INFORMATION: CDR1 of 1C11 heavy chain

<400> SEQUENCE: 72

Gly Tyr Thr Phe Thr Ser Tyr Thr
1               5

<210> SEQ ID NO 73
<211> LENGTH: 8
<212> TYPE: PRT
<213> ORGANISM: artificial sequence
<220> FEATURE:
<223> OTHER INFORMATION: CDR2 of 1C11 heavy chain

<400> SEQUENCE: 73

Ile Asn Pro Ser Ser Gly Tyr Thr
1               5

<210> SEQ ID NO 74
<211> LENGTH: 12
<212> TYPE: PRT
<213> ORGANISM: artificial sequence
<220> FEATURE:
<223> OTHER INFORMATION: CDR3 of 1C11 heavy chain

<400> SEQUENCE: 74

Ala Arg Arg Val Leu Trp Leu Arg Arg Gly Asp Tyr
1               5                   10

<210> SEQ ID NO 75
<211> LENGTH: 108
<212> TYPE: PRT
<213> ORGANISM: artificial sequence
<220> FEATURE:
<223> OTHER INFORMATION: 1C11 light chain

<400> SEQUENCE: 75

Met Glu Val Leu Ile Thr Gln Thr Pro Ser Ser Leu Ser Ala Ser Leu
1               5                   10                  15

Gly Glu Arg Val Ser Leu Thr Cys Arg Ala Ser Gln Asp Ile Gly Ser
            20                  25                  30

Ser Leu Asn Trp Leu Gln Gln Glu Pro Asp Gly Thr Ile Lys Arg Leu
        35                  40                  45

Ile Tyr Ala Thr Ser Ser Leu Asp Ser Gly Val Pro Lys Arg Phe Ser
    50                  55                  60

Gly Ser Arg Ser Gly Ser Asp Tyr Ser Leu Thr Ile Ser Ser Leu Glu
65                  70                  75                  80

Ser Glu Asp Phe Val Asp Tyr Tyr Cys Leu Gln Tyr Ala Ser Ser Pro
                85                  90                  95

Tyr Thr Phe Gly Gly Gly Thr Lys Leu Glu Leu Lys
            100                 105
```

```
<210> SEQ ID NO 76
<211> LENGTH: 6
<212> TYPE: PRT
<213> ORGANISM: artificial sequence
<220> FEATURE:
<223> OTHER INFORMATION: CDR1 of 1C11 light chain

<400> SEQUENCE: 76

Gln Asp Ile Gly Ser Ser
1               5

<210> SEQ ID NO 77
<211> LENGTH: 3
<212> TYPE: PRT
<213> ORGANISM: artificial sequence
<220> FEATURE:
<223> OTHER INFORMATION: CDR2 of 1C11 light chain

<400> SEQUENCE: 77

Ala Thr Ser
1

<210> SEQ ID NO 78
<211> LENGTH: 7
<212> TYPE: PRT
<213> ORGANISM: artificial sequence
<220> FEATURE:
<223> OTHER INFORMATION: CDR3 of 1C11 light chain

<400> SEQUENCE: 78

Leu Gln Tyr Ala Ser Ser Pro
1               5

<210> SEQ ID NO 79
<211> LENGTH: 434
<212> TYPE: PRT
<213> ORGANISM: artificial sequence
<220> FEATURE:
<223> OTHER INFORMATION: 2A2-v1 polypeptide CAR sequence

<400> SEQUENCE: 79

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Asp Ile Val Met Thr Gln Ser Gln Lys Ile Met
    130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
```

```
                165                 170                 175
Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
        195                 200                 205

Ser Asn Met Gln Ser Glu Asp Leu Ala Asp Tyr Phe Cys Gln Gln Tyr
    210                 215                 220

Asp Ile Tyr Pro Tyr Thr Phe Gly Gly Gly Thr Lys Leu Glu Ile Lys
225                 230                 235                 240

Gly Leu Ala Val Ser Thr Ile Ser Ser Phe Phe Pro Pro Gly Tyr Gln
                245                 250                 255

Ile Tyr Ile Trp Ala Pro Leu Ala Gly Thr Cys Gly Val Leu Leu Leu
            260                 265                 270

Ser Leu Val Ile Thr Leu Tyr Cys Lys Arg Gly Arg Lys Lys Leu Leu
        275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 80
<211> LENGTH: 437
<212> TYPE: PRT
<213> ORGANISM: artificial sequence
<220> FEATURE:
<223> OTHER INFORMATION: 2A2-v2 polypeptide CAR sequence

<400> SEQUENCE: 80

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95
```

```
Thr Gly Tyr Tyr Asp Tyr Asp Ser Phe Thr Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Asp Ile Val Met Thr Gln Ser Gln Lys Ile Met
        130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
                165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
            195                 200                 205

Ser Asn Met Gln Ser Glu Asp Leu Ala Asp Tyr Phe Cys Gln Gln Tyr
            210                 215                 220

Asp Ile Tyr Pro Tyr Thr Phe Gly Gly Gly Thr Lys Leu Glu Ile Lys
225                 230                 235                 240

Gly Leu Ala Val Ser Thr Ile Ser Ser Phe Phe Pro Pro Gly Tyr Gln
                245                 250                 255

Ile Ile Ser Phe Phe Leu Ala Leu Thr Ser Thr Ala Leu Leu Phe Leu
            260                 265                 270

Leu Phe Phe Leu Thr Leu Arg Phe Ser Val Val Lys Arg Gly Arg Lys
            275                 280                 285

Lys Leu Leu Tyr Ile Phe Lys Gln Pro Phe Met Arg Pro Val Gln Thr
            290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
            355                 360                 365

Glu Met Gly Gly Lys Pro Arg Arg Lys Asn Pro Gln Glu Gly Leu Tyr
            370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
        435

<210> SEQ ID NO 81
<211> LENGTH: 463
<212> TYPE: PRT
<213> ORGANISM: artificial sequence
<220> FEATURE:
<223> OTHER INFORMATION: 2A2-v3 polypeptide CAR sequence

<400> SEQUENCE: 81

Gln Val Gln Leu Gln Gln Ser Gly Ala Glu Leu Val Arg Pro Gly Ala
1               5                   10                  15
```

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
            35                  40                  45

Gly Ala Ile Asp Pro Glu Thr Gly Gly Thr Ala Tyr Asn Gln Lys Phe
 50                  55                  60

Lys Gly Lys Ala Ile Leu Thr Ala Asp Lys Ser Ser Thr Ala Tyr
 65                  70                  75                  80

Met Glu Leu Arg Ser Leu Thr Ser Glu Asp Ser Ala Val Tyr Tyr Cys
            85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Ser Gly Gly Gly Ser
            115                 120                 125

Gly Gly Gly Gly Ser Asp Ile Val Met Thr Gln Ser Gln Lys Ile Met
 130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
            165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
            195                 200                 205

Ser Asn Met Gln Ser Glu Asp Leu Ala Asp Tyr Phe Cys Gln Gln Tyr
            210                 215                 220

Asp Ile Tyr Pro Tyr Thr Phe Gly Gly Gly Thr Lys Leu Glu Ile Lys
225                 230                 235                 240

Thr Thr Thr Pro Ala Pro Arg Pro Pro Thr Pro Ala Pro Thr Ile Ala
            245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
            275                 280                 285

Trp Ala Pro Leu Ala Gly Thr Cys Gly Val Leu Leu Leu Ser Leu Val
            290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
            325                 330                 335

Cys Ser Cys Arg Phe Pro Glu Glu Glu Glu Gly Gly Cys Glu Leu Arg
            340                 345                 350

Val Lys Phe Ser Arg Ser Ala Asp Ala Pro Ala Tyr Gln Gln Gly Gln
            355                 360                 365

Asn Gln Leu Tyr Asn Glu Leu Asn Leu Gly Arg Arg Glu Glu Tyr Asp
            370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
            405                 410                 415

Lys Met Ala Glu Ala Tyr Ser Glu Ile Gly Met Lys Gly Glu Arg Arg
            420                 425                 430

-continued

Arg Gly Lys Gly His Asp Gly Leu Tyr Gln Gly Leu Ser Thr Ala Thr
    435                 440                 445

Lys Asp Thr Tyr Asp Ala Leu His Met Gln Ala Leu Pro Pro Arg
450                 455                 460

<210> SEQ ID NO 82
<211> LENGTH: 466
<212> TYPE: PRT
<213> ORGANISM: artificial sequence
<220> FEATURE:
<223> OTHER INFORMATION: 2A2-v4 polypeptide CAR sequence

<400> SEQUENCE: 82

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Ile Val Met Thr Gln Ser Gln Lys Ile Met
    130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
                165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
        195                 200                 205

Ser Asn Met Gln Ser Glu Asp Leu Ala Asp Tyr Phe Cys Gln Gln Tyr
    210                 215                 220

Asp Ile Tyr Pro Tyr Thr Phe Gly Gly Gly Thr Lys Leu Glu Ile Lys
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Ile Ser
        275                 280                 285

Phe Phe Leu Ala Leu Thr Ser Thr Ala Leu Leu Phe Leu Leu Phe Phe
    290                 295                 300

Leu Thr Leu Arg Phe Ser Val Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

```
Glu Asp Gly Cys Ser Cys Arg Phe Pro Glu Glu Glu Gly Cys
                340                 345                 350

Glu Leu Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
        370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 83
<211> LENGTH: 649
<212> TYPE: PRT
<213> ORGANISM: artificial sequence
<220> FEATURE:
<223> OTHER INFORMATION: 2A2-v5 polypeptide CAR sequence

<400> SEQUENCE: 83

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Ile Val Met Thr Gln Ser Gln Lys Ile Met
    130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
                165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
        195                 200                 205

Ser Asn Met Gln Ser Glu Asp Leu Ala Asp Tyr Phe Cys Gln Gln Tyr
    210                 215                 220
```

-continued

Asp Ile Tyr Pro Tyr Thr Phe Gly Gly Gly Thr Lys Leu Glu Ile Lys
225                 230                 235                 240

Glu Pro Lys Ser Pro Asp Lys Thr His Thr Cys Pro Pro Cys Pro Ala
            245                 250                 255

Pro Pro Val Ala Gly Pro Ser Val Phe Leu Phe Pro Pro Lys Pro Lys
        260                 265                 270

Asp Thr Leu Met Ile Ala Arg Thr Pro Glu Val Thr Cys Val Val Val
    275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys Ile Tyr Ile Trp Ala Pro Leu Ala Gly
465                 470                 475                 480

Thr Cys Gly Val Leu Leu Leu Ser Leu Val Ile Thr Leu Tyr Cys Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Arg Val Lys Phe Ser Arg Ser
530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
        595                 600                 605

Ser Glu Ile Gly Met Lys Gly Glu Arg Arg Gly Lys Gly His Asp
    610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg

<210> SEQ ID NO 84
<211> LENGTH: 652
<212> TYPE: PRT
<213> ORGANISM: artificial sequence
<220> FEATURE:
<223> OTHER INFORMATION: 2A2-v6 polypeptide CAR sequence

<400> SEQUENCE: 84

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Ser Gly Gly Gly Ser
        115                 120                 125

Gly Gly Gly Gly Ser Asp Ile Val Met Thr Gln Ser Gln Lys Ile Met
    130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
                165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
        195                 200                 205

Ser Asn Met Gln Ser Glu Asp Leu Ala Asp Tyr Phe Cys Gln Gln Tyr
    210                 215                 220

Asp Ile Tyr Pro Tyr Thr Phe Gly Gly Gly Thr Lys Leu Glu Ile Lys
225                 230                 235                 240

Glu Pro Lys Ser Pro Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ala Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg

```
                355                 360                 365
Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys Ile Ile Ser Phe Phe Leu Ala Leu Thr
465                 470                 475                 480

Ser Thr Ala Leu Leu Phe Leu Leu Phe Phe Leu Thr Leu Arg Phe Ser
                485                 490                 495

Val Val Lys Arg Gly Arg Lys Lys Leu Leu Tyr Ile Phe Lys Gln Pro
            500                 505                 510

Phe Met Arg Pro Val Gln Thr Thr Gln Glu Glu Asp Gly Cys Ser Cys
        515                 520                 525

Arg Phe Pro Glu Glu Glu Glu Gly Gly Cys Glu Leu Arg Val Lys Phe
    530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
            580                 585                 590

Asn Pro Gln Glu Gly Leu Tyr Asn Glu Leu Gln Lys Asp Lys Met Ala
        595                 600                 605

Glu Ala Tyr Ser Glu Ile Gly Met Lys Gly Glu Arg Arg Arg Gly Lys
    610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650

<210> SEQ ID NO 85
<211> LENGTH: 435
<212> TYPE: PRT
<213> ORGANISM: artificial sequence
<220> FEATURE:
<223> OTHER INFORMATION: 4A5-v1 polypeptide CAR sequence

<400> SEQUENCE: 85

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
```

```
                  65                  70                  75                  80
Gln Met Ser Ser Leu Arg Ser Glu Asp Thr Ala Met Tyr Tyr Cys Gly
                    85                  90                  95

Arg Tyr Asp Tyr Asp Gly Tyr Tyr Ala Met Asp Tyr Trp Gly Gln Gly
                100                 105                 110

Thr Ser Val Thr Val Ser Ser Gly Gly Gly Ser Gly Gly Gly
                115                 120                 125

Ser Gly Gly Gly Ser Asp Ile Lys Met Thr Gln Ser Pro Ser Ser
            130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
                180                 185                 190

Pro Ser Arg Phe Ser Gly Gly Ser Gly Gln Asp Tyr Ser Leu Thr
                195                 200                 205

Ile Asn Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Met
225                 230                 235                 240

Lys Gly Leu Ala Val Ser Thr Ile Ser Ser Phe Phe Pro Gly Tyr
                245                 250                 255

Gln Ile Tyr Ile Trp Ala Pro Leu Ala Gly Thr Cys Gly Val Leu Leu
        260                 265                 270

Leu Ser Leu Val Ile Thr Leu Tyr Cys Lys Arg Gly Arg Lys Lys Leu
    275                 280                 285

Leu Tyr Ile Phe Lys Gln Pro Phe Met Arg Pro Val Gln Thr Thr Gln
        290                 295                 300

Glu Glu Asp Gly Cys Ser Cys Arg Phe Pro Glu Glu Glu Gly Gly
305                 310                 315                 320

Cys Glu Leu Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Gly Arg Asp Pro Glu Met
                355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
                420                 425                 430

Pro Pro Arg
        435

<210> SEQ ID NO 86
<211> LENGTH: 438
<212> TYPE: PRT
<213> ORGANISM: artificial sequence
<220> FEATURE:
<223> OTHER INFORMATION: 4A5-v2 polypeptide CAR sequence
```

<400> SEQUENCE: 86

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Gly Gly Ser Gly Gly Gly
        115                 120                 125

Ser Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Gly Ser Gly Gln Asp Tyr Ser Leu Thr
        195                 200                 205

Ile Asn Ser Leu Glu Tyr Glu Asp Met Gly Ile Tyr Tyr Cys Leu Gln
    210                 215                 220

Tyr Asp Glu Phe Pro Tyr Thr Phe Gly Gly Thr Lys Leu Glu Met
225                 230                 235                 240

Lys Gly Leu Ala Val Ser Thr Ile Ser Ser Phe Phe Pro Pro Gly Tyr
                245                 250                 255

Gln Ile Ile Ser Phe Phe Leu Ala Leu Thr Ser Thr Ala Leu Leu Phe
            260                 265                 270

Leu Leu Phe Phe Leu Thr Leu Arg Phe Ser Val Val Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Gly Arg Asp
        355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

-continued

```
Gln Gly Leu Ser Thr Ala Thr Lys Asp Thr Tyr Asp Ala Leu His Met
            420                 425                 430

Gln Ala Leu Pro Pro Arg
            435

<210> SEQ ID NO 87
<211> LENGTH: 464
<212> TYPE: PRT
<213> ORGANISM: artificial sequence
<220> FEATURE:
<223> OTHER INFORMATION: 4A5-v3 polypeptide CAR sequence

<400> SEQUENCE: 87

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Gly Ser Gly Gln Asp Tyr Ser Leu Thr
        195                 200                 205

Ile Asn Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Met
225                 230                 235                 240

Lys Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
    290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335
```

```
Gly Cys Ser Cys Arg Phe Pro Glu Glu Glu Gly Cys Glu Leu
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
            450                 455                 460

<210> SEQ ID NO 88
<211> LENGTH: 467
<212> TYPE: PRT
<213> ORGANISM: artificial sequence
<220> FEATURE:
<223> OTHER INFORMATION: 4A5-v4 polypeptide CAR sequence

<400> SEQUENCE: 88

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Gly Ser Gly Gln Asp Tyr Ser Leu Thr
        195                 200                 205

Ile Asn Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Met
225                 230                 235                 240
```

Lys Thr Thr Thr Pro Ala Pro Arg Pro Pro Thr Pro Ala Pro Thr Ile
            245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Ile
            275                 280                 285

Ser Phe Phe Leu Ala Leu Thr Ser Thr Ala Leu Leu Phe Leu Leu Phe
290                 295                 300

Phe Leu Thr Leu Arg Phe Ser Val Val Lys Arg Gly Arg Lys Lys Leu
305                 310                 315                 320

Leu Tyr Ile Phe Lys Gln Pro Phe Met Arg Pro Val Gln Thr Thr Gln
            325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
            355                 360                 365

Gln Gln Gly Gln Asn Gln Leu Tyr Asn Glu Leu Asn Leu Gly Arg Arg
            370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
            405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
            450                 455                 460

Pro Pro Arg
465

<210> SEQ ID NO 89
<211> LENGTH: 650
<212> TYPE: PRT
<213> ORGANISM: artificial sequence
<220> FEATURE:
<223> OTHER INFORMATION: 4A5-v5 polypeptide CAR sequence

<400> SEQUENCE: 89

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
            35                  40                  45

Ala Ser Ile Ser Arg Gly Gly Thr Thr Tyr Tyr Pro Asp Ser Val Lys
            50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
            85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Gly Gly Gly Ser Gly Gly Gly Gly
            115                 120                 125

-continued

```
Ser Gly Gly Gly Gly Ser Asp Ile Lys Met Thr Gln Ser Pro Ser Ser
130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Gly Ser Gly Gln Asp Tyr Ser Leu Thr
        195                 200                 205

Ile Asn Ser Leu Glu Tyr Glu Asp Met Gly Ile Tyr Tyr Cys Leu Gln
210                 215                 220

Tyr Asp Glu Phe Pro Tyr Thr Phe Gly Gly Gly Thr Lys Leu Glu Met
225                 230                 235                 240

Lys Glu Pro Lys Ser Pro Asp Lys Thr His Thr Cys Pro Pro Cys Pro
                245                 250                 255

Ala Pro Pro Val Ala Gly Pro Ser Val Phe Leu Phe Pro Pro Lys Pro
                260                 265                 270

Lys Asp Thr Leu Met Ile Ala Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys Ile Tyr Ile Trp Ala Pro Leu Ala
465                 470                 475                 480

Gly Thr Cys Gly Val Leu Leu Leu Ser Leu Val Ile Thr Leu Tyr Cys
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
530                 535                 540
```

```
Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
            565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
            595                 600                 605

Tyr Ser Glu Ile Gly Met Lys Gly Glu Arg Arg Arg Gly Lys Gly His
            610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
            645                 650

<210> SEQ ID NO 90
<211> LENGTH: 653
<212> TYPE: PRT
<213> ORGANISM: artificial sequence
<220> FEATURE:
<223> OTHER INFORMATION: 4A5-v6 polypeptide CAR sequence

<400> SEQUENCE: 90

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Leu Gly Glu Arg Val Thr Ile Thr Cys Lys Ala Ser
145                 150                 155                 160

Pro Asp Ile Asn Ser Tyr Leu Ser Trp Phe Gln Gln Lys Pro Gly Lys
                165                 170                 175

Ser Pro Lys Thr Leu Ile Tyr Arg Ala Asn Arg Leu Val Asp Gly Val
            180                 185                 190

Pro Ser Arg Phe Ser Gly Gly Ser Gly Gln Asp Tyr Ser Leu Thr
        195                 200                 205

Ile Asn Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Met
225                 230                 235                 240

Lys Glu Pro Lys Ser Pro Asp Lys Thr His Thr Cys Pro Pro Cys Pro
                245                 250                 255
```

-continued

```
Ala Pro Pro Val Ala Gly Pro Ser Val Phe Leu Phe Pro Pro Lys Pro
                260                 265                 270

Lys Asp Thr Leu Met Ile Ala Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Lys Ile Ile Ser Phe Phe Leu Ala Leu
465                 470                 475                 480

Thr Ser Thr Ala Leu Leu Phe Leu Leu Phe Phe Leu Thr Leu Arg Phe
                485                 490                 495

Ser Val Val Lys Arg Gly Arg Lys Lys Leu Leu Tyr Ile Phe Lys Gln
            500                 505                 510

Pro Phe Met Arg Pro Val Gln Thr Thr Gln Glu Glu Asp Gly Cys Ser
        515                 520                 525

Cys Arg Phe Pro Glu Glu Glu Glu Gly Gly Cys Glu Leu Arg Val Lys
530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
        595                 600                 605

Ala Glu Ala Tyr Ser Glu Ile Gly Met Lys Gly Glu Arg Arg Arg Gly
610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 91
<211> LENGTH: 432
<212> TYPE: PRT
```

<213> ORGANISM: artificial sequence
<220> FEATURE:
<223> OTHER INFORMATION: D10-v1 polypeptide CAR sequence

<400> SEQUENCE: 91

```
Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Ser Gln Ser Pro Ala Ile Thr Ala
    130                 135                 140

Ala Ser Leu Gly Gln Lys Val Thr Ile Thr Cys Ser Ala Ser Ser Asn
145                 150                 155                 160

Val Ser Tyr Ile His Trp Tyr Gln Gln Arg Ser Gly Thr Ser Pro Arg
                165                 170                 175

Pro Trp Ile Tyr Glu Ile Ser Lys Leu Ala Ser Gly Val Pro Val Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Ile Tyr Tyr Cys Gln Gln Trp Asn Tyr
    210                 215                 220

Pro Leu Ile Thr Phe Gly Ser Gly Thr Lys Leu Glu Ile Gln Gly Leu
225                 230                 235                 240

Ala Val Ser Thr Ile Ser Ser Phe Phe Pro Pro Gly Tyr Gln Ile Tyr
                245                 250                 255

Ile Trp Ala Pro Leu Ala Gly Thr Cys Gly Val Leu Leu Leu Ser Leu
            260                 265                 270

Val Ile Thr Leu Tyr Cys Lys Arg Gly Arg Lys Lys Leu Leu Tyr Ile
        275                 280                 285

Phe Lys Gln Pro Phe Met Arg Pro Val Gln Thr Thr Gln Glu Glu Asp
    290                 295                 300

Gly Cys Ser Cys Arg Phe Pro Glu Glu Glu Gly Gly Cys Glu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
```

-continued

```
            385                 390                 395                 400
Arg Arg Gly Lys Gly His Asp Gly Leu Tyr Gln Gly Leu Ser Thr Ala
                    405                 410                 415
Thr Lys Asp Thr Tyr Asp Ala Leu His Met Gln Ala Leu Pro Pro Arg
                420                 425                 430

<210> SEQ ID NO 92
<211> LENGTH: 435
<212> TYPE: PRT
<213> ORGANISM: artificial sequence
<220> FEATURE:
<223> OTHER INFORMATION: D10-v2 polypeptide CAR sequence

<400> SEQUENCE: 92

Gln Val Gln Leu Lys Glu Ser Gly Pro Gly Leu Val Ala Pro Ser Gln
1               5                   10                  15
Thr Leu Ser Ile Thr Cys Thr Val Ser Gly Phe Ser Leu Thr Ser Tyr
            20                  25                  30
Gly Val His Trp Val Arg Gln Pro Pro Gly Lys Gly Leu Glu Trp Leu
        35                  40                  45
Gly Val Ile Trp Ala Gly Gly Phe Thr Asn Tyr Asn Ser Ala Leu Lys
    50                  55                  60
Ser Arg Leu Ser Ile Ser Lys Asp Asn Ser Lys Ser Gln Val Leu Leu
65                  70                  75                  80
Lys Met Thr Ser Leu Gln Thr Asp Asp Thr Ala Met Tyr Tyr Cys Ala
                85                  90                  95
Arg Arg Gly Ser Ser Tyr Ser Met Asp Tyr Trp Gly Gln Gly Thr Ser
            100                 105                 110
Val Thr Val Ser Ser Gly Gly Gly Gly Ser Gly Gly Gly Gly Ser Gly
        115                 120                 125
Gly Gly Gly Ser Glu Ile Val Leu Ser Gln Ser Pro Ala Ile Thr Ala
    130                 135                 140
Ala Ser Leu Gly Gln Lys Val Thr Ile Thr Cys Ser Ala Ser Ser Asn
145                 150                 155                 160
Val Ser Tyr Ile His Trp Tyr Gln Gln Arg Ser Gly Thr Ser Pro Arg
                165                 170                 175
Pro Trp Ile Tyr Glu Ile Ser Lys Leu Ala Ser Gly Val Pro Val Arg
            180                 185                 190
Phe Ser Gly Ser Gly Ser Gly Thr Ser Tyr Ser Leu Thr Ile Ser Ser
        195                 200                 205
Met Glu Ala Glu Asp Ala Ala Ile Tyr Tyr Cys Gln Gln Trp Asn Tyr
    210                 215                 220
Pro Leu Ile Thr Phe Gly Ser Gly Thr Lys Leu Glu Ile Gln Gly Leu
225                 230                 235                 240
Ala Val Ser Thr Ile Ser Ser Phe Phe Pro Gly Tyr Gln Ile Ile
                245                 250                 255
Ser Phe Phe Leu Ala Leu Thr Ser Thr Ala Leu Leu Phe Leu Leu Phe
            260                 265                 270
Phe Leu Thr Leu Arg Phe Ser Val Val Lys Arg Gly Arg Lys Lys Leu
        275                 280                 285
Leu Tyr Ile Phe Lys Gln Pro Phe Met Arg Pro Val Gln Thr Thr Gln
    290                 295                 300
Glu Glu Asp Gly Cys Ser Cys Arg Phe Pro Glu Glu Glu Glu Gly Gly
305                 310                 315                 320
Cys Glu Leu Arg Val Lys Phe Ser Arg Ser Ala Asp Ala Pro Ala Tyr
```

```
                      325                 330                 335
    Gln Gln Gly Gln Asn Gln Leu Tyr Asn Glu Leu Asn Leu Gly Arg Arg
                340                 345                 350

Glu Glu Tyr Asp Val Leu Asp Lys Arg Arg Gly Arg Asp Pro Glu Met
                355                 360                 365

Gly Gly Lys Pro Arg Arg Lys Asn Pro Gln Glu Gly Leu Tyr Asn Glu
                370                 375                 380

Leu Gln Lys Asp Lys Met Ala Glu Ala Tyr Ser Glu Ile Gly Met Lys
    385                 390                 395                 400

Gly Glu Arg Arg Arg Gly Lys Gly His Asp Gly Leu Tyr Gln Gly Leu
                    405                 410                 415

Ser Thr Ala Thr Lys Asp Thr Tyr Asp Ala Leu His Met Gln Ala Leu
                    420                 425                 430

Pro Pro Arg
            435

<210> SEQ ID NO 93
<211> LENGTH: 461
<212> TYPE: PRT
<213> ORGANISM: artificial sequence
<220> FEATURE:
<223> OTHER INFORMATION: D10-v3 polypeptide CAR sequence

<400> SEQUENCE: 93

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Ser Gln Ser Pro Ala Ile Thr Ala
    130                 135                 140

Ala Ser Leu Gly Gln Lys Val Thr Ile Thr Cys Ser Ala Ser Ser Asn
145                 150                 155                 160

Val Ser Tyr Ile His Trp Tyr Gln Gln Arg Ser Gly Thr Ser Pro Arg
                165                 170                 175

Pro Trp Ile Tyr Glu Ile Ser Lys Leu Ala Ser Gly Val Pro Val Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Ile Tyr Tyr Cys Gln Gln Trp Asn Tyr
    210                 215                 220

Pro Leu Ile Thr Phe Gly Ser Gly Thr Lys Leu Glu Ile Gln Thr Thr
225                 230                 235                 240

Thr Pro Ala Pro Arg Pro Pro Thr Pro Ala Pro Thr Ile Ala Ser Gln
```

```
            245                 250                 255
Pro Leu Ser Leu Arg Pro Glu Ala Cys Arg Pro Ala Ala Gly Gly Ala
            260                 265                 270

Val His Thr Arg Gly Leu Asp Phe Ala Cys Asp Ile Tyr Ile Trp Ala
            275                 280                 285

Pro Leu Ala Gly Thr Cys Gly Val Leu Leu Leu Ser Leu Val Ile Thr
            290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
            370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
            435                 440                 445

Thr Tyr Asp Ala Leu His Met Gln Ala Leu Pro Pro Arg
            450                 455                 460

<210> SEQ ID NO 94
<211> LENGTH: 464
<212> TYPE: PRT
<213> ORGANISM: artificial sequence
<220> FEATURE:
<223> OTHER INFORMATION: D10-v4 polypeptide CAR sequence

<400> SEQUENCE: 94

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser Gly Gly Gly Gly Ser Gly Gly Gly Ser Gly
            115                 120                 125

Gly Gly Gly Ser Glu Ile Val Leu Ser Gln Ser Pro Ala Ile Thr Ala
        130                 135                 140

Ala Ser Leu Gly Gln Lys Val Thr Ile Thr Cys Ser Ala Ser Ser Asn
```

```
            145                 150                 155                 160
Val Ser Tyr Ile His Trp Tyr Gln Gln Arg Ser Gly Thr Ser Pro Arg
                165                 170                 175

Pro Trp Ile Tyr Glu Ile Ser Lys Leu Ala Ser Gly Val Pro Val Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Ile Tyr Tyr Cys Gln Gln Trp Asn Tyr
    210                 215                 220

Pro Leu Ile Thr Phe Gly Ser Gly Thr Lys Leu Glu Ile Gln Thr Thr
225                 230                 235                 240

Thr Pro Ala Pro Arg Pro Pro Thr Pro Ala Pro Thr Ile Ala Ser Gln
                245                 250                 255

Pro Leu Ser Leu Arg Pro Glu Ala Cys Arg Pro Ala Ala Gly Gly Ala
            260                 265                 270

Val His Thr Arg Gly Leu Asp Phe Ala Cys Asp Ile Ile Ser Phe Phe
        275                 280                 285

Leu Ala Leu Thr Ser Thr Ala Leu Leu Phe Leu Leu Phe Phe Leu Thr
    290                 295                 300

Leu Arg Phe Ser Val Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 95
<211> LENGTH: 647
<212> TYPE: PRT
<213> ORGANISM: artificial sequence
<220> FEATURE:
<223> OTHER INFORMATION: D10-v5 polypeptide CAR sequence

<400> SEQUENCE: 95

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
```

-continued

```
            50                  55                  60
Ser Arg Leu Ser Ile Ser Lys Asp Asn Ser Lys Ser Gln Val Leu Leu
 65                  70                  75                  80

Lys Met Thr Ser Leu Gln Thr Asp Asp Thr Ala Met Tyr Tyr Cys Ala
                 85                  90                  95

Arg Arg Gly Ser Ser Tyr Ser Met Asp Tyr Trp Gly Gln Gly Thr Ser
                100                 105                 110

Val Thr Val Ser Ser Gly Gly Gly Gly Ser Gly Gly Gly Gly Ser Gly
                115                 120                 125

Gly Gly Gly Ser Glu Ile Val Leu Ser Gln Ser Pro Ala Ile Thr Ala
            130                 135                 140

Ala Ser Leu Gly Gln Lys Val Thr Ile Thr Cys Ser Ala Ser Ser Asn
145                 150                 155                 160

Val Ser Tyr Ile His Trp Tyr Gln Gln Arg Ser Gly Thr Ser Pro Arg
                165                 170                 175

Pro Trp Ile Tyr Glu Ile Ser Lys Leu Ala Ser Gly Val Pro Val Arg
                180                 185                 190

Phe Ser Gly Ser Gly Ser Gly Thr Ser Tyr Ser Leu Thr Ile Ser Ser
                195                 200                 205

Met Glu Ala Glu Asp Ala Ala Ile Tyr Tyr Cys Gln Gln Trp Asn Tyr
            210                 215                 220

Pro Leu Ile Thr Phe Gly Ser Gly Thr Lys Leu Glu Ile Gln Glu Pro
225                 230                 235                 240

Lys Ser Pro Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ala Arg Thr Pro Glu Val Thr Cys Val Val Val Asp Val
                275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
            450                 455                 460

Leu Ser Pro Gly Lys Ile Tyr Ile Trp Ala Pro Leu Ala Gly Thr Cys
465                 470                 475                 480
```

```
Gly Val Leu Leu Leu Ser Leu Val Ile Thr Leu Tyr Cys Lys Arg Gly
                485                 490                 495

Arg Lys Lys Leu Leu Tyr Ile Phe Lys Gln Pro Phe Met Arg Pro Val
            500                 505                 510

Gln Thr Thr Gln Glu Glu Asp Gly Cys Ser Cys Arg Phe Pro Glu Glu
            515                 520                 525

Glu Glu Gly Gly Cys Glu Leu Arg Val Lys Phe Ser Arg Ser Ala Asp
    530                 535                 540

Ala Pro Ala Tyr Gln Gln Gly Gln Asn Gln Leu Tyr Asn Glu Leu Asn
545                 550                 555                 560

Leu Gly Arg Arg Glu Glu Tyr Asp Val Leu Asp Lys Arg Arg Gly Arg
                565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
            595                 600                 605

Ile Gly Met Lys Gly Glu Arg Arg Arg Gly Lys Gly His Asp Gly Leu
            610                 615                 620

Tyr Gln Gly Leu Ser Thr Ala Thr Lys Asp Thr Tyr Asp Ala Leu His
625                 630                 635                 640

Met Gln Ala Leu Pro Pro Arg
                645

<210> SEQ ID NO 96
<211> LENGTH: 650
<212> TYPE: PRT
<213> ORGANISM: artificial sequence
<220> FEATURE:
<223> OTHER INFORMATION: D10-v6 polypeptide CAR sequence

<400> SEQUENCE: 96

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Ser Glu Ile Val Leu Ser Gln Ser Pro Ala Ile Thr Ala
    130                 135                 140

Ala Ser Leu Gly Gln Lys Val Thr Ile Thr Cys Ser Ala Ser Ser Asn
145                 150                 155                 160

Val Ser Tyr Ile His Trp Tyr Gln Gln Arg Ser Gly Thr Ser Pro Arg
                165                 170                 175

Pro Trp Ile Tyr Glu Ile Ser Lys Leu Ala Ser Gly Val Pro Val Arg
            180                 185                 190
```

```
Phe Ser Gly Ser Gly Ser Gly Thr Ser Tyr Ser Leu Thr Ile Ser Ser
            195                 200                 205

Met Glu Ala Glu Asp Ala Ala Ile Tyr Tyr Cys Gln Gln Trp Asn Tyr
    210                 215                 220

Pro Leu Ile Thr Phe Gly Ser Gly Thr Lys Leu Glu Ile Gln Glu Pro
225                 230                 235                 240

Lys Ser Pro Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ala Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys Ile Ile Ser Phe Phe Leu Ala Leu Thr Ser Thr
465                 470                 475                 480

Ala Leu Leu Phe Leu Leu Phe Phe Leu Thr Leu Arg Phe Ser Val Val
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
            515                 520                 525

Pro Glu Glu Glu Glu Gly Gly Cys Glu Leu Arg Val Lys Phe Ser Arg
            530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
            595                 600                 605
```

```
Tyr Ser Glu Ile Gly Met Lys Gly Glu Arg Arg Gly Lys Gly His
610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 97
<211> LENGTH: 454
<212> TYPE: PRT
<213> ORGANISM: artificial sequence
<220> FEATURE:
<223> OTHER INFORMATION: Humanized D10-v1 polypeptide CAR sequence
<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT
<222> LOCATION: (114)....(114)
<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:
<221> NAME/KEY: VARIANT
<222> LOCATION: (238)....(238)
<223> OTHER INFORMATION: /replace= " Ile"

<400> SEQUENCE: 97

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Phe
            35                  40                  45

Ser Leu Thr Ser Tyr Gly Tyr Val His Trp Val Arg Gln Pro Pro Gly
        50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
```

Lys Asn Gln Val Ser Leu Lys Leu Ser Ser Val Thr Ala Ala Asp Thr
            85                  90                  95

Ala Val Tyr Tyr Cys Ala Arg Arg Gly Ser Ser Tyr Ser Met Asp Tyr
        100                 105                 110

Trp Gly Gln Gly Thr Leu Val Thr Val Ser Ser Gly Gly Gly Gly Ser
    115                 120                 125

Gly Gly Gly Gly Ser Gly Gly Gly Gly Ser Glu Ile Val Leu Thr Gln
130                 135                 140

Ser Pro Ala Thr Leu Ser Leu Ser Pro Gly Glu Arg Ala Thr Leu Ser
145                 150                 155                 160

Cys Arg Ala Ser Ser Asn Val Ser Tyr Ile His Trp Tyr Gln Gln Lys
            165                 170                 175

Pro Gly Gln Ala Pro Arg Pro Trp Ile Tyr Glu Ile Ser Lys Leu Ala
        180                 185                 190

Thr Gly Ile Pro Ala Arg Phe Ser Gly Ser Gly Ser Gly Thr Asp Tyr
    195                 200                 205

Thr Leu Thr Ile Ser Ser Leu Glu Pro Glu Asp Phe Ala Val Tyr Tyr
210                 215                 220

Cys Gln Gln Trp Asn Tyr Pro Leu Ile Thr Phe Gly Gln Gly Thr Lys
225                 230                 235                 240

Leu Glu Ile Lys Gly Leu Ala Val Ser Thr Ile Ser Ser Phe Phe Pro
            245                 250                 255

Pro Gly Tyr Gln Ile Tyr Ile Trp Ala Pro Leu Ala Gly Thr Cys Gly
        260                 265                 270

Val Leu Leu Leu Ser Leu Val Ile Thr Leu Tyr Cys Lys Arg Gly Arg
    275                 280                 285

Lys Lys Leu Leu Tyr Ile Phe Lys Gln Pro Phe Met Arg Pro Val Gln
290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
            325                 330                 335

Pro Ala Tyr Gln Gln Gly Gln Asn Gln Leu Tyr Asn Glu Leu Asn Leu
        340                 345                 350

Gly Arg Arg Glu Glu Tyr Asp Val Leu Asp Lys Arg Arg Gly Arg Asp
    355                 360                 365

Pro Glu Met Gly Gly Lys Pro Arg Arg Lys Asn Pro Gln Glu Gly Leu
370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
            405                 410                 415

Gln Gly Leu Ser Thr Ala Thr Lys Asp Thr Tyr Asp Ala Leu His Met
        420                 425                 430

Gln Ala Leu Pro Pro Arg
    435

<210> SEQ ID NO 98
<211> LENGTH: 457
<212> TYPE: PRT
<213> ORGANISM: artificial sequence
<220> FEATURE:
<223> OTHER INFORMATION: Humanized D10-v2 polypeptide CAR sequence
<220> FEATURE:

-continued

<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT
<222> LOCATION: (114)....(114)
<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:
<221> NAME/KEY: VARIANT
<222> LOCATION: (238)....(238)
<223> OTHER INFORMATION: /replace= " Ile"

<400> SEQUENCE: 98

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Phe
        35                  40                  45

Ser Leu Thr Ser Tyr Gly Tyr Val His Trp Val Arg Gln Pro Pro Gly
    50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Arg Gly Ser Ser Tyr Ser Met Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175
```

-continued

```
Cys Arg Ala Ser Ser Asn Val Ser Tyr Ile His Trp Tyr Gln Gln Lys
            180                 185                 190
Pro Gly Gln Ala Pro Arg Pro Trp Ile Tyr Glu Ile Ser Lys Leu Ala
        195                 200                 205
Thr Gly Ile Pro Ala Arg Phe Ser Gly Ser Gly Ser Gly Thr Asp Tyr
    210                 215                 220
Thr Leu Thr Ile Ser Ser Leu Glu Pro Glu Asp Phe Ala Val Tyr Tyr
225                 230                 235                 240
Cys Gln Gln Trp Asn Tyr Pro Leu Ile Thr Phe Gly Gln Gly Thr Lys
                245                 250                 255
Leu Glu Ile Lys Gly Leu Ala Val Ser Thr Ile Ser Ser Phe Phe Pro
            260                 265                 270
Pro Gly Tyr Gln Ile Ile Ser Phe Phe Leu Ala Leu Thr Ser Thr Ala
        275                 280                 285
Leu Leu Phe Leu Leu Phe Phe Leu Thr Leu Arg Phe Ser Val Val Lys
    290                 295                 300
Arg Gly Arg Lys Lys Leu Leu Tyr Ile Phe Lys Gln Pro Phe Met Arg
305                 310                 315                 320
Pro Val Gln Thr Thr Gln Glu Glu Asp Gly Cys Ser Cys Arg Phe Pro
                325                 330                 335
Glu Glu Glu Glu Gly Gly Cys Glu Leu Arg Val Lys Phe Ser Arg Ser
            340                 345                 350
Ala Asp Ala Pro Ala Tyr Gln Gln Gly Gln Asn Gln Leu Tyr Asn Glu
        355                 360                 365
Leu Asn Leu Gly Arg Arg Glu Glu Tyr Asp Val Leu Asp Lys Arg Arg
    370                 375                 380
Gly Arg Asp Pro Glu Met Gly Gly Lys Pro Arg Arg Lys Asn Pro Gln
385                 390                 395                 400
Glu Gly Leu Tyr Asn Glu Leu Gln Lys Asp Lys Met Ala Glu Ala Tyr
                405                 410                 415
Ser Glu Ile Gly Met Lys Gly Glu Arg Arg Arg Gly Lys Gly His Asp
            420                 425                 430
Gly Leu Tyr Gln Gly Leu Ser Thr Ala Thr Lys Asp Thr Tyr Asp Ala
        435                 440                 445
Leu His Met Gln Ala Leu Pro Pro Arg
    450                 455
```

<210> SEQ ID NO 99
<211> LENGTH: 483
<212> TYPE: PRT
<213> ORGANISM: artificial sequence
<220> FEATURE:
<223> OTHER INFORMATION: Humanized D10-v3 polypeptide CAR sequence
<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT

```
<222> LOCATION: (114)....(114)
<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:
<221> NAME/KEY: VARIANT
<222> LOCATION: (238)....(238)
<223> OTHER INFORMATION: /replace= " Ile"

<400> SEQUENCE: 99

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Phe
        35                  40                  45

Ser Leu Thr Ser Tyr Gly Tyr Val His Trp Val Arg Gln Pro Pro Gly
    50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Arg Gly Ser Ser Tyr Ser Met Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Ser Asn Val Ser Tyr Ile His Trp Tyr Gln Gln Lys
            180                 185                 190

Pro Gly Gln Ala Pro Arg Pro Trp Ile Tyr Glu Ile Ser Lys Leu Ala
        195                 200                 205

Thr Gly Ile Pro Ala Arg Phe Ser Gly Ser Gly Ser Gly Thr Asp Tyr
    210                 215                 220

Thr Leu Thr Ile Ser Ser Leu Glu Pro Glu Asp Phe Ala Val Tyr Tyr
225                 230                 235                 240

Cys Gln Gln Trp Asn Tyr Pro Leu Ile Thr Phe Gly Gln Gly Thr Lys
                245                 250                 255

Leu Glu Ile Lys Thr Thr Thr Pro Ala Pro Arg Pro Pro Thr Pro Ala
            260                 265                 270
```

```
Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
            325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
            355                 360                 365

Cys Glu Leu Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 100
<211> LENGTH: 486
<212> TYPE: PRT
<213> ORGANISM: artificial sequence
<220> FEATURE:
<223> OTHER INFORMATION: Humanized D10-v4 polypeptide CAR sequence
<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT
<222> LOCATION: (114)....(114)
<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
```

```
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:
<221> NAME/KEY: VARIANT
<222> LOCATION: (238)....(238)
<223> OTHER INFORMATION: /replace= " Ile"

<400> SEQUENCE: 100

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Phe
        35                  40                  45

Ser Leu Thr Ser Tyr Gly Tyr Val His Trp Val Arg Gln Pro Pro Gly
50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Arg Gly Ser Ser Tyr Ser Met Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Ser Asn Val Ser Tyr Ile His Trp Tyr Gln Gln Lys
            180                 185                 190

Pro Gly Gln Ala Pro Arg Pro Trp Ile Tyr Glu Ile Ser Lys Leu Ala
        195                 200                 205

Thr Gly Ile Pro Ala Arg Phe Ser Gly Ser Gly Ser Gly Thr Asp Tyr
210                 215                 220

Thr Leu Thr Ile Ser Ser Leu Glu Pro Glu Asp Phe Ala Val Tyr Tyr
225                 230                 235                 240

Cys Gln Gln Trp Asn Tyr Pro Leu Ile Thr Phe Gly Gln Gly Thr Lys
                245                 250                 255

Leu Glu Ile Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
290                 295                 300

Asp Ile Ile Ser Phe Phe Leu Ala Leu Thr Ser Thr Ala Leu Leu Phe
305                 310                 315                 320

Leu Leu Phe Phe Leu Thr Leu Arg Phe Ser Val Val Lys Arg Gly Arg
                325                 330                 335
```

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 101
<211> LENGTH: 669
<212> TYPE: PRT
<213> ORGANISM: artificial sequence
<220> FEATURE:
<223> OTHER INFORMATION: Humanized D10-v5 polypeptide CAR sequence
<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT
<222> LOCATION: (114)....(114)
<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:

```
<221> NAME/KEY: VARIANT
<222> LOCATION: (238)....(238)
<223> OTHER INFORMATION: /replace= " Ile"

<400> SEQUENCE: 101

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Phe
        35                  40                  45

Ser Leu Thr Ser Tyr Gly Tyr Val His Trp Val Arg Gln Pro Pro Gly
50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Arg Gly Ser Ser Tyr Ser Met Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Ser Asn Val Ser Tyr Ile His Trp Tyr Gln Gln Lys
            180                 185                 190

Pro Gly Gln Ala Pro Arg Pro Trp Ile Tyr Glu Ile Ser Lys Leu Ala
        195                 200                 205

Thr Gly Ile Pro Ala Arg Phe Ser Gly Ser Gly Ser Gly Thr Asp Tyr
210                 215                 220

Thr Leu Thr Ile Ser Ser Leu Glu Pro Glu Asp Phe Ala Val Tyr Tyr
225                 230                 235                 240

Cys Gln Gln Trp Asn Tyr Pro Leu Ile Thr Phe Gly Gln Gly Thr Lys
                245                 250                 255

Leu Glu Ile Lys Glu Pro Lys Ser Pro Asp Lys Thr His Thr Cys Pro
            260                 265                 270

Pro Cys Pro Ala Pro Pro Val Ala Gly Pro Ser Val Phe Leu Phe Pro
        275                 280                 285

Pro Lys Pro Lys Asp Thr Leu Met Ile Ala Arg Thr Pro Glu Val Thr
290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
370                 375                 380

Gly Gln Pro Arg Glu Pro Gln Val Tyr Thr Leu Pro Pro Ser Arg Asp
```

```
                385               390                395                 400
    Glu Leu Thr Lys Asn Gln Val Ser Leu Thr Cys Leu Val Lys Gly Phe
                    405                 410                415

Tyr Pro Ser Asp Ile Ala Val Glu Trp Glu Ser Asn Gly Gln Pro Glu
                    420                 425                430

Asn Asn Tyr Lys Thr Thr Pro Pro Val Leu Asp Ser Asp Gly Ser Phe
                    435                 440                445

Phe Leu Tyr Ser Lys Leu Thr Val Asp Lys Ser Arg Trp Gln Gln Gly
        450                 455                 460

Asn Val Phe Ser Cys Ser Val Met His Glu Ala Leu His Asn His Tyr
    465                 470                 475                 480

Thr Gln Lys Ser Leu Ser Leu Ser Pro Gly Lys Ile Tyr Ile Trp Ala
                    485                 490                495

Pro Leu Ala Gly Thr Cys Gly Val Leu Leu Leu Ser Leu Val Ile Thr
                    500                 505                510

Leu Tyr Cys Lys Arg Gly Arg Lys Lys Leu Leu Tyr Ile Phe Lys Gln
                    515                 520                525

Pro Phe Met Arg Pro Val Gln Thr Thr Gln Glu Glu Asp Gly Cys Ser
        530                 535                 540

Cys Arg Phe Pro Glu Glu Glu Glu Gly Gly Cys Glu Leu Arg Val Lys
    545                 550                 555                 560

Phe Ser Arg Ser Ala Asp Ala Pro Ala Tyr Gln Gln Gly Gln Asn Gln
                    565                 570                575

Leu Tyr Asn Glu Leu Asn Leu Gly Arg Arg Glu Glu Tyr Asp Val Leu
                    580                 585                590

Asp Lys Arg Arg Gly Arg Asp Pro Glu Met Gly Gly Lys Pro Arg Arg
                    595                 600                605

Lys Asn Pro Gln Glu Gly Leu Tyr Asn Glu Leu Gln Lys Asp Lys Met
            610                 615                620

Ala Glu Ala Tyr Ser Glu Ile Gly Met Lys Gly Glu Arg Arg Arg Gly
    625                 630                 635                 640

Lys Gly His Asp Gly Leu Tyr Gln Gly Leu Ser Thr Ala Thr Lys Asp
                    645                 650                655

Thr Tyr Asp Ala Leu His Met Gln Ala Leu Pro Pro Arg
                660                 665

<210> SEQ ID NO 102
<211> LENGTH: 672
<212> TYPE: PRT
<213> ORGANISM: artificial sequence
<220> FEATURE:
<223> OTHER INFORMATION: Humanized D10-v6 polypeptide CAR sequence
<220> FEATURE:
<221> NAME/KEY: VARIANT
<222> LOCATION: (26)....(26)
<223> OTHER INFORMATION: /replace= " Lys"
<220> FEATURE:
<221> NAME/KEY: VARIANT
<222> LOCATION: (34)....(34)
<223> OTHER INFORMATION: /replace= " Ala "
<220> FEATURE:
<221> NAME/KEY: VARIANT
<222> LOCATION: (83)....(83)
<223> OTHER INFORMATION: /replace= " Ser"
<220> FEATURE:
<221> NAME/KEY: VARIANT
<222> LOCATION: (110)....(110)
<223> OTHER INFORMATION: /replace= " Asp"
<220> FEATURE:
<221> NAME/KEY: VARIANT
<222> LOCATION: (114)....(114)
```

<223> OTHER INFORMATION: /replace= " Met"
<220> FEATURE:
<221> NAME/KEY: VARIANT
<222> LOCATION: (159)....(159)
<223> OTHER INFORMATION: /replace= " Ser"
<220> FEATURE:
<221> NAME/KEY: VARIANT
<222> LOCATION: (178)....(178)
<223> OTHER INFORMATION: /replace= " Ser"
<220> FEATURE:
<221> NAME/KEY: VARIANT
<222> LOCATION: (193)....(193)
<223> OTHER INFORMATION: /replace= " Ser"
<220> FEATURE:
<221> NAME/KEY: VARIANT
<222> LOCATION: (209)....(209)
<223> OTHER INFORMATION: /replace= " Ser"
<220> FEATURE:
<221> NAME/KEY: VARIANT
<222> LOCATION: (233)....(233)
<223> OTHER INFORMATION: /replace= " Ala"
<220> FEATURE:
<221> NAME/KEY: VARIANT
<222> LOCATION: (238)....(238)
<223> OTHER INFORMATION: /replace= " Ile"

<400> SEQUENCE: 102

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Phe
        35                  40                  45

Ser Leu Thr Ser Tyr Gly Tyr Val His Trp Val Arg Gln Pro Pro Gly
50                  55                  60

Lys Gly Leu Glu Trp Leu Gly Val Ile Trp Ala Gly Gly Phe Thr Asn
65                  70                  75                  80

Tyr Asn Pro Ser Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Arg Gly Ser Ser Tyr Ser Met Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Ser Asn Val Ser Tyr Ile His Trp Tyr Gln Gln Lys
            180                 185                 190

Pro Gly Gln Ala Pro Arg Pro Trp Ile Tyr Glu Ile Ser Lys Leu Ala
        195                 200                 205

Thr Gly Ile Pro Ala Arg Phe Ser Gly Ser Gly Ser Gly Thr Asp Tyr
210                 215                 220

Thr Leu Thr Ile Ser Ser Leu Glu Pro Glu Asp Phe Ala Val Tyr Tyr
225                 230                 235                 240

Cys Gln Gln Trp Asn Tyr Pro Leu Ile Thr Phe Gly Gln Gly Thr Lys
                245                 250                 255

Leu Glu Ile Lys Glu Pro Lys Ser Pro Asp Lys Thr His Thr Cys Pro
            260                 265                 270
```

```
Pro Cys Pro Ala Pro Val Ala Gly Pro Ser Val Phe Leu Phe Pro
            275                 280                 285

Pro Lys Pro Lys Asp Thr Leu Met Ile Ala Arg Thr Pro Glu Val Thr
290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
            405                 410                 415

Tyr Pro Ser Asp Ile Ala Val Glu Trp Glu Ser Asn Gly Gln Pro Glu
        420                 425                 430

Asn Asn Tyr Lys Thr Thr Pro Pro Val Leu Asp Ser Asp Gly Ser Phe
435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys Ile Ile Ser Phe Phe
            485                 490                 495

Leu Ala Leu Thr Ser Thr Ala Leu Leu Phe Leu Leu Phe Phe Leu Thr
        500                 505                 510

Leu Arg Phe Ser Val Val Lys Arg Gly Arg Lys Lys Leu Leu Tyr Ile
    515                 520                 525

Phe Lys Gln Pro Phe Met Arg Pro Val Gln Thr Thr Gln Glu Glu Asp
530                 535                 540

Gly Cys Ser Cys Arg Phe Pro Glu Glu Glu Glu Gly Gly Cys Glu Leu
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670

<210> SEQ ID NO 103
<211> LENGTH: 435
<212> TYPE: PRT
```

<213> ORGANISM: artificial sequence
<220> FEATURE:
<223> OTHER INFORMATION: G6-v1 polypeptide CAR sequence

<400> SEQUENCE: 103

```
Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Val Gly Glu Arg Val Thr Ile Thr Cys Lys Ala Ser
145                 150                 155                 160

Gln Gly Ile Asn Ser Tyr Ser Gly Trp Phe Gln Gln Lys Pro Gly Lys
                165                 170                 175

Ser Pro Lys Thr Leu Ile Tyr Arg Gly Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Ile
225                 230                 235                 240

Lys Gly Leu Ala Val Ser Thr Ile Ser Ser Phe Phe Pro Pro Gly Tyr
                245                 250                 255

Gln Ile Tyr Ile Trp Ala Pro Leu Ala Gly Thr Cys Gly Val Leu Leu
            260                 265                 270

Leu Ser Leu Val Ile Thr Leu Tyr Cys Lys Arg Gly Arg Lys Lys Leu
        275                 280                 285

Leu Tyr Ile Phe Lys Gln Pro Phe Met Arg Pro Val Gln Thr Thr Gln
    290                 295                 300

Glu Glu Asp Gly Cys Ser Cys Arg Phe Pro Glu Glu Glu Glu Gly Gly
305                 310                 315                 320

Cys Glu Leu Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
        355                 360                 365

Gly Gly Lys Pro Arg Arg Lys Asn Pro Gln Glu Gly Leu Tyr Asn Glu
    370                 375                 380

Leu Gln Lys Asp Lys Met Ala Glu Ala Tyr Ser Glu Ile Gly Met Lys
```

```
                385                 390                 395                 400
Gly Glu Arg Arg Gly Lys Gly His Asp Gly Leu Tyr Gln Gly Leu
                        405                 410                 415

Ser Thr Ala Thr Lys Asp Thr Tyr Asp Ala Leu His Met Gln Ala Leu
                420                 425                 430

Pro Pro Arg
        435

<210> SEQ ID NO 104
<211> LENGTH: 438
<212> TYPE: PRT
<213> ORGANISM: artificial sequence
<220> FEATURE:
<223> OTHER INFORMATION: G6-v2 polypeptide CAR sequence

<400> SEQUENCE: 104

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Lys Met Thr Gln Ser Pro Ser Ser
    130                 135                 140

Met Tyr Ala Ser Val Gly Glu Arg Val Thr Ile Thr Cys Lys Ala Ser
145                 150                 155                 160

Gln Gly Ile Asn Ser Tyr Ser Gly Trp Phe Gln Gln Lys Pro Gly Lys
                165                 170                 175

Ser Pro Lys Thr Leu Ile Tyr Arg Gly Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Ile
225                 230                 235                 240

Lys Gly Leu Ala Val Ser Thr Ile Ser Ser Phe Phe Pro Pro Gly Tyr
                245                 250                 255

Gln Ile Ile Ser Phe Phe Leu Ala Leu Thr Ser Thr Ala Leu Leu Phe
            260                 265                 270

Leu Leu Phe Phe Leu Thr Leu Arg Phe Ser Val Val Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
```

```
                    305                 310                 315                 320
Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
                340                 345                 350

Gly Arg Arg Glu Glu Tyr Asp Val Leu Asp Lys Arg Arg Gly Arg Asp
                355                 360                 365

Pro Glu Met Gly Gly Lys Pro Arg Arg Lys Asn Pro Gln Glu Gly Leu
                370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
                420                 425                 430

Gln Ala Leu Pro Pro Arg
                435

<210> SEQ ID NO 105
<211> LENGTH: 464
<212> TYPE: PRT
<213> ORGANISM: artificial sequence
<220> FEATURE:
<223> OTHER INFORMATION: G6-v3 polypeptide CAR sequence

<400> SEQUENCE: 105

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
                20                  25                  30

Asn Met Asn Trp Val Lys Gln Thr Asn Gly Lys Ser Leu Glu Trp Ile
            35                  40                  45

Gly Ser Ile Asp Pro Tyr Tyr Gly Gly Ser Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Ser Ala Val Tyr Tyr Cys
                85                  90                  95

Ala Arg Ser Pro Gly Gly Asp Tyr Ala Met Asp Tyr Trp Gly Gln Gly
                100                 105                 110

Thr Ser Val Thr Val Ser Ser Gly Gly Gly Ser Gly Gly Gly
                115                 120                 125

Ser Gly Gly Gly Ser Asp Ile Lys Met Thr Gln Ser Pro Ser Ser
                130                 135                 140

Met Tyr Ala Ser Val Gly Glu Arg Val Thr Ile Thr Cys Lys Ala Ser
145                 150                 155                 160

Gln Gly Ile Asn Ser Tyr Ser Gly Trp Phe Gln Gln Lys Pro Gly Lys
                165                 170                 175

Ser Pro Lys Thr Leu Ile Tyr Arg Gly Asn Arg Leu Val Asp Gly Val
                180                 185                 190

Pro Ser Arg Phe Ser Gly Ser Gly Ser Gly Gln Asp Tyr Ser Leu Thr
                195                 200                 205

Ile Ser Ser Leu Glu Tyr Glu Asp Met Gly Ile Tyr Tyr Cys Leu Gln
                210                 215                 220

Tyr Asp Glu Phe Pro Tyr Thr Phe Gly Gly Gly Thr Lys Leu Glu Ile
```

```
              225                 230                 235                 240
Lys Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
                260                 265                 270

Gly Gly Ala Val His Thr Arg Gly Leu Asp Phe Ala Cys Asp Ile Tyr
                275                 280                 285

Ile Trp Ala Pro Leu Ala Gly Thr Cys Gly Val Leu Leu Leu Ser Leu
            290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
                340                 345                 350

Arg Val Lys Phe Ser Arg Ser Ala Asp Ala Pro Ala Tyr Gln Gln Gly
                355                 360                 365

Gln Asn Gln Leu Tyr Asn Glu Leu Asn Leu Gly Arg Arg Glu Glu Tyr
            370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
                420                 425                 430

Arg Arg Gly Lys Gly His Asp Gly Leu Tyr Gln Gly Leu Ser Thr Ala
                435                 440                 445

Thr Lys Asp Thr Tyr Asp Ala Leu His Met Gln Ala Leu Pro Pro Arg
            450                 455                 460

<210> SEQ ID NO 106
<211> LENGTH: 467
<212> TYPE: PRT
<213> ORGANISM: artificial sequence
<220> FEATURE:
<223> OTHER INFORMATION: G6-v4 polypeptide CAR sequence

<400> SEQUENCE: 106

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
                20                  25                  30

Asn Met Asn Trp Val Lys Gln Thr Asn Gly Lys Ser Leu Glu Trp Ile
            35                  40                  45

Gly Ser Ile Asp Pro Tyr Tyr Gly Gly Ser Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Ser Ala Val Tyr Tyr Cys
                85                  90                  95

Ala Arg Ser Pro Gly Gly Asp Tyr Ala Met Asp Tyr Trp Gly Gln Gly
                100                 105                 110

Thr Ser Val Thr Val Ser Ser Gly Gly Gly Ser Gly Gly Gly Gly
                115                 120                 125

Ser Gly Gly Gly Gly Ser Asp Ile Lys Met Thr Gln Ser Pro Ser Ser
```

```
            130                 135                 140
Met Tyr Ala Ser Val Gly Glu Arg Val Thr Ile Thr Cys Lys Ala Ser
145                 150                 155                 160

Gln Gly Ile Asn Ser Tyr Ser Gly Trp Phe Gln Gln Lys Pro Gly Lys
                165                 170                 175

Ser Pro Lys Thr Leu Ile Tyr Arg Gly Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Ile
225                 230                 235                 240

Lys Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
                260                 265                 270

Gly Gly Ala Val His Thr Arg Gly Leu Asp Phe Ala Cys Asp Ile Ile
            275                 280                 285

Ser Phe Phe Leu Ala Leu Thr Ser Thr Ala Leu Leu Phe Leu Leu Phe
    290                 295                 300

Phe Leu Thr Leu Arg Phe Ser Val Val Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
                340                 345                 350

Cys Glu Leu Arg Val Lys Phe Ser Arg Ser Ala Asp Ala Pro Ala Tyr
            355                 360                 365

Gln Gln Gly Gln Asn Gln Leu Tyr Asn Glu Leu Asn Leu Gly Arg Arg
        370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
                420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
        450                 455                 460

Pro Pro Arg
465

<210> SEQ ID NO 107
<211> LENGTH: 650
<212> TYPE: PRT
<213> ORGANISM: artificial sequence
<220> FEATURE:
<223> OTHER INFORMATION: G6-v5 polypeptide CAR sequence

<400> SEQUENCE: 107

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
```

```
                20                  25                  30
Asn Met Asn Trp Val Lys Gln Thr Asn Gly Lys Ser Leu Glu Trp Ile
        35                  40                  45
Gly Ser Ile Asp Pro Tyr Tyr Gly Gly Ser Thr Tyr Asn Gln Lys Phe
    50                  55                  60
Lys Asp Lys Ala Thr Leu Thr Val Asp Lys Ser Ser Thr Ala Tyr
65                  70                  75                  80
Met Gln Leu Lys Ser Leu Thr Ser Asp Asp Ser Ala Val Tyr Tyr Cys
                85                  90                  95
Ala Arg Ser Pro Gly Gly Asp Tyr Ala Met Asp Tyr Trp Gly Gln Gly
            100                 105                 110
Thr Ser Val Thr Val Ser Ser Gly Gly Gly Ser Gly Gly Gly Gly
            115                 120                 125
Ser Gly Gly Gly Gly Ser Asp Ile Lys Met Thr Gln Ser Pro Ser Ser
    130                 135                 140
Met Tyr Ala Ser Val Gly Glu Arg Val Thr Ile Thr Cys Lys Ala Ser
145                 150                 155                 160
Gln Gly Ile Asn Ser Tyr Ser Gly Trp Phe Gln Gln Lys Pro Gly Lys
                165                 170                 175
Ser Pro Lys Thr Leu Ile Tyr Arg Gly Asn Arg Leu Val Asp Gly Val
            180                 185                 190
Pro Ser Arg Phe Ser Gly Ser Gly Ser Gly Gln Asp Tyr Ser Leu Thr
            195                 200                 205
Ile Ser Ser Leu Glu Tyr Glu Asp Met Gly Ile Tyr Tyr Cys Leu Gln
    210                 215                 220
Tyr Asp Glu Phe Pro Tyr Thr Phe Gly Gly Gly Thr Lys Leu Glu Ile
225                 230                 235                 240
Lys Glu Pro Lys Ser Pro Asp Lys Thr His Thr Cys Pro Pro Cys Pro
                245                 250                 255
Ala Pro Pro Val Ala Gly Pro Ser Val Phe Leu Phe Pro Pro Lys Pro
            260                 265                 270
Lys Asp Thr Leu Met Ile Ala Arg Thr Pro Glu Val Thr Cys Val Val
            275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Asp Glu Leu Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
```

```
Ser Cys Ser Val Met His Glu Ala Leu His Asn His Tyr Thr Gln Lys
    450                 455                 460

Ser Leu Ser Leu Ser Pro Gly Lys Ile Tyr Ile Trp Ala Pro Leu Ala
465                 470                 475                 480

Gly Thr Cys Gly Val Leu Leu Leu Ser Leu Val Ile Thr Leu Tyr Cys
                    485                 490                 495

Lys Arg Gly Arg Lys Lys Leu Leu Tyr Ile Phe Lys Gln Pro Phe Met
                500                 505                 510

Arg Pro Val Gln Thr Thr Gln Glu Glu Asp Gly Cys Ser Cys Arg Phe
            515                 520                 525

Pro Glu Glu Glu Glu Gly Gly Cys Glu Leu Arg Val Lys Phe Ser Arg
        530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
                580                 585                 590

Gln Glu Gly Leu Tyr Asn Glu Leu Gln Lys Asp Lys Met Ala Glu Ala
            595                 600                 605

Tyr Ser Glu Ile Gly Met Lys Gly Glu Arg Arg Arg Gly Lys Gly His
        610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 108
<211> LENGTH: 653
<212> TYPE: PRT
<213> ORGANISM: artificial sequence
<220> FEATURE:
<223> OTHER INFORMATION: G6-v6 polypeptide CAR sequence

<400> SEQUENCE: 108

Glu Val Gln Leu Gln Gln Ser Gly Pro Glu Leu Lys Pro Gly Ala
1               5                   10                  15

Ser Val Lys Ile Ser Cys Lys Ala Ser Gly Phe Ala Phe Thr Gly Tyr
                20                  25                  30

Asn Met Asn Trp Val Lys Gln Thr Asn Gly Lys Ser Leu Glu Trp Ile
            35                  40                  45

Gly Ser Ile Asp Pro Tyr Tyr Gly Gly Ser Thr Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
                100                 105                 110

Thr Ser Val Thr Val Ser Ser Gly Gly Gly Gly Ser Gly Gly Gly Gly
            115                 120                 125

Ser Gly Gly Gly Gly Ser Asp Ile Lys Met Thr Gln Ser Pro Ser Ser
        130                 135                 140

Met Tyr Ala Ser Val Gly Glu Arg Val Thr Ile Thr Cys Lys Ala Ser
145                 150                 155                 160
```

```
Gln Gly Ile Asn Ser Tyr Ser Gly Trp Phe Gln Gln Lys Pro Gly Lys
                165                 170                 175

Ser Pro Lys Thr Leu Ile Tyr Arg Gly Asn Arg Leu Val Asp Gly Val
            180                 185                 190

Pro Ser Arg Phe Ser Gly Ser Gly Ser Gly Gln Asp Tyr Ser Leu Thr
        195                 200                 205

Ile Ser Ser Leu Glu Tyr Glu Asp Met Gly Ile Tyr Tyr Cys Leu Gln
    210                 215                 220

Tyr Asp Glu Phe Pro Tyr Thr Phe Gly Gly Gly Thr Lys Leu Glu Ile
225                 230                 235                 240

Lys Glu Pro Lys Ser Pro Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ala Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys Ile Ile Ser Phe Phe Leu Ala Leu
465                 470                 475                 480

Thr Ser Thr Ala Leu Leu Phe Leu Leu Phe Phe Leu Thr Leu Arg Phe
                485                 490                 495

Ser Val Val Lys Arg Gly Arg Lys Lys Leu Leu Tyr Ile Phe Lys Gln
            500                 505                 510

Pro Phe Met Arg Pro Val Gln Thr Thr Gln Glu Glu Asp Gly Cys Ser
        515                 520                 525

Cys Arg Phe Pro Glu Glu Glu Gly Gly Cys Glu Leu Arg Val Lys
    530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575
```

Asp Lys Arg Arg Gly Arg Asp Pro Glu Met Gly Gly Lys Pro Arg Arg
                580                 585                 590

Lys Asn Pro Gln Glu Gly Leu Tyr Asn Glu Leu Gln Lys Asp Lys Met
            595                 600                 605

Ala Glu Ala Tyr Ser Glu Ile Gly Met Lys Gly Glu Arg Arg Arg Gly
610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 109
<211> LENGTH: 435
<212> TYPE: PRT
<213> ORGANISM: artificial sequence
<220> FEATURE:
<223> OTHER INFORMATION: G3-v1 polypeptide CAR sequence

<400> SEQUENCE: 109

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

Lys Ser Lys Ala Thr Leu Thr Ala Asp Thr Ser Ser Thr Ala Tyr
65                  70                  75                  80

Met Gln Leu Ser Ser Leu Ala Ser Glu Asp Ser Ala Leu Tyr Tyr Cys
                85                  90                  95

Ala Arg Asp Gly Asn Tyr Tyr Ala Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Gln Met Thr Gln Thr Thr Ser Ser Leu
    130                 135                 140

Ser Ala Ser Leu Gly Asp Arg Val Thr Ile Thr Cys Arg Ala Ser Gln
145                 150                 155                 160

Asp Ile Asn Asn Tyr Leu Asn Trp Tyr Gln Gln Lys Pro Asp Gly Thr
                165                 170                 175

Val Lys Leu Leu Ile Tyr Tyr Thr Ser Ala Leu His Ser Gly Val Pro
            180                 185                 190

Ser Arg Phe Ser Gly Ser Gly Ser Gly Thr Asp Tyr Ser Leu Thr Ile
        195                 200                 205

Ser Asn Leu Glu Gln Glu Asp Ile Ala Thr Tyr Phe Cys Gln Gln Gly
    210                 215                 220

Asn Thr Leu Pro Pro Tyr Thr Phe Gly Gly Gly Thr Lys Leu Glu Ile
225                 230                 235                 240

Lys Gly Leu Ala Val Ser Thr Ile Ser Ser Phe Phe Pro Pro Gly Tyr
                245                 250                 255

Gln Ile Tyr Ile Trp Ala Pro Leu Ala Gly Thr Cys Gly Val Leu Leu
            260                 265                 270

Leu Ser Leu Val Ile Thr Leu Tyr Cys Lys Arg Gly Arg Lys Lys Leu
        275                 280                 285

Leu Tyr Ile Phe Lys Gln Pro Phe Met Arg Pro Val Gln Thr Thr Gln
            290                 295                 300

Glu Glu Asp Gly Cys Ser Cys Arg Phe Pro Glu Glu Glu Gly Gly
305                 310                 315                 320

Cys Glu Leu Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
            355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
            420                 425                 430

Pro Pro Arg
        435

<210> SEQ ID NO 110
<211> LENGTH: 438
<212> TYPE: PRT
<213> ORGANISM: artificial sequence
<220> FEATURE:
<223> OTHER INFORMATION: G3-v2 polypeptide CAR sequence

<400> SEQUENCE: 110

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

Lys Ser Lys Ala Thr Leu Thr Ala Asp Thr Ser Ser Ser Thr Ala Tyr
65                  70                  75                  80

Met Gln Leu Ser Ser Leu Ala Ser Glu Asp Ser Ala Leu Tyr Tyr Cys
                85                  90                  95

Ala Arg Asp Gly Asn Tyr Tyr Ala Met Asp Tyr Trp Gly Gln Gly Thr
            100                 105                 110

Ser Val Thr Val Ser Ser Gly Gly Gly Ser Gly Gly Gly Gly Ser
        115                 120                 125

Gly Gly Gly Gly Ser Asp Ile Gln Met Thr Gln Thr Thr Ser Ser Leu
    130                 135                 140

Ser Ala Ser Leu Gly Asp Arg Val Thr Ile Thr Cys Arg Ala Ser Gln
145                 150                 155                 160

Asp Ile Asn Asn Tyr Leu Asn Trp Tyr Gln Gln Lys Pro Asp Gly Thr
                165                 170                 175

Val Lys Leu Leu Ile Tyr Tyr Thr Ser Ala Leu His Ser Gly Val Pro
            180                 185                 190

Ser Arg Phe Ser Gly Ser Gly Ser Gly Thr Asp Tyr Ser Leu Thr Ile
        195                 200                 205

Ser Asn Leu Glu Gln Glu Asp Ile Ala Thr Tyr Phe Cys Gln Gln Gly
    210                 215                 220

Asn Thr Leu Pro Pro Tyr Thr Phe Gly Gly Gly Thr Lys Leu Glu Ile
225                 230                 235                 240

Lys Gly Leu Ala Val Ser Thr Ile Ser Ser Phe Phe Pro Pro Gly Tyr
                245                 250                 255

Gln Ile Ile Ser Phe Phe Leu Ala Leu Thr Ser Thr Ala Leu Leu Phe
            260                 265                 270

Leu Leu Phe Phe Leu Thr Leu Arg Phe Ser Val Val Lys Arg Gly Arg
        275                 280                 285

Lys Lys Leu Leu Tyr Ile Phe Lys Gln Pro Phe Met Arg Pro Val Gln
290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
        355                 360                 365

Pro Glu Met Gly Gly Lys Pro Arg Arg Lys Asn Pro Gln Glu Gly Leu
370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
        435

<210> SEQ ID NO 111
<211> LENGTH: 464
<212> TYPE: PRT
<213> ORGANISM: artificial sequence
<220> FEATURE:
<223> OTHER INFORMATION: G3-v3 polypeptide CAR sequence

<400> SEQUENCE: 111

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

Lys Ser Lys Ala Thr Leu Thr Ala Asp Thr Ser Ser Thr Ala Tyr
65                  70                  75                  80

Met Gln Leu Ser Ser Leu Ala Ser Glu Asp Ser Ala Leu Tyr Tyr Cys
            85                  90                  95

Ala Arg Asp Gly Asn Tyr Tyr Ala Met Asp Tyr Trp Gly Gln Gly Thr
            100                 105                 110

Ser Val Thr Val Ser Ser Gly Gly Gly Ser Gly Gly Gly Ser
            115                 120                 125

Gly Gly Gly Gly Ser Asp Ile Gln Met Thr Gln Thr Ser Ser Leu
            130                 135                 140

Ser Ala Ser Leu Gly Asp Arg Val Thr Ile Thr Cys Arg Ala Ser Gln
145                 150                 155                 160

Asp Ile Asn Asn Tyr Leu Asn Trp Tyr Gln Gln Lys Pro Asp Gly Thr
                165                 170                 175

Val Lys Leu Leu Ile Tyr Tyr Thr Ser Ala Leu His Ser Gly Val Pro
            180                 185                 190

Ser Arg Phe Ser Gly Ser Gly Ser Gly Thr Asp Tyr Ser Leu Thr Ile
        195                 200                 205

Ser Asn Leu Glu Gln Glu Asp Ile Ala Thr Tyr Phe Cys Gln Gln Gly
210                 215                 220

Asn Thr Leu Pro Pro Tyr Thr Phe Gly Gly Gly Thr Lys Leu Glu Ile
225                 230                 235                 240

Lys Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
450                 455                 460

<210> SEQ ID NO 112
<211> LENGTH: 467
<212> TYPE: PRT
<213> ORGANISM: artificial sequence
<220> FEATURE:
<223> OTHER INFORMATION: G3-v4 polypeptide CAR sequence

<400> SEQUENCE: 112

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

```
Trp Ile Asn Trp Val Lys Leu Arg Pro Gly Gln Gly Leu Glu Trp Ile
             35                  40                  45
Gly Glu Ile Tyr Pro Gly Ser Gly Ser Thr Asn Tyr Asn Glu Lys Phe
 50                  55                  60
Lys Ser Lys Ala Thr Leu Thr Ala Asp Thr Ser Ser Ser Thr Ala Tyr
 65                  70                  75                  80
Met Gln Leu Ser Ser Leu Ala Ser Glu Asp Ser Ala Leu Tyr Tyr Cys
             85                  90                  95
Ala Arg Asp Gly Asn Tyr Tyr Ala Met Asp Tyr Trp Gly Gln Gly Thr
            100                 105                 110
Ser Val Thr Val Ser Ser Gly Gly Gly Ser Gly Gly Gly Gly Ser
            115                 120                 125
Gly Gly Gly Gly Ser Asp Ile Gln Met Thr Gln Thr Thr Ser Ser Leu
            130                 135                 140
Ser Ala Ser Leu Gly Asp Arg Val Thr Ile Thr Cys Arg Ala Ser Gln
145                 150                 155                 160
Asp Ile Asn Asn Tyr Leu Asn Trp Tyr Gln Gln Lys Pro Asp Gly Thr
                165                 170                 175
Val Lys Leu Leu Ile Tyr Tyr Thr Ser Ala Leu His Ser Gly Val Pro
            180                 185                 190
Ser Arg Phe Ser Gly Ser Gly Ser Gly Thr Asp Tyr Ser Leu Thr Ile
            195                 200                 205
Ser Asn Leu Glu Gln Glu Asp Ile Ala Thr Tyr Phe Cys Gln Gln Gly
            210                 215                 220
Asn Thr Leu Pro Pro Tyr Thr Phe Gly Gly Gly Thr Lys Leu Glu Ile
225                 230                 235                 240
Lys Thr Thr Thr Pro Ala Pro Arg Pro Pro Thr Pro Ala Pro Thr Ile
                245                 250                 255
Ala Ser Gln Pro Leu Ser Leu Arg Pro Glu Ala Cys Arg Pro Ala Ala
            260                 265                 270
Gly Gly Ala Val His Thr Arg Gly Leu Asp Phe Ala Cys Asp Ile Ile
            275                 280                 285
Ser Phe Phe Leu Ala Leu Thr Ser Thr Ala Leu Leu Phe Leu Leu Phe
            290                 295                 300
Phe Leu Thr Leu Arg Phe Ser Val Val Lys Arg Gly Arg Lys Lys Leu
305                 310                 315                 320
Leu Tyr Ile Phe Lys Gln Pro Phe Met Arg Pro Val Gln Thr Thr Gln
                325                 330                 335
Glu Glu Asp Gly Cys Ser Cys Arg Phe Pro Glu Glu Glu Glu Gly Gly
            340                 345                 350
Cys Glu Leu Arg Val Lys Phe Ser Arg Ser Ala Asp Ala Pro Ala Tyr
            355                 360                 365
Gln Gln Gly Gln Asn Gln Leu Tyr Asn Glu Leu Asn Leu Gly Arg Arg
            370                 375                 380
Glu Glu Tyr Asp Val Leu Asp Lys Arg Gly Arg Asp Pro Glu Met
385                 390                 395                 400
Gly Gly Lys Pro Arg Arg Lys Asn Pro Gln Glu Gly Leu Tyr Asn Glu
                405                 410                 415
Leu Gln Lys Asp Lys Met Ala Glu Ala Tyr Ser Glu Ile Gly Met Lys
            420                 425                 430
Gly Glu Arg Arg Arg Gly Lys Gly His Asp Gly Leu Tyr Gln Gly Leu
            435                 440                 445
Ser Thr Ala Thr Lys Asp Thr Tyr Asp Ala Leu His Met Gln Ala Leu
```

Pro Pro Arg
465

<210> SEQ ID NO 113
<211> LENGTH: 650
<212> TYPE: PRT
<213> ORGANISM: artificial sequence
<220> FEATURE:
<223> OTHER INFORMATION: G3-v5 polypeptide CAR sequence

<400> SEQUENCE: 113

```
Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

Lys Ser Lys Ala Thr Leu Thr Ala Asp Thr Ser Ser Ser Thr Ala Tyr
65                  70                  75                  80

Met Gln Leu Ser Ser Leu Ala Ser Glu Asp Ser Ala Leu Tyr Tyr Cys
                85                  90                  95

Ala Arg Asp Gly Asn Tyr Tyr Ala Met Asp Tyr Trp Gly Gln Gly Thr
            100                 105                 110

Ser Val Thr Val Ser Ser Gly Gly Gly Ser Gly Gly Gly Gly Ser
            115                 120                 125

Gly Gly Gly Gly Ser Asp Ile Gln Met Thr Gln Thr Thr Ser Ser Leu
    130                 135                 140

Ser Ala Ser Leu Gly Asp Arg Val Thr Ile Thr Cys Arg Ala Ser Gln
145                 150                 155                 160

Asp Ile Asn Asn Tyr Leu Asn Trp Tyr Gln Gln Lys Pro Asp Gly Thr
                165                 170                 175

Val Lys Leu Leu Ile Tyr Tyr Thr Ser Ala Leu His Ser Gly Val Pro
            180                 185                 190

Ser Arg Phe Ser Gly Ser Gly Ser Gly Thr Asp Tyr Ser Leu Thr Ile
        195                 200                 205

Ser Asn Leu Glu Gln Glu Asp Ile Ala Thr Tyr Phe Cys Gln Gln Gly
    210                 215                 220

Asn Thr Leu Pro Pro Tyr Thr Phe Gly Gly Gly Thr Lys Leu Glu Ile
225                 230                 235                 240

Lys Glu Pro Lys Ser Pro Asp Lys Thr His Thr Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ala Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
```

340                 345                 350
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys Ile Tyr Ile Trp Ala Pro Leu Ala
465                 470                 475                 480

Gly Thr Cys Gly Val Leu Leu Leu Ser Leu Val Ile Thr Leu Tyr Cys
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
    530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
        595                 600                 605

Tyr Ser Glu Ile Gly Met Lys Gly Glu Arg Arg Arg Gly Lys Gly His
    610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 114
<211> LENGTH: 653
<212> TYPE: PRT
<213> ORGANISM: artificial sequence
<220> FEATURE:
<223> OTHER INFORMATION: G3-v6 polypeptide CAR sequence

<400> SEQUENCE: 114

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
                20                  25                  30

Trp Ile Asn Trp Val Lys Leu Arg Pro Gly Gln Gly Leu Glu Trp Ile
            35                  40                  45

Gly Glu Ile Tyr Pro Gly Ser Gly Ser Thr Asn Tyr Asn Glu Lys Phe

```
              50                  55                  60
Lys Ser Lys Ala Thr Leu Thr Ala Asp Thr Ser Ser Thr Ala Tyr
 65                  70                  75                  80

Met Gln Leu Ser Ser Leu Ala Ser Glu Asp Ser Ala Leu Tyr Tyr Cys
                 85                  90                  95

Ala Arg Asp Gly Asn Tyr Tyr Ala Met Asp Tyr Trp Gly Gln Gly Thr
             100                 105                 110

Ser Val Thr Val Ser Ser Gly Gly Gly Gly Ser Gly Gly Gly Gly Ser
             115                 120                 125

Gly Gly Gly Gly Ser Asp Ile Gln Met Thr Gln Thr Thr Ser Ser Leu
             130                 135                 140

Ser Ala Ser Leu Gly Asp Arg Val Thr Ile Thr Cys Arg Ala Ser Gln
145                 150                 155                 160

Asp Ile Asn Asn Tyr Leu Asn Trp Tyr Gln Gln Lys Pro Asp Gly Thr
                 165                 170                 175

Val Lys Leu Leu Ile Tyr Tyr Thr Ser Ala Leu His Ser Gly Val Pro
             180                 185                 190

Ser Arg Phe Ser Gly Ser Gly Ser Gly Thr Asp Tyr Ser Leu Thr Ile
             195                 200                 205

Ser Asn Leu Glu Gln Glu Asp Ile Ala Thr Tyr Phe Cys Gln Gln Gly
210                 215                 220

Asn Thr Leu Pro Pro Tyr Thr Phe Gly Gly Gly Thr Lys Leu Glu Ile
225                 230                 235                 240

Lys Glu Pro Lys Ser Pro Asp Lys Thr His Thr Cys Pro Pro Cys Pro
                 245                 250                 255

Ala Pro Pro Val Ala Gly Pro Ser Val Phe Leu Phe Pro Pro Lys Pro
             260                 265                 270

Lys Asp Thr Leu Met Ile Ala Arg Thr Pro Glu Val Thr Cys Val Val
             275                 280                 285

Val Asp Val Ser His Glu Asp Pro Glu Val Lys Phe Asn Trp Tyr Val
             290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                 325                 330                 335

Asp Trp Leu Asn Gly Lys Glu Tyr Lys Cys Lys Val Ser Asn Lys Ala
             340                 345                 350

Leu Pro Ala Pro Ile Glu Lys Thr Ile Ser Lys Ala Lys Gly Gln Pro
             355                 360                 365

Arg Glu Pro Gln Val Tyr Thr Leu Pro Pro Ser Arg Asp Glu Leu Thr
             370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                 405                 410                 415

Lys Thr Thr Pro Pro Val Leu Asp Ser Asp Gly Ser Phe Phe Leu Tyr
             420                 425                 430

Ser Lys Leu Thr Val Asp Lys Ser Arg Trp Gln Gln Gly Asn Val Phe
             435                 440                 445

Ser Cys Ser Val Met His Glu Ala Leu His Asn His Tyr Thr Gln Lys
             450                 455                 460

Ser Leu Ser Leu Ser Pro Gly Lys Ile Ile Ser Phe Phe Leu Ala Leu
465                 470                 475                 480
```

```
Thr Ser Thr Ala Leu Leu Phe Leu Leu Phe Leu Thr Leu Arg Phe
            485                 490                 495
Ser Val Val Lys Arg Gly Arg Lys Lys Leu Leu Tyr Ile Phe Lys Gln
                500                 505                 510
Pro Phe Met Arg Pro Val Gln Thr Thr Gln Glu Glu Asp Gly Cys Ser
            515                 520                 525
Cys Arg Phe Pro Glu Glu Glu Gly Gly Cys Glu Leu Arg Val Lys
    530                 535                 540
Phe Ser Arg Ser Ala Asp Ala Pro Ala Tyr Gln Gln Gly Gln Asn Gln
545                 550                 555                 560
Leu Tyr Asn Glu Leu Asn Leu Gly Arg Arg Glu Glu Tyr Asp Val Leu
                565                 570                 575
Asp Lys Arg Arg Gly Arg Asp Pro Glu Met Gly Gly Lys Pro Arg Arg
            580                 585                 590
Lys Asn Pro Gln Glu Gly Leu Tyr Asn Glu Leu Gln Lys Asp Lys Met
            595                 600                 605
Ala Glu Ala Tyr Ser Glu Ile Gly Met Lys Gly Glu Arg Arg Arg Gly
            610                 615                 620
Lys Gly His Asp Gly Leu Tyr Gln Gly Leu Ser Thr Ala Thr Lys Asp
625                 630                 635                 640
Thr Tyr Asp Ala Leu His Met Gln Ala Leu Pro Pro Arg
                645                 650

<210> SEQ ID NO 115
<211> LENGTH: 434
<212> TYPE: PRT
<213> ORGANISM: artificial sequence
<220> FEATURE:
<223> OTHER INFORMATION: H10-v1 polypeptide CAR sequence

<400> SEQUENCE: 115

Glu Val Lys Leu Val Glu Ser Gly Gly Gly Leu Val Lys Pro Gly Gly
1               5                   10                  15
Ser Leu Lys Leu Ser Cys Ala Ala Ser Gly Phe Thr Phe Ser Ser Tyr
                20                  25                  30
Ala Met Ser Trp Val Arg Gln Thr Pro Glu Lys Arg Leu Glu Trp Val
            35                  40                  45
Ala Ser Ile Ser Thr Gly Ala Ser Ala Tyr Phe Pro Asp Ser Val Lys
        50                  55                  60
Gly Arg Phe Thr Ile Ser Arg Asp Asn Ala Arg Asn Ile Leu Tyr Leu
65                  70                  75                  80
Gln Met Ser Ser Leu Arg Ser Glu Asp Thr Ala Met Tyr Tyr Cys Ala
                85                  90                  95
Arg Ile Thr Thr Ser Thr Trp Tyr Phe Asp Val Trp Gly Ala Gly Thr
            100                 105                 110
Thr Val Thr Val Ser Ser Gly Gly Gly Ser Gly Gly Gly Gly Ser
        115                 120                 125
Gly Gly Gly Gly Ser Asp Ile Lys Met Thr Gln Ser Pro Ser Ser Met
    130                 135                 140
Tyr Ala Ser Leu Gly Glu Arg Val Thr Ile Thr Cys Lys Ala Ser Gln
145                 150                 155                 160
Asp Ile Asn Ser Tyr Leu Ser Trp Phe Gln Gln Lys Pro Gly Lys Ser
                165                 170                 175
Pro Lys Thr Leu Ile Tyr Arg Ala Asn Arg Leu Val Asp Gly Val Pro
            180                 185                 190
```

```
Ser Arg Phe Ser Gly Ser Gly Ser Gly Gln Asp Tyr Ser Leu Thr Ile
        195                 200                 205

Ser Ser Leu Glu Tyr Glu Asp Met Gly Ile Tyr Tyr Cys Leu Gln Tyr
    210                 215                 220

Asp Glu Phe Pro Tyr Thr Phe Gly Gly Gly Thr Lys Leu Glu Ile Lys
225                 230                 235                 240

Gly Leu Ala Val Ser Thr Ile Ser Ser Phe Phe Pro Pro Gly Tyr Gln
                245                 250                 255

Ile Tyr Ile Trp Ala Pro Leu Ala Gly Thr Cys Gly Val Leu Leu Leu
            260                 265                 270

Ser Leu Val Ile Thr Leu Tyr Cys Lys Arg Gly Arg Lys Lys Leu Leu
        275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 116
<211> LENGTH: 437
<212> TYPE: PRT
<213> ORGANISM: artificial sequence
<220> FEATURE:
<223> OTHER INFORMATION: H10-v2 polypeptide CAR sequence

<400> SEQUENCE: 116

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110
```

Thr Val Thr Val Ser Ser Gly Gly Gly Ser Gly Gly Gly Ser
            115                 120                 125

Gly Gly Gly Gly Ser Asp Ile Lys Met Thr Gln Ser Pro Ser Met
130                 135                 140

Tyr Ala Ser Leu Gly Glu Arg Val Thr Ile Thr Cys Lys Ala Ser Gln
145                 150                 155                 160

Asp Ile Asn Ser Tyr Leu Ser Trp Phe Gln Gln Lys Pro Gly Lys Ser
                165                 170                 175

Pro Lys Thr Leu Ile Tyr Arg Ala Asn Arg Leu Val Asp Gly Val Pro
            180                 185                 190

Ser Arg Phe Ser Gly Ser Gly Ser Gly Gln Asp Tyr Ser Leu Thr Ile
        195                 200                 205

Ser Ser Leu Glu Tyr Glu Asp Met Gly Ile Tyr Tyr Cys Leu Gln Tyr
210                 215                 220

Asp Glu Phe Pro Tyr Thr Phe Gly Gly Gly Thr Lys Leu Glu Ile Lys
225                 230                 235                 240

Gly Leu Ala Val Ser Thr Ile Ser Phe Phe Pro Pro Gly Tyr Gln
                245                 250                 255

Ile Ile Ser Phe Phe Leu Ala Leu Thr Ser Thr Ala Leu Leu Phe Leu
        260                 265                 270

Leu Phe Phe Leu Thr Leu Arg Phe Ser Val Val Lys Arg Gly Arg Lys
    275                 280                 285

Lys Leu Leu Tyr Ile Phe Lys Gln Pro Phe Met Arg Pro Val Gln Thr
290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
        435

<210> SEQ ID NO 117
<211> LENGTH: 463
<212> TYPE: PRT
<213> ORGANISM: artificial sequence
<220> FEATURE:
<223> OTHER INFORMATION: H10-v3 polypeptide CAR sequence

<400> SEQUENCE: 117

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

```
Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
 50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Ile Thr Thr Ser Thr Trp Tyr Phe Asp Val Trp Gly Ala Gly Thr
                100                 105                 110

Thr Val Thr Val Ser Ser Gly Gly Gly Ser Gly Gly Gly Gly Ser
                115                 120                 125

Gly Gly Gly Gly Ser Asp Ile Lys Met Thr Gln Ser Pro Ser Ser Met
        130                 135                 140

Tyr Ala Ser Leu Gly Glu Arg Val Thr Ile Thr Cys Lys Ala Ser Gln
145                 150                 155                 160

Asp Ile Asn Ser Tyr Leu Ser Trp Phe Gln Lys Pro Gly Lys Ser
                165                 170                 175

Pro Lys Thr Leu Ile Tyr Arg Ala Asn Arg Leu Val Asp Gly Val Pro
                180                 185                 190

Ser Arg Phe Ser Gly Ser Gly Ser Gly Gln Asp Tyr Ser Leu Thr Ile
                195                 200                 205

Ser Ser Leu Glu Tyr Glu Asp Met Gly Ile Tyr Tyr Cys Leu Gln Tyr
                210                 215                 220

Asp Glu Phe Pro Tyr Thr Phe Gly Gly Gly Thr Lys Leu Glu Ile Lys
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
                260                 265                 270

Gly Ala Val His Thr Arg Gly Leu Asp Phe Ala Cys Asp Ile Tyr Ile
                275                 280                 285

Trp Ala Pro Leu Ala Gly Thr Cys Gly Val Leu Leu Leu Ser Leu Val
                290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Gly Gly Cys Glu Leu Arg
                340                 345                 350

Val Lys Phe Ser Arg Ser Ala Asp Ala Pro Ala Tyr Gln Gln Gly Gln
                355                 360                 365

Asn Gln Leu Tyr Asn Glu Leu Asn Leu Gly Arg Arg Glu Glu Tyr Asp
                370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
                420                 425                 430

Arg Gly Lys Gly His Asp Gly Leu Tyr Gln Gly Leu Ser Thr Ala Thr
                435                 440                 445

Lys Asp Thr Tyr Asp Ala Leu His Met Gln Ala Leu Pro Pro Arg
```

<210> SEQ ID NO 118
<211> LENGTH: 466
<212> TYPE: PRT
<213> ORGANISM: artificial sequence
<220> FEATURE:
<223> OTHER INFORMATION: H10-v4 polypeptide CAR sequence

<400> SEQUENCE: 118

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Lys Met Thr Gln Ser Pro Ser Ser Met
130                 135                 140

Tyr Ala Ser Leu Gly Glu Arg Val Thr Ile Thr Cys Lys Ala Ser Gln
145                 150                 155                 160

Asp Ile Asn Ser Tyr Leu Ser Trp Phe Gln Gln Lys Pro Gly Lys Ser
                165                 170                 175

Pro Lys Thr Leu Ile Tyr Arg Ala Asn Arg Leu Val Asp Gly Val Pro
            180                 185                 190

Ser Arg Phe Ser Gly Ser Gly Ser Gly Gln Asp Tyr Ser Leu Thr Ile
        195                 200                 205

Ser Ser Leu Glu Tyr Glu Asp Met Gly Ile Tyr Tyr Cys Leu Gln Tyr
    210                 215                 220

Asp Glu Phe Pro Tyr Thr Phe Gly Gly Gly Thr Lys Leu Glu Ile Lys
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Ile Ser
        275                 280                 285

Phe Phe Leu Ala Leu Thr Ser Thr Ala Leu Leu Phe Leu Leu Phe Phe
    290                 295                 300

Leu Thr Leu Arg Phe Ser Val Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
```

```
              355                 360                 365
Gln Gly Gln Asn Gln Leu Tyr Asn Glu Leu Asn Leu Gly Arg Arg Glu
            370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 119
<211> LENGTH: 649
<212> TYPE: PRT
<213> ORGANISM: artificial sequence
<220> FEATURE:
<223> OTHER INFORMATION: H10-v5 polypeptide CAR sequence

<400> SEQUENCE: 119

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Lys Met Thr Gln Ser Pro Ser Ser Met
    130                 135                 140

Tyr Ala Ser Leu Gly Glu Arg Val Thr Ile Thr Cys Lys Ala Ser Gln
145                 150                 155                 160

Asp Ile Asn Ser Tyr Leu Ser Trp Phe Gln Gln Lys Pro Gly Lys Ser
                165                 170                 175

Pro Lys Thr Leu Ile Tyr Arg Ala Asn Arg Leu Val Asp Gly Val Pro
            180                 185                 190

Ser Arg Phe Ser Gly Ser Gly Ser Gly Gln Asp Tyr Ser Leu Thr Ile
        195                 200                 205

Ser Ser Leu Glu Tyr Glu Asp Met Gly Ile Tyr Tyr Cys Leu Gln Tyr
    210                 215                 220

Asp Glu Phe Pro Tyr Thr Phe Gly Gly Gly Thr Lys Leu Glu Ile Lys
225                 230                 235                 240

Glu Pro Lys Ser Pro Asp Lys Thr His Thr Cys Pro Pro Cys Pro Ala
```

```
                245                 250                 255
Pro Pro Val Ala Gly Pro Ser Val Phe Leu Phe Pro Lys Pro Lys
            260                 265                 270

Asp Thr Leu Met Ile Ala Arg Thr Pro Glu Val Thr Cys Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys Ile Tyr Ile Trp Ala Pro Leu Ala Gly
465                 470                 475                 480

Thr Cys Gly Val Leu Leu Leu Ser Leu Val Ile Thr Leu Tyr Cys Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
            515                 520                 525

Glu Glu Glu Glu Gly Gly Cys Glu Leu Arg Val Lys Phe Ser Arg Ser
            530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
            595                 600                 605

Ser Glu Ile Gly Met Lys Gly Glu Arg Arg Arg Gly Lys Gly His Asp
            610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 120
```

<211> LENGTH: 652
<212> TYPE: PRT
<213> ORGANISM: artificial sequence
<220> FEATURE:
<223> OTHER INFORMATION: H10-v6 polypeptide CAR sequence

<400> SEQUENCE: 120

```
Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Lys Met Thr Gln Ser Pro Ser Ser Met
    130                 135                 140

Tyr Ala Ser Leu Gly Glu Arg Val Thr Ile Thr Cys Lys Ala Ser Gln
145                 150                 155                 160

Asp Ile Asn Ser Tyr Leu Ser Trp Phe Gln Gln Lys Pro Gly Lys Ser
                165                 170                 175

Pro Lys Thr Leu Ile Tyr Arg Ala Asn Arg Leu Val Asp Gly Val Pro
            180                 185                 190

Ser Arg Phe Ser Gly Ser Gly Ser Gln Asp Tyr Ser Leu Thr Ile
        195                 200                 205

Ser Ser Leu Glu Tyr Glu Asp Met Gly Ile Tyr Tyr Cys Leu Gln Tyr
    210                 215                 220

Asp Glu Phe Pro Tyr Thr Phe Gly Gly Gly Thr Lys Leu Glu Ile Lys
225                 230                 235                 240

Glu Pro Lys Ser Pro Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ala Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380
```

-continued

```
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys Ile Ile Ser Phe Phe Leu Ala Leu Thr
465                 470                 475                 480
Ser Thr Ala Leu Leu Phe Leu Leu Phe Phe Leu Thr Leu Arg Phe Ser
                485                 490                 495
Val Val Lys Arg Gly Arg Lys Lys Leu Leu Tyr Ile Phe Lys Gln Pro
            500                 505                 510
Phe Met Arg Pro Val Gln Thr Thr Gln Glu Glu Asp Gly Cys Ser Cys
        515                 520                 525
Arg Phe Pro Glu Glu Glu Glu Gly Gly Cys Glu Leu Arg Val Lys Phe
    530                 535                 540
Ser Arg Ser Ala Asp Ala Pro Ala Tyr Gln Gln Gly Gln Asn Gln Leu
545                 550                 555                 560
Tyr Asn Glu Leu Asn Leu Gly Arg Arg Glu Glu Tyr Asp Val Leu Asp
                565                 570                 575
Lys Arg Arg Gly Arg Asp Pro Glu Met Gly Gly Lys Pro Arg Arg Lys
            580                 585                 590
Asn Pro Gln Glu Gly Leu Tyr Asn Glu Leu Gln Lys Asp Lys Met Ala
        595                 600                 605
Glu Ala Tyr Ser Glu Ile Gly Met Lys Gly Glu Arg Arg Arg Gly Lys
    610                 615                 620
Gly His Asp Gly Leu Tyr Gln Gly Leu Ser Thr Ala Thr Lys Asp Thr
625                 630                 635                 640
Tyr Asp Ala Leu His Met Gln Ala Leu Pro Pro Arg
                645                 650

<210> SEQ ID NO 121
<211> LENGTH: 455
<212> TYPE: PRT
<213> ORGANISM: artificial sequence
<220> FEATURE:
<223> OTHER INFORMATION: Humanized H10-v1 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
```

<220> FEATURE:
<221> NAME/KEY: VARIANT
<222> LOCATION: (233)....(233)
<223> OTHER INFORMATION: /replace= " Tyr"

<400> SEQUENCE: 121

```
Met Ala Leu Pro Val Thr Ala Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ala Ser Ile Ser Thr Gly Ala Ser Ala Tyr Phe
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Arg Ile Thr Thr Ser Thr Trp Tyr Phe Asp Val
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Ile Asn Ser Tyr Leu Ser Trp Phe Gln Gln
            180                 185                 190

Lys Pro Gly Lys Ala Pro Lys Thr Leu Ile Tyr Arg Ala Asn Arg Leu
        195                 200                 205

Gln Ser Gly Val Pro Ser Arg Phe Ser Gly Ser Gly Ser Gly Gln Asp
210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
                245                 250                 255

Lys Leu Glu Ile Lys Gly Leu Ala Val Ser Thr Ile Ser Ser Phe Phe
            260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
370                 375                 380
```

```
Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
            405                 410                 415

Ile Gly Met Lys Gly Glu Arg Arg Arg Gly Lys Gly His Asp Gly Leu
        420                 425                 430

Tyr Gln Gly Leu Ser Thr Ala Thr Lys Asp Thr Tyr Asp Ala Leu His
        435                 440                 445

Met Gln Ala Leu Pro Pro Arg
        450                 455
```

<210> SEQ ID NO 122
<211> LENGTH: 458
<212> TYPE: PRT
<213> ORGANISM: artificial sequence
<220> FEATURE:
<223> OTHER INFORMATION: Humanized H10-v2 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
<220> FEATURE:
<221> NAME/KEY: VARIANT
<222> LOCATION: (233)....(233)
<223> OTHER INFORMATION: /replace= " Tyr"

<400> SEQUENCE: 122

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ala Ser Ile Ser Thr Gly Ala Ser Ala Tyr Phe
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Arg Ile Thr Thr Ser Thr Trp Tyr Phe Asp Val
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Asp Ile Gln Met Thr Gln
145                 150                 155                 160
```

-continued

```
Ser Pro Ser Ser Leu Ser Ala Ser Val Gly Asp Arg Val Thr Ile Thr
            165                 170                 175

Cys Arg Ala Ser Gln Asp Ile Asn Ser Tyr Leu Ser Trp Phe Gln Gln
        180                 185                 190

Lys Pro Gly Lys Ala Pro Lys Thr Leu Ile Tyr Arg Ala Asn Arg Leu
    195                 200                 205

Gln Ser Gly Val Pro Ser Arg Phe Ser Gly Ser Gly Ser Gly Gln Asp
210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
            245                 250                 255

Lys Leu Glu Ile Lys Gly Leu Ala Val Ser Thr Ile Ser Ser Phe Phe
        260                 265                 270

Pro Pro Gly Tyr Gln Ile Ile Ser Phe Phe Leu Ala Leu Thr Ser Thr
    275                 280                 285

Ala Leu Leu Phe Leu Leu Phe Phe Leu Thr Leu Arg Phe Ser Val Val
290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
            325                 330                 335

Pro Glu Glu Glu Glu Gly Gly Cys Glu Leu Arg Val Lys Phe Ser Arg
        340                 345                 350

Ser Ala Asp Ala Pro Ala Tyr Gln Gln Gly Gln Asn Gln Leu Tyr Asn
    355                 360                 365

Glu Leu Asn Leu Gly Arg Arg Glu Glu Tyr Asp Val Leu Asp Lys Arg
370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
            405                 410                 415

Tyr Ser Glu Ile Gly Met Lys Gly Glu Arg Arg Arg Gly Lys Gly His
        420                 425                 430

Asp Gly Leu Tyr Gln Gly Leu Ser Thr Ala Thr Lys Asp Thr Tyr Asp
    435                 440                 445

Ala Leu His Met Gln Ala Leu Pro Pro Arg
450                 455
```

```
<210> SEQ ID NO 123
<211> LENGTH: 484
<212> TYPE: PRT
<213> ORGANISM: artificial sequence
<220> FEATURE:
<223> OTHER INFORMATION: Humanized H10-v3 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
```

```
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
<220> FEATURE:
<221> NAME/KEY: VARIANT
<222> LOCATION: (233)....(233)
<223> OTHER INFORMATION: /replace= " Tyr"

<400> SEQUENCE: 123

Met Ala Leu Pro Val Thr Ala Leu Leu Leu Pro Leu Ala Leu Leu Leu
 1               5                  10                  15

His Ala Ala Arg Pro Glu Val Gln Leu Val Glu Ser Gly Gly Gly Leu
             20                  25                  30

Val Lys Pro Gly Gly Ser Leu Arg Leu Ser Cys Ala Ala Ser Gly Phe
         35                  40                  45

Thr Phe Ser Ser Tyr Ala Met Ser Trp Val Arg Gln Ala Pro Gly Lys
     50                  55                  60

Gly Leu Glu Trp Val Ala Ser Ile Ser Thr Gly Ala Ser Ala Tyr Phe
 65                  70                  75                  80

Ala Asp Ser Val Lys Gly Arg Phe Thr Ile Ser Arg Asp Asn Ala Lys
                 85                  90                  95

Asn Ser Leu Tyr Leu Gln Met Asn Ser Leu Arg Ala Glu Asp Thr Ala
            100                 105                 110

Val Tyr Tyr Cys Ala Arg Ile Thr Thr Ser Thr Trp Tyr Phe Asp Val
        115                 120                 125

Trp Gly Gln Gly Thr Thr Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Ile Asn Ser Tyr Leu Ser Trp Phe Gln Gln
            180                 185                 190

Lys Pro Gly Lys Ala Pro Lys Thr Leu Ile Tyr Arg Ala Asn Arg Leu
        195                 200                 205

Gln Ser Gly Val Pro Ser Arg Phe Ser Gly Ser Gly Ser Gly Gln Asp
210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
                245                 250                 255

Lys Leu Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
```

```
                    355                 360                 365

Gly Cys Glu Leu Arg Val Lys Phe Ser Arg Ser Ala Asp Ala Pro Ala
            370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
            450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 124
<211> LENGTH: 487
<212> TYPE: PRT
<213> ORGANISM: artificial sequence
<220> FEATURE:
<223> OTHER INFORMATION: Humanized H10-v4 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
<220> FEATURE:
<221> NAME/KEY: VARIANT
<222> LOCATION: (233)....(233)
<223> OTHER INFORMATION: /replace= " Tyr"
<223> OTHER INFORMATION: Humanized H10-v4 polypeptide CAR sequence

<400> SEQUENCE: 124

Met Ala Leu Pro Val Thr Ala Leu Leu Leu Pro Leu Ala Leu Leu Leu
1                5                  10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ala Ser Ile Ser Thr Gly Ala Ser Ala Tyr Phe
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
```

```
            100                 105                 110
Val Tyr Tyr Cys Ala Arg Ile Thr Thr Ser Thr Trp Tyr Phe Asp Val
            115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Ile Asn Ser Tyr Leu Ser Trp Phe Gln Gln
            180                 185                 190

Lys Pro Gly Lys Ala Pro Lys Thr Leu Ile Tyr Arg Ala Asn Arg Leu
            195                 200                 205

Gln Ser Gly Val Pro Ser Arg Phe Ser Gly Ser Gly Ser Gly Gln Asp
        210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
                245                 250                 255

Lys Leu Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 125
<211> LENGTH: 670
<212> TYPE: PRT
<213> ORGANISM: artificial sequence
```

```
<220> FEATURE:
<223> OTHER INFORMATION: Humanized H10-v5 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
<220> FEATURE:
<221> NAME/KEY: VARIANT
<222> LOCATION: (233)....(233)
<223> OTHER INFORMATION: /replace= " Tyr"

<400> SEQUENCE: 125

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ala Ser Ile Ser Thr Gly Ala Ser Ala Tyr Phe
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Arg Ile Thr Thr Ser Thr Trp Tyr Phe Asp Val
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Ile Asn Ser Tyr Leu Ser Trp Phe Gln Gln
            180                 185                 190

Lys Pro Gly Lys Ala Pro Lys Thr Leu Ile Tyr Arg Ala Asn Arg Leu
        195                 200                 205

Gln Ser Gly Val Pro Ser Arg Phe Ser Gly Ser Gly Ser Gly Gln Asp
    210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
                245                 250                 255

Lys Leu Glu Ile Lys Glu Pro Lys Ser Pro Asp Lys Thr His Thr Cys
            260                 265                 270
```

```
Pro Pro Cys Pro Ala Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
        515                 520                 525

Gln Pro Phe Met Arg Pro Val Gln Thr Thr Gln Glu Glu Asp Gly Cys
    530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
        595                 600                 605

Arg Lys Asn Pro Gln Glu Gly Leu Tyr Asn Glu Leu Gln Lys Asp Lys
    610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 126
<211> LENGTH: 673
```

```
<212> TYPE: PRT
<213> ORGANISM: artificial sequence
<220> FEATURE:
<223> OTHER INFORMATION: Humanized H10-v6 polypeptide CAR sequence
<220> FEATURE:
<221> NAME/KEY: VARIANT
<222> LOCATION: (24)....(24)
<223> OTHER INFORMATION: /replace= " Lys"
<220> FEATURE:
<221> NAME/KEY: VARIANT
<222> LOCATION: (81)....(81)
<223> OTHER INFORMATION: /replace= " Pro"
<220> FEATURE:
<221> NAME/KEY: VARIANT
<222> LOCATION: (112)....(112)
<223> OTHER INFORMATION: /replace= " Met"
<220> FEATURE:
<221> NAME/KEY: VARIANT
<222> LOCATION: (156)....(156)
<223> OTHER INFORMATION: /replace= " Lys"
<220> FEATURE:
<221> NAME/KEY: VARIANT
<222> LOCATION: (208)....(208)
<223> OTHER INFORMATION: /replace= " Val"
<220> FEATURE:
<221> NAME/KEY: VARIANT
<222> LOCATION: (233)....(233)
<223> OTHER INFORMATION: /replace= " Tyr"

<400> SEQUENCE: 126

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ala Ser Ile Ser Thr Gly Ala Ser Ala Tyr Phe
65                  70                  75                  80

Ala Asp Ser Val Lys Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Arg Ile Thr Thr Ser Thr Trp Tyr Phe Asp Val
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Asp Ile Asn Ser Tyr Leu Ser Trp Phe Gln Gln
            180                 185                 190

Lys Pro Gly Lys Ala Pro Lys Thr Leu Ile Tyr Arg Ala Asn Arg Leu
        195                 200                 205

Gln Ser Gly Val Pro Ser Arg Phe Ser Gly Ser Gly Ser Gly Gln Asp
    210                 215                 220

Tyr Thr Leu Thr Ile Ser Ser Leu Gln Pro Glu Asp Phe Ala Thr Tyr
225                 230                 235                 240

Tyr Cys Leu Gln Tyr Asp Glu Phe Pro Tyr Thr Phe Gly Gln Gly Thr
                245                 250                 255
```

-continued

```
Lys Leu Glu Ile Lys Glu Pro Lys Ser Pro Asp Lys Thr His Thr Cys
              260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Ile Ser Phe
                485                 490                 495

Phe Leu Ala Leu Thr Ser Thr Ala Leu Leu Phe Leu Leu Phe Phe Leu
            500                 505                 510

Thr Leu Arg Phe Ser Val Val Lys Arg Gly Arg Lys Lys Leu Leu Tyr
        515                 520                 525

Ile Phe Lys Gln Pro Phe Met Arg Pro Val Gln Thr Thr Gln Glu Glu
    530                 535                 540

Asp Gly Cys Ser Cys Arg Phe Pro Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg
```

<210> SEQ ID NO 127
<211> LENGTH: 430
<212> TYPE: PRT
<213> ORGANISM: artificial sequence
<220> FEATURE:
<223> OTHER INFORMATION: 2A4-v1 polypeptide CAR sequence

<400> SEQUENCE: 127

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile Asn Pro Asn Asn Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
                100                 105                 110

Ser Ser Gly Gly Gly Gly Ser Gly Gly Gly Ser Gly Gly Gly Gly
            115                 120                 125

Ser Met Glu Ile Glu Ile Thr Gln Thr Pro Ala Leu Met Ser Ala Ser
130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
                165                 170                 175

Ile Tyr Leu Thr Ser Asn Leu Ala Ser Gly Val Pro Ala Arg Phe Ser
            180                 185                 190

Gly Ser Gly Ser Gly Thr Ser Tyr Ser Leu Thr Ile Ser Ser Met Glu
        195                 200                 205

Ala Glu Asp Ala Ala Thr Tyr Tyr Cys Gln Gln Trp Ser Ser Asn Pro
    210                 215                 220

Tyr Thr Phe Gly Gly Gly Thr Arg Leu Glu Leu Lys Gly Leu Ala Val
225                 230                 235                 240

Ser Thr Ile Ser Ser Phe Phe Pro Pro Gly Tyr Gln Ile Tyr Ile Trp
                245                 250                 255

Ala Pro Leu Ala Gly Thr Cys Gly Val Leu Leu Leu Ser Leu Val Ile
            260                 265                 270

Thr Leu Tyr Cys Lys Arg Gly Arg Lys Lys Leu Leu Tyr Ile Phe Lys
        275                 280                 285

Gln Pro Phe Met Arg Pro Val Gln Thr Thr Gln Glu Glu Asp Gly Cys
    290                 295                 300

Ser Cys Arg Phe Pro Glu Glu Glu Glu Gly Gly Cys Glu Leu Arg Val
305                 310                 315                 320

Lys Phe Ser Arg Ser Ala Asp Ala Pro Ala Tyr Gln Gln Gly Gln Asn
                325                 330                 335

Gln Leu Tyr Asn Glu Leu Asn Leu Gly Arg Arg Glu Glu Tyr Asp Val
            340                 345                 350

Leu Asp Lys Arg Arg Gly Arg Asp Pro Glu Met Gly Gly Lys Pro Arg
        355                 360                 365

Arg Lys Asn Pro Gln Glu Gly Leu Tyr Asn Glu Leu Gln Lys Asp Lys
    370                 375                 380

Met Ala Glu Ala Tyr Ser Glu Ile Gly Met Lys Gly Glu Arg Arg Arg
385                 390                 395                 400

Gly Lys Gly His Asp Gly Leu Tyr Gln Gly Leu Ser Thr Ala Thr Lys
                405                 410                 415

Asp Thr Tyr Asp Ala Leu His Met Gln Ala Leu Pro Pro Arg
            420                 425                 430

<210> SEQ ID NO 128
<211> LENGTH: 433
<212> TYPE: PRT
<213> ORGANISM: artificial sequence
<220> FEATURE:
<223> OTHER INFORMATION: 2A4-v2 polypeptide CAR sequence

<400> SEQUENCE: 128

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser Gly Gly Gly Ser Gly Gly Gly Ser Gly Gly Gly Gly
        115                 120                 125

Ser Met Glu Ile Glu Ile Thr Gln Thr Pro Ala Leu Met Ser Ala Ser
    130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
                165                 170                 175

Ile Tyr Leu Thr Ser Asn Leu Ala Ser Gly Val Pro Ala Arg Phe Ser
            180                 185                 190

Gly Ser Gly Ser Gly Thr Ser Tyr Ser Leu Thr Ile Ser Ser Met Glu
        195                 200                 205

Ala Glu Asp Ala Ala Thr Tyr Tyr Cys Gln Gln Trp Ser Ser Asn Pro
    210                 215                 220

Tyr Thr Phe Gly Gly Gly Thr Arg Leu Glu Leu Lys Gly Leu Ala Val
225                 230                 235                 240

Ser Thr Ile Ser Ser Phe Phe Pro Pro Gly Tyr Gln Ile Ile Ser Phe
                245                 250                 255

Phe Leu Ala Leu Thr Ser Thr Ala Leu Leu Phe Leu Leu Phe Phe Leu
            260                 265                 270

Thr Leu Arg Phe Ser Val Val Lys Arg Gly Arg Lys Lys Leu Leu Tyr
        275                 280                 285

Ile Phe Lys Gln Pro Phe Met Arg Pro Val Gln Thr Thr Gln Glu Glu
    290                 295                 300

```
Asp Gly Cys Ser Cys Arg Phe Pro Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 129
<211> LENGTH: 459
<212> TYPE: PRT
<213> ORGANISM: artificial sequence
<220> FEATURE:
<223> OTHER INFORMATION: 2A4-v3 polypeptide CAR sequence

<400> SEQUENCE: 129

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile Asn Pro Asn Asn Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser Gly Gly Gly Gly Ser Gly Gly Gly Ser Gly Gly Gly Gly
            115                 120                 125

Ser Met Glu Ile Glu Ile Thr Gln Thr Pro Ala Leu Met Ser Ala Ser
        130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
                165                 170                 175

Ile Tyr Leu Thr Ser Asn Leu Ala Ser Gly Val Pro Ala Arg Phe Ser
            180                 185                 190

Gly Ser Gly Ser Gly Thr Ser Tyr Ser Leu Thr Ile Ser Ser Met Glu
        195                 200                 205

Ala Glu Asp Ala Ala Thr Tyr Tyr Cys Gln Gln Trp Ser Ser Asn Pro
210                 215                 220
```

Tyr Thr Phe Gly Gly Gly Thr Arg Leu Glu Leu Lys Thr Thr Thr Pro
225                 230                 235                 240

Ala Pro Arg Pro Pro Thr Pro Ala Pro Thr Ile Ala Ser Gln Pro Leu
            245                 250                 255

Ser Leu Arg Pro Glu Ala Cys Arg Pro Ala Ala Gly Gly Ala Val His
            260                 265                 270

Thr Arg Gly Leu Asp Phe Ala Cys Asp Ile Tyr Ile Trp Ala Pro Leu
            275                 280                 285

Ala Gly Thr Cys Gly Val Leu Leu Ser Leu Val Ile Thr Leu Tyr
290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
            325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
        355                 360                 365

Asn Glu Leu Asn Leu Gly Arg Arg Glu Glu Tyr Asp Val Leu Asp Lys
370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
            405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
            435                 440                 445

Asp Ala Leu His Met Gln Ala Leu Pro Pro Arg
450                 455

<210> SEQ ID NO 130
<211> LENGTH: 462
<212> TYPE: PRT
<213> ORGANISM: artificial sequence
<220> FEATURE:
<223> OTHER INFORMATION: 2A4-v4 polypeptide CAR sequence

<400> SEQUENCE: 130

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser Gly Gly Gly Gly Ser Gly Gly Gly Ser Gly Gly Gly Gly
            115                 120                 125

Ser Met Glu Ile Glu Ile Thr Gln Thr Pro Ala Leu Met Ser Ala Ser
130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
                165                 170                 175

Ile Tyr Leu Thr Ser Asn Leu Ala Ser Gly Val Pro Ala Arg Phe Ser
                180                 185                 190

Gly Ser Gly Ser Gly Thr Ser Tyr Ser Leu Thr Ile Ser Ser Met Glu
                195                 200                 205

Ala Glu Asp Ala Ala Thr Tyr Tyr Cys Gln Gln Trp Ser Ser Asn Pro
210                 215                 220

Tyr Thr Phe Gly Gly Gly Thr Arg Leu Glu Leu Lys Thr Thr Thr Pro
225                 230                 235                 240

Ala Pro Arg Pro Pro Thr Pro Ala Pro Thr Ile Ala Ser Gln Pro Leu
                245                 250                 255

Ser Leu Arg Pro Glu Ala Cys Arg Pro Ala Ala Gly Gly Ala Val His
                260                 265                 270

Thr Arg Gly Leu Asp Phe Ala Cys Asp Ile Ile Ser Phe Phe Leu Ala
                275                 280                 285

Leu Thr Ser Thr Ala Leu Leu Phe Leu Leu Phe Phe Leu Thr Leu Arg
                290                 295                 300

Phe Ser Val Val Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Gly Gly Cys Glu Leu Arg Val
                340                 345                 350

Lys Phe Ser Arg Ser Ala Asp Ala Pro Ala Tyr Gln Gln Gly Gln Asn
                355                 360                 365

Gln Leu Tyr Asn Glu Leu Asn Leu Gly Arg Arg Glu Glu Tyr Asp Val
370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
                435                 440                 445

Asp Thr Tyr Asp Ala Leu His Met Gln Ala Leu Pro Pro Arg
450                 455                 460

<210> SEQ ID NO 131
<211> LENGTH: 645
<212> TYPE: PRT
<213> ORGANISM: artificial sequence
<220> FEATURE:
<223> OTHER INFORMATION: 2A4-v5 polypeptide CAR sequence

<400> SEQUENCE: 131

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

```
Thr Met His Trp Val Lys Gln Ser His Gly Lys Ser Leu Glu Trp Ile
         35                  40                  45

Gly Gly Ile Asn Pro Asn Asn Gly Gly Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Leu Gln Gly Phe Ala Tyr Trp Gly Gln Gly Thr Pro Leu Thr Val
            100                 105                 110

Ser Ser Gly Gly Gly Ser Gly Gly Gly Gly Ser Gly Gly Gly Gly
            115                 120                 125

Ser Met Glu Ile Glu Ile Thr Gln Thr Pro Ala Leu Met Ser Ala Ser
    130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
                165                 170                 175

Ile Tyr Leu Thr Ser Asn Leu Ala Ser Gly Val Pro Ala Arg Phe Ser
            180                 185                 190

Gly Ser Gly Ser Gly Thr Ser Tyr Ser Leu Thr Ile Ser Ser Met Glu
            195                 200                 205

Ala Glu Asp Ala Ala Thr Tyr Tyr Cys Gln Gln Trp Ser Ser Asn Pro
    210                 215                 220

Tyr Thr Phe Gly Gly Gly Thr Arg Leu Glu Leu Lys Glu Pro Lys Ser
225                 230                 235                 240

Pro Asp Lys Thr His Thr Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ala Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
```

-continued

```
                450                 455                 460
Pro Gly Lys Ile Tyr Ile Trp Ala Pro Leu Ala Gly Thr Cys Gly Val
465                 470                 475                 480

Leu Leu Leu Ser Leu Val Ile Thr Leu Tyr Cys Lys Arg Gly Arg Lys
                485                 490                 495

Lys Leu Leu Tyr Ile Phe Lys Gln Pro Phe Met Arg Pro Val Gln Thr
                500                 505                 510

Thr Gln Glu Glu Asp Gly Cys Ser Cys Arg Phe Pro Glu Glu Glu
                515                 520                 525

Gly Gly Cys Glu Leu Arg Val Lys Phe Ser Arg Ser Ala Asp Ala Pro
                530                 535                 540

Ala Tyr Gln Gln Gly Gln Asn Gln Leu Tyr Asn Glu Leu Asn Leu Gly
545                 550                 555                 560

Arg Arg Glu Glu Tyr Asp Val Leu Asp Lys Arg Arg Gly Arg Asp Pro
                565                 570                 575

Glu Met Gly Gly Lys Pro Arg Arg Lys Asn Pro Gln Glu Gly Leu Tyr
                580                 585                 590

Asn Glu Leu Gln Lys Asp Lys Met Ala Glu Ala Tyr Ser Glu Ile Gly
                595                 600                 605

Met Lys Gly Glu Arg Arg Arg Gly Lys Gly His Asp Gly Leu Tyr Gln
                610                 615                 620

Gly Leu Ser Thr Ala Thr Lys Asp Thr Tyr Asp Ala Leu His Met Gln
625                 630                 635                 640

Ala Leu Pro Pro Arg
                645

<210> SEQ ID NO 132
<211> LENGTH: 648
<212> TYPE: PRT
<213> ORGANISM: artificial sequence
<220> FEATURE:
<223> OTHER INFORMATION: 2A4-v6 polypeptide CAR sequence

<400> SEQUENCE: 132

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
                35                  40                  45

Gly Gly Ile Asn Pro Asn Asn Gly Gly Thr Ser Tyr Asn Gln Lys Phe
                50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
                100                 105                 110

Ser Ser Gly Gly Gly Gly Ser Gly Gly Gly Ser Gly Gly Gly Gly
                115                 120                 125

Ser Met Glu Ile Glu Ile Thr Gln Thr Pro Ala Leu Met Ser Ala Ser
                130                 135                 140

Pro Gly Glu Lys Val Thr Met Thr Cys Ser Ala Ser Ser Ser Val Ser
145                 150                 155                 160

Tyr Met Tyr Trp Tyr Gln Gln Lys Pro Arg Ser Ser Pro Lys Pro Trp
```

-continued

```
                165                 170                 175
Ile Tyr Leu Thr Ser Asn Leu Ala Ser Gly Val Pro Ala Arg Phe Ser
            180                 185                 190

Gly Ser Gly Ser Gly Thr Ser Tyr Ser Leu Thr Ile Ser Ser Met Glu
        195                 200                 205

Ala Glu Asp Ala Ala Thr Tyr Tyr Cys Gln Gln Trp Ser Ser Asn Pro
    210                 215                 220

Tyr Thr Phe Gly Gly Gly Thr Arg Leu Glu Leu Lys Glu Pro Lys Ser
225                 230                 235                 240

Pro Asp Lys Thr His Thr Cys Pro Pro Cys Pro Ala Pro Pro Val Ala
                245                 250                 255

Gly Pro Ser Val Phe Leu Phe Pro Pro Lys Pro Lys Asp Thr Leu Met
                260                 265                 270

Ile Ala Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys Ile Ile Ser Phe Phe Leu Ala Leu Thr Ser Thr Ala Leu
465                 470                 475                 480

Leu Phe Leu Leu Phe Phe Leu Thr Leu Arg Phe Ser Val Val Lys Arg
                485                 490                 495

Gly Arg Lys Lys Leu Leu Tyr Ile Phe Lys Gln Pro Phe Met Arg Pro
                500                 505                 510

Val Gln Thr Thr Gln Glu Glu Asp Gly Cys Ser Cys Arg Phe Pro Glu
            515                 520                 525

Glu Glu Glu Gly Gly Cys Glu Leu Arg Val Lys Phe Ser Arg Ser Ala
        530                 535                 540

Asp Ala Pro Ala Tyr Gln Gln Gly Gln Asn Gln Leu Tyr Asn Glu Leu
545                 550                 555                 560

Asn Leu Gly Arg Arg Glu Glu Tyr Asp Val Leu Asp Lys Arg Arg Gly
                565                 570                 575

Arg Asp Pro Glu Met Gly Gly Lys Pro Arg Arg Lys Asn Pro Gln Glu
                580                 585                 590
```

```
Gly Leu Tyr Asn Glu Leu Gln Lys Asp Lys Met Ala Glu Ala Tyr Ser
            595                 600                 605

Glu Ile Gly Met Lys Gly Glu Arg Arg Arg Gly Lys Gly His Asp Gly
610                 615                 620

Leu Tyr Gln Gly Leu Ser Thr Ala Thr Lys Asp Thr Tyr Asp Ala Leu
625                 630                 635                 640

His Met Gln Ala Leu Pro Pro Arg
                645

<210> SEQ ID NO 133
<211> LENGTH: 436
<212> TYPE: PRT
<213> ORGANISM: artificial sequence
<220> FEATURE:
<223> OTHER INFORMATION: 1C11-v1 polypeptide CAR sequence

<400> SEQUENCE: 133

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Val Leu Trp Leu Arg Gly Asp Tyr Trp Gly Gln Gly
                100                 105                 110

Thr Ile Leu Thr Val Ser Ala Gly Gly Gly Ser Gly Gly Gly Gly
            115                 120                 125

Ser Gly Gly Gly Gly Ser Met Glu Val Leu Ile Thr Gln Thr Pro Ser
    130                 135                 140

Ser Leu Ser Ala Ser Leu Gly Glu Arg Val Ser Leu Thr Cys Arg Ala
145                 150                 155                 160

Ser Gln Asp Ile Gly Ser Ser Leu Asn Trp Leu Gln Gln Glu Pro Asp
                165                 170                 175

Gly Thr Ile Lys Arg Leu Ile Tyr Ala Thr Ser Ser Leu Asp Ser Gly
            180                 185                 190

Val Pro Lys Arg Phe Ser Gly Ser Arg Ser Gly Ser Asp Tyr Ser Leu
        195                 200                 205

Thr Ile Ser Ser Leu Glu Ser Glu Asp Phe Val Asp Tyr Tyr Cys Leu
    210                 215                 220

Gln Tyr Ala Ser Ser Pro Tyr Thr Phe Gly Gly Gly Thr Lys Leu Glu
225                 230                 235                 240

Leu Lys Gly Leu Ala Val Ser Thr Ile Ser Ser Phe Phe Pro Pro Gly
                245                 250                 255

Tyr Gln Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300
```

Gln Glu Glu Asp Gly Cys Ser Cys Arg Phe Pro Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 134
<211> LENGTH: 439
<212> TYPE: PRT
<213> ORGANISM: artificial sequence
<220> FEATURE:
<223> OTHER INFORMATION: 1C11-v2 polypeptide CAR sequence

<400> SEQUENCE: 134

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Glu Tyr Asn Gln Lys Phe
        50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Val Leu Trp Leu Arg Arg Gly Asp Tyr Trp Gly Gln Gly
            100                 105                 110

Thr Ile Leu Thr Val Ser Ala Gly Gly Gly Gly Ser Gly Gly Gly Gly
        115                 120                 125

Ser Gly Gly Gly Gly Ser Met Glu Val Leu Ile Thr Gln Thr Pro Ser
    130                 135                 140

Ser Leu Ser Ala Ser Leu Gly Glu Arg Val Ser Leu Thr Cys Arg Ala
145                 150                 155                 160

Ser Gln Asp Ile Gly Ser Ser Leu Asn Trp Leu Gln Gln Glu Pro Asp
                165                 170                 175

Gly Thr Ile Lys Arg Leu Ile Tyr Ala Thr Ser Ser Leu Asp Ser Gly
            180                 185                 190

Val Pro Lys Arg Phe Ser Gly Ser Arg Ser Gly Ser Asp Tyr Ser Leu
        195                 200                 205

Thr Ile Ser Ser Leu Glu Ser Glu Asp Phe Val Asp Tyr Tyr Cys Leu
    210                 215                 220

Gln Tyr Ala Ser Ser Pro Tyr Thr Phe Gly Gly Thr Lys Leu Glu
225                 230                 235                 240

Leu Lys Gly Leu Ala Val Ser Thr Ile Ser Ser Phe Phe Pro Pro Gly
            245                 250                 255

Tyr Gln Ile Ile Ser Phe Phe Leu Ala Leu Thr Ser Thr Ala Leu Leu
                260                 265                 270

Phe Leu Leu Phe Phe Leu Thr Leu Arg Phe Ser Val Val Lys Arg Gly
            275                 280                 285

Arg Lys Lys Leu Leu Tyr Ile Phe Lys Gln Pro Phe Met Arg Pro Val
        290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Arg Val Lys Phe Ser Arg Ser Ala Asp
                325                 330                 335

Ala Pro Ala Tyr Gln Gln Gly Gln Asn Gln Leu Tyr Asn Glu Leu Asn
            340                 345                 350

Leu Gly Arg Arg Glu Glu Tyr Asp Val Leu Asp Lys Arg Arg Gly Arg
        355                 360                 365

Asp Pro Glu Met Gly Gly Lys Pro Arg Arg Lys Asn Pro Gln Glu Gly
370                 375                 380

Leu Tyr Asn Glu Leu Gln Lys Asp Lys Met Ala Glu Ala Tyr Ser Glu
385                 390                 395                 400

Ile Gly Met Lys Gly Glu Arg Arg Arg Gly Lys Gly His Asp Gly Leu
                405                 410                 415

Tyr Gln Gly Leu Ser Thr Ala Thr Lys Asp Thr Tyr Asp Ala Leu His
            420                 425                 430

Met Gln Ala Leu Pro Pro Arg
            435

<210> SEQ ID NO 135
<211> LENGTH: 486
<212> TYPE: PRT
<213> ORGANISM: artificial sequence
<220> FEATURE:
<223> OTHER INFORMATION: 1C11-v3 polypeptide CAR sequence

<400> SEQUENCE: 135

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Ala Glu Leu
            20                  25                  30

Ala Arg Pro Gly Ala Ser Val Lys Met Ser Cys Lys Ala Ser Gly Tyr
        35                  40                  45

Thr Phe Thr Ser Tyr Thr Met His Trp Val Lys Gln Arg Pro Gly Gln
    50                  55                  60

Gly Leu Glu Trp Ile Gly Tyr Ile Asn Pro Ser Ser Gly Tyr Thr Glu
65                  70                  75                  80

Tyr Asn Gln Lys Phe Lys Asp Lys Thr Thr Leu Thr Ala Asp Lys Ser
                85                  90                  95

Ser Ser Thr Ala Tyr Met Gln Leu Ser Ser Leu Thr Ser Gly Asp Ser
            100                 105                 110

Ala Val Tyr Tyr Cys Ala Arg Arg Val Leu Trp Leu Arg Arg Gly Asp
        115                 120                 125

Tyr Trp Gly Gln Gly Thr Ile Leu Thr Val Ser Ala Gly Gly Gly Gly
    130                 135                 140

Ser Gly Gly Gly Gly Ser Gly Gly Gly Ser Met Glu Val Leu Ile
145                 150                 155                 160

Thr Gln Thr Pro Ser Ser Leu Ser Ala Ser Leu Gly Glu Arg Val Ser
            165                 170                 175

Leu Thr Cys Arg Ala Ser Gln Asp Ile Gly Ser Ser Leu Asn Trp Leu
        180                 185                 190

Gln Gln Glu Pro Asp Gly Thr Ile Lys Arg Leu Ile Tyr Ala Thr Ser
    195                 200                 205

Ser Leu Asp Ser Gly Val Pro Lys Arg Phe Ser Gly Ser Arg Ser Gly
210                 215                 220

Ser Asp Tyr Ser Leu Thr Ile Ser Ser Leu Glu Ser Glu Asp Phe Val
225                 230                 235                 240

Asp Tyr Tyr Cys Leu Gln Tyr Ala Ser Ser Pro Tyr Thr Phe Gly Gly
            245                 250                 255

Gly Thr Lys Leu Glu Leu Lys Thr Thr Thr Pro Ala Pro Arg Pro Pro
        260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
        420                 425                 430

Tyr Asn Glu Leu Gln Lys Asp Lys Met Ala Glu Ala Tyr Ser Glu Ile
    435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 136
<211> LENGTH: 468
<212> TYPE: PRT
<213> ORGANISM: artificial sequence
<220> FEATURE:
<223> OTHER INFORMATION: 1C11-v4 polypeptide CAR sequence

<400> SEQUENCE: 136

Glu Val Lys Leu Gln Glu Ser Gly Ala Glu Leu Ala Arg Pro Gly Ala
1               5                   10                  15

-continued

```
Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Val Leu Trp Leu Arg Gly Asp Tyr Trp Gly Gln Gly
            100                 105                 110

Thr Ile Leu Thr Val Ser Ala Gly Gly Gly Ser Gly Gly Gly Gly
        115                 120                 125

Ser Gly Gly Gly Gly Ser Met Glu Val Leu Ile Thr Gln Thr Pro Ser
130                 135                 140

Ser Leu Ser Ala Ser Leu Gly Glu Arg Val Ser Leu Thr Cys Arg Ala
145                 150                 155                 160

Ser Gln Asp Ile Gly Ser Ser Leu Asn Trp Leu Gln Gln Glu Pro Asp
                165                 170                 175

Gly Thr Ile Lys Arg Leu Ile Tyr Ala Thr Ser Ser Leu Asp Ser Gly
            180                 185                 190

Val Pro Lys Arg Phe Ser Gly Ser Arg Ser Gly Ser Asp Tyr Ser Leu
        195                 200                 205

Thr Ile Ser Ser Leu Glu Ser Glu Asp Phe Val Asp Tyr Tyr Cys Leu
210                 215                 220

Gln Tyr Ala Ser Ser Pro Tyr Thr Phe Gly Gly Gly Thr Lys Leu Glu
225                 230                 235                 240

Leu Lys Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Ile Ser Phe Phe Leu Ala Leu Thr Ser Thr Ala Leu Leu Phe Leu Leu
290                 295                 300

Phe Phe Leu Thr Leu Arg Phe Ser Val Val Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430
```

```
Lys Gly Glu Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 137
<211> LENGTH: 651
<212> TYPE: PRT
<213> ORGANISM: artificial sequence
<220> FEATURE:
<223> OTHER INFORMATION: 1C11-v5 polypeptide CAR sequence

<400> SEQUENCE: 137

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Val Leu Trp Leu Arg Gly Asp Tyr Trp Gly Gln Gly
            100                 105                 110

Thr Ile Leu Thr Val Ser Ala Gly Gly Gly Gly Ser Gly Gly Gly Gly
        115                 120                 125

Ser Gly Gly Gly Gly Ser Met Glu Val Leu Ile Thr Gln Thr Pro Ser
    130                 135                 140

Ser Leu Ser Ala Ser Leu Gly Glu Arg Val Ser Leu Thr Cys Arg Ala
145                 150                 155                 160

Ser Gln Asp Ile Gly Ser Ser Leu Asn Trp Leu Gln Gln Glu Pro Asp
                165                 170                 175

Gly Thr Ile Lys Arg Leu Ile Tyr Ala Thr Ser Ser Leu Asp Ser Gly
            180                 185                 190

Val Pro Lys Arg Phe Ser Gly Ser Arg Ser Gly Ser Asp Tyr Ser Leu
        195                 200                 205

Thr Ile Ser Ser Leu Glu Ser Glu Asp Phe Val Asp Tyr Tyr Cys Leu
    210                 215                 220

Gln Tyr Ala Ser Ser Pro Tyr Thr Phe Gly Gly Gly Thr Lys Leu Glu
225                 230                 235                 240

Leu Lys Glu Pro Lys Ser Pro Asp Lys Thr His Thr Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ala Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
    435                 440                 445

Phe Ser Cys Ser Val Met His Glu Ala Leu His Asn His Tyr Thr Gln
450                 455                 460

Lys Ser Leu Ser Leu Ser Pro Gly Lys Ile Tyr Ile Trp Ala Pro Leu
465                 470                 475                 480

Ala Gly Thr Cys Gly Val Leu Leu Leu Ser Leu Val Ile Thr Leu Tyr
                485                 490                 495

Cys Lys Arg Gly Arg Lys Lys Leu Leu Tyr Ile Phe Lys Gln Pro Phe
        500                 505                 510

Met Arg Pro Val Gln Thr Thr Gln Glu Glu Asp Gly Cys Ser Cys Arg
    515                 520                 525

Phe Pro Glu Glu Glu Glu Gly Gly Cys Glu Leu Arg Val Lys Phe Ser
530                 535                 540

Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
                565                 570                 575

Arg Arg Gly Arg Asp Pro Glu Met Gly Gly Lys Pro Arg Arg Lys Asn
        580                 585                 590

Pro Gln Glu Gly Leu Tyr Asn Glu Leu Gln Lys Asp Lys Met Ala Glu
    595                 600                 605

Ala Tyr Ser Glu Ile Gly Met Lys Gly Glu Arg Arg Arg Gly Lys Gly
610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg
                645                 650

<210> SEQ ID NO 138
<211> LENGTH: 654
<212> TYPE: PRT
<213> ORGANISM: artificial sequence
<220> FEATURE:
<223> OTHER INFORMATION: 1C11-v6 polypeptide CAR sequence

<400> SEQUENCE: 138

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30
```

-continued

Thr Met His Trp Val Lys Gln Arg Pro Gly Gln Gly Leu Glu Trp Ile
            35                  40                  45
Gly Tyr Ile Asn Pro Ser Ser Gly Tyr Thr Glu Tyr Asn Gln Lys Phe
 50                      55                  60
Lys Asp Lys Thr Thr Leu Thr Ala Asp Lys Ser Ser Ser Thr Ala Tyr
 65                  70                  75                  80
Met Gln Leu Ser Ser Leu Thr Ser Gly Asp Ser Ala Val Tyr Tyr Cys
                 85                  90                  95
Ala Arg Arg Val Leu Trp Leu Arg Gly Asp Tyr Trp Gly Gln Gly
                100                 105                 110
Thr Ile Leu Thr Val Ser Ala Gly Gly Gly Ser Gly Gly Gly
            115                 120                 125
Ser Gly Gly Gly Ser Met Glu Val Leu Ile Thr Gln Thr Pro Ser
130                 135                 140
Ser Leu Ser Ala Ser Leu Gly Glu Arg Val Ser Leu Thr Cys Arg Ala
145                 150                 155                 160
Ser Gln Asp Ile Gly Ser Ser Leu Asn Trp Leu Gln Gln Glu Pro Asp
                165                 170                 175
Gly Thr Ile Lys Arg Leu Ile Tyr Ala Thr Ser Ser Leu Asp Ser Gly
            180                 185                 190
Val Pro Lys Arg Phe Ser Gly Ser Arg Ser Gly Ser Asp Tyr Ser Leu
        195                 200                 205
Thr Ile Ser Ser Leu Glu Ser Glu Asp Phe Val Asp Tyr Tyr Cys Leu
    210                 215                 220
Gln Tyr Ala Ser Ser Pro Tyr Thr Phe Gly Gly Gly Thr Lys Leu Glu
225                 230                 235                 240
Leu Lys Glu Pro Lys Ser Pro Asp Lys Thr His Thr Cys Pro Pro Cys
                245                 250                 255
Pro Ala Pro Pro Val Ala Gly Pro Ser Val Phe Leu Phe Pro Pro Lys
            260                 265                 270
Pro Lys Asp Thr Leu Met Ile Ala Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln

-continued

```
            450                 455                 460
Lys Ser Leu Ser Leu Ser Pro Gly Lys Ile Ile Ser Phe Phe Leu Ala
465                 470                 475                 480

Leu Thr Ser Thr Ala Leu Leu Phe Leu Leu Phe Phe Leu Thr Leu Arg
                485                 490                 495

Phe Ser Val Val Lys Arg Gly Arg Lys Lys Leu Leu Tyr Ile Phe Lys
                    500                 505                 510

Gln Pro Phe Met Arg Pro Val Gln Thr Thr Gln Glu Glu Asp Gly Cys
            515                 520                 525

Ser Cys Arg Phe Pro Glu Glu Glu Gly Gly Cys Glu Leu Arg Val
530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
                580                 585                 590

Arg Lys Asn Pro Gln Glu Gly Leu Tyr Asn Glu Leu Gln Lys Asp Lys
                595                 600                 605

Met Ala Glu Ala Tyr Ser Glu Ile Gly Met Lys Gly Glu Arg Arg Arg
            610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650
```

<210> SEQ ID NO 139
<211> LENGTH: 49
<212> TYPE: DNA
<213> ORGANISM: homo sapiens
<220> FEATURE:
<223> OTHER INFORMATION: TRAC T01 target sequence

<400> SEQUENCE: 139
ttgtcccaca gatatccaga accctgaccc tgccgtgtac cagctgaga          49

<210> SEQ ID NO 140
<211> LENGTH: 530
<212> TYPE: PRT
<213> ORGANISM: artificial sequence
<220> FEATURE:
<223> OTHER INFORMATION: TAL binding domain TRAC_T01-L

<400> SEQUENCE: 140

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
```

```
            100                 105                 110
Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
            130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                    165                 170                 175

Val Ala Ile Ala Ser His Asp Gly Gly Lys Gln Ala Leu Glu Thr Val
                        180                 185                 190

Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
            210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                    245                 250                 255

Leu Glu Thr Val Gln Arg Leu Leu Pro Val Leu Cys Gln Ala His Gly
                        260                 265                 270

Leu Thr Pro Glu Gln Val Val Ala Ile Ala Ser Asn Ile Gly Gly Lys
                        275                 280                 285

Gln Ala Leu Glu Thr Val Gln Ala Leu Leu Pro Val Leu Cys Gln Ala
            290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                    325                 330                 335

Gln Ala His Gly Leu Thr Pro Glu Gln Val Val Ala Ile Ala Ser Asn
                        340                 345                 350

Ile Gly Gly Lys Gln Ala Leu Glu Thr Val Gln Ala Leu Leu Pro Val
                        355                 360                 365

Leu Cys Gln Ala His Gly Leu Thr Pro Gln Gln Val Val Ala Ile Ala
            370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                    405                 410                 415

Ile Ala Ser Asn Ile Gly Gly Lys Gln Ala Leu Glu Thr Val Gln Ala
                        420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                    485                 490                 495

Thr Val Gln Arg Leu Leu Pro Val Leu Cys Gln Ala His Gly Leu Thr
                        500                 505                 510

Pro Gln Gln Val Val Ala Ile Ala Ser Asn Gly Gly Gly Arg Pro Ala
            515                 520                 525
```

Leu Glu
    530

<210> SEQ ID NO 141
<211> LENGTH: 530
<212> TYPE: PRT
<213> ORGANISM: artificial sequence
<220> FEATURE:
<223> OTHER INFORMATION: TAL binding domain TRAC_T01-R

<400> SEQUENCE: 141

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 142
<211> LENGTH: 2814
<212> TYPE: DNA
<213> ORGANISM: artificial sequence
<220> FEATURE:
<223> OTHER INFORMATION: polynucleotide encoding TRAC_T01-L TALEN

<400> SEQUENCE: 142
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccccgcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480 ttgaccccc  agcaggtggt ggccatcgcc agcaatggcg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc ccccagcagg tggtggccat cgccagcaat   720
ggcggtggca agcaggcgct ggagacggtc agcggctgt  tgccggtgct gtgccaggcc   780
cacggcttga ccccggagca ggtggtggcc atcgccagcc acgatggcgg caagcaggcg   840
ctggagacgg tccagcggct gttgccggtg ctgtgccagg cccacggctt gaccccggag   900
caggtggtgg ccatcgccag ccacgatggc ggcaagcagg cgctggagac ggtccagcgg   960

| | |
|---|---|
| ctgttgccgg tgctgtgcca ggcccacggc ttgaccccgg agcaggtggt ggccatcgcc | 1020 |
| agccacgatg gcggcaagca ggcgctggag acggtccagc ggctgttgcc ggtgctgtgc | 1080 |
| caggcccacg gcttgacccc ggagcaggtg gtggccatcg ccagcaatat tggtggcaag | 1140 |
| caggcgctgg agacggtgca ggcgctgttg ccggtgctgt gccaggccca cggcttgacc | 1200 |
| ccggagcagg tggtggccat cgccagccac gatggcggca agcaggcgct ggagacggtc | 1260 |
| cagcggctgt tgccggtgct gtgccaggcc acggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccgg agcaggtggt ggccatcgcc agcaatattg gtggcaagca ggcgctggag | 1560 |
| acggtgcagg cgctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtg caggcgctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctga tgcagtgaaa aagggattg ggggatccta tcagccgttc ccagctggtg | 2220 |
| aagtccgagc tggaggagaa gaaatccgag ttgaggcaca gctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acgcgccat ctacaccgtg gctcccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca cccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 143
<211> LENGTH: 2832
<212> TYPE: DNA
<213> ORGANISM: artificial sequence
<220> FEATURE:
<223> OTHER INFORMATION: polynucleotide encoding TRAC_T01-R TALEN

<400> SEQUENCE: 143

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |

```
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt gccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt gccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc cagcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga aatccgagtt gaggcacaag    2280
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
```

```
cccaacgagt ggtggaaggt gtacccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                        2832
```